(12) United States Patent
Gambale et al.

(10) Patent No.: US 8,075,573 B2
(45) Date of Patent: Dec. 13, 2011

(54) SINGLE INTUBATION, MULTI-STITCH ENDOSCOPIC SUTURING SYSTEM

(75) Inventors: Richard A. Gambale, Tyngsboro, MA (US); Peter J. Lukin, Lancaster, MA (US); Paul C. DiCesare, Easton, CT (US); Christopher A. Battles, Hamden, CT (US); Jeffrey P. Radziunas, Wallingford, CT (US); Danial P. Ferreira, Milford, CT (US)

(73) Assignee: C.R. Bard, Inc., Murray Hill, NJ (US)

( * ) Notice: Subject to any disclaimer, the term of this patent is extended or adjusted under 35 U.S.C. 154(b) by 1707 days.

(21) Appl. No.: 10/847,190

(22) Filed: May 17, 2004

(65) Prior Publication Data

US 2005/0033319 A1     Feb. 10, 2005

Related U.S. Application Data

(60) Provisional application No. 60/471,248, filed on May 16, 2003.

(51) Int. Cl.
*A61B 17/04* (2006.01)
*A61B 17/12* (2006.01)

(52) U.S. Cl. ............................................. 606/145
(58) Field of Classification Search .............. 606/139, 606/144, 145, 148, 149, 146, 147, 150; 600/37, 600/104
See application file for complete search history.

(56) References Cited

U.S. PATENT DOCUMENTS

| | | | |
|---|---|---|---|
| 453,508 A | 6/1891 | Ruby |
| 650,822 A | 6/1900 | Cain |
| 730,152 A | 6/1903 | Pitner |
| 979,342 A | 12/1910 | Schaefer |
| 1,325,699 A | 12/1919 | Oesterhaus |
| 1,455,833 A | 5/1923 | Dale |
| 1,868,308 A | 7/1932 | Brumfield |
| 2,170,599 A | 8/1939 | Stricklen |
| 2,455,833 A | 12/1948 | Trombetta |
| 2,587,364 A | 2/1952 | Mitchell |

(Continued)

FOREIGN PATENT DOCUMENTS

DE     3909999 A1     9/1990

(Continued)

OTHER PUBLICATIONS

Bard Interventional Products Division, C. R. Bard, Inc., "RapidFire™ Multiple Band Ligator—Information for Use", No. AE1904601/01, Issued Jun. 1996.
Cook® Wilson-Cook Medical GI Endoscopy, Sales Literature, www.wilsoncook.com.
Filipi, Transoral, Flexible Endoscopic Suturing for Treatment of GERD: A Multicenter Trial, *Gastrointest Endosc* Apr. 2001; 53 (4): 416-422.

(Continued)

*Primary Examiner* — Gary Jackson
*Assistant Examiner* — Lindsey Bachman
(74) *Attorney, Agent, or Firm* — Wolf, Greenfield & Sacks, P.C.

(57) ABSTRACT

Provided is an endoscopic suturing system for joining internal body tissues in a variety of procedures. The system comprises a suturing capsule releasably mountable to the distal end of an endoscope and capable of forming multiple stitches in tissue at a plurality of locations without requiring withdrawal of the capsule from the patient between stitches. Also enclosed is a suture lock to secure the placed stitch that is delivered by a device introduced through the working channel of the indwelling endoscope. Suitable control handles for the suturing capsule and for the suture lock delivery device positioned at the proximal end of the endoscope are provided to facilitate operation by the user.

15 Claims, 39 Drawing Sheets

U.S. PATENT DOCUMENTS

| | | |
|---|---|---|
| 2,601,852 A | 7/1952 | Wendt |
| 2,610,631 A | 9/1952 | Calicchio |
| 2,621,655 A | 12/1952 | Olson |
| 2,650,593 A | 9/1953 | Weil et al. |
| 2,897,820 A | 10/1956 | Tauber |
| 2,880,728 A | 4/1959 | Rights |
| 3,013,559 A | 12/1961 | Thomas |
| 3,238,941 A | 3/1966 | Klein et al. |
| 3,470,834 A | 10/1969 | Bone |
| 3,470,875 A | 10/1969 | Johnson |
| 3,716,058 A | 2/1973 | Tanner |
| 3,757,781 A | 9/1973 | Smart |
| 3,760,810 A | 9/1973 | Hoorn |
| 3,842,840 A | 10/1974 | Schweizer |
| 3,845,772 A | 11/1974 | Smith |
| 3,858,571 A | 1/1975 | Rudolph |
| 4,126,124 A | 11/1978 | Miller |
| 4,144,876 A | 3/1979 | Deleo |
| 4,164,225 A | 8/1979 | Johnson et al. |
| 4,210,148 A | 7/1980 | Stivala |
| 4,216,777 A | 8/1980 | Pridemore |
| 4,226,239 A | 10/1980 | Polk et al. |
| 4,234,111 A | 11/1980 | Dischinger |
| 4,235,238 A | 11/1980 | Ogiu et al. |
| 4,236,470 A | 12/1980 | Stenson |
| 4,291,698 A | 9/1981 | Fuchs et al. |
| 4,345,601 A | 8/1982 | Fukuda |
| 4,414,908 A | 11/1983 | Eguchi et al. |
| 4,415,092 A | 11/1983 | Boyer |
| 4,440,171 A | 4/1984 | Nomoto et al. |
| 4,469,101 A | 9/1984 | Coleman et al. |
| 4,474,174 A | 10/1984 | Petruzzi |
| 4,493,319 A | 1/1985 | Polk et al. |
| D279,504 S | 7/1985 | Tump |
| 4,573,622 A | 3/1986 | Green et al. |
| 4,592,341 A | 6/1986 | Omagari et al. |
| 4,597,300 A | 7/1986 | Beardmore et al. |
| 4,597,390 A | 7/1986 | Mulhollan et al. |
| 4,602,635 A | 7/1986 | Mulhollan et al. |
| 4,607,620 A | 8/1986 | Storz |
| 4,615,472 A | 10/1986 | Nash |
| 4,621,640 A | 11/1986 | Mulhollan et al. |
| 4,637,816 A | 1/1987 | Mann |
| 4,665,906 A | 5/1987 | Jervis |
| 4,672,979 A | 6/1987 | Pohndorf |
| 4,706,653 A | 11/1987 | Yamamoto |
| 4,721,103 A | 1/1988 | Freedland |
| 4,735,194 A | 4/1988 | Stiegmann |
| 4,738,255 A | 4/1988 | Goble et al. |
| 4,741,330 A | 5/1988 | Hayhurst |
| 4,747,358 A | 5/1988 | Moll et al. |
| 4,759,364 A | 7/1988 | Boebel |
| 4,794,911 A | 1/1989 | Okada |
| 4,815,465 A | 3/1989 | Alvarado |
| 4,825,259 A | 4/1989 | Berry, Jr. |
| 4,841,888 A | 6/1989 | Mills et al. |
| 4,860,746 A | 8/1989 | Yoon |
| 4,890,615 A | 1/1990 | Caspari et al. |
| 4,898,156 A | 2/1990 | Gatturna et al. |
| 4,899,743 A | 2/1990 | Nicholson et al. |
| 4,923,461 A | 5/1990 | Caspari et al. |
| 4,927,428 A | 5/1990 | Richards |
| 4,932,962 A | 6/1990 | Yoon et al. |
| 4,936,823 A | 6/1990 | Colvin et al. |
| 4,946,468 A | 8/1990 | Li |
| 4,950,285 A | 8/1990 | Wilk |
| 4,961,741 A | 10/1990 | Hayhurst |
| 4,968,315 A | 11/1990 | Gatturna |
| 5,002,042 A | 3/1991 | Okada |
| 5,002,550 A | 3/1991 | Li |
| 5,037,021 A | 8/1991 | Mills et al. |
| 5,037,422 A | 8/1991 | Hayhurst et al. |
| 5,037,433 A | 8/1991 | Wilk et al. |
| 5,041,129 A | 8/1991 | Hayhurst et al. |
| 5,046,513 A | 9/1991 | Gatturna et al. |
| 5,059,201 A | 10/1991 | Asnis |
| 5,074,874 A | 12/1991 | Yoon et al. |
| 5,078,721 A | 1/1992 | McKeating |
| 5,078,731 A | 1/1992 | Hayhurst |
| 5,080,663 A | 1/1992 | Mills et al. |
| 5,084,058 A | 1/1992 | Li |
| 5,085,661 A | 2/1992 | Moss |
| 5,087,263 A | 2/1992 | Li |
| 5,100,417 A | 3/1992 | Cerier et al. |
| 5,100,418 A | 3/1992 | Yoon et al. |
| 5,100,421 A | 3/1992 | Christoudias |
| 5,102,421 A | 4/1992 | Anspach et al. |
| 5,116,349 A | 5/1992 | Aranyi |
| 5,123,913 A | 6/1992 | Wilk et al. |
| 5,125,553 A | 6/1992 | Oddsen et al. |
| 5,133,723 A | 7/1992 | Li et al. |
| 5,147,379 A | 9/1992 | Sabbaghian et al. |
| 5,152,769 A | 10/1992 | Baber |
| 5,163,945 A | 11/1992 | Ortiz et al. |
| 5,163,946 A | 11/1992 | Li |
| 5,171,251 A | 12/1992 | Bregen et al. |
| 5,176,682 A | 1/1993 | Chow |
| 5,176,691 A | 1/1993 | Pierce |
| 5,193,525 A | 3/1993 | Silverstein et al. |
| 5,199,566 A | 4/1993 | Ortiz et al. |
| 5,203,863 A | 4/1993 | Bidoia |
| 5,207,679 A | 5/1993 | Li |
| 5,207,690 A | 5/1993 | Rohrabacher |
| 5,207,694 A | 5/1993 | Broome |
| 5,211,650 A | 5/1993 | Noda |
| 5,213,093 A | 5/1993 | Swindle |
| 5,217,471 A | 6/1993 | Burkhart |
| 5,217,472 A | 6/1993 | Green et al. |
| 5,217,486 A | 6/1993 | Rice et al. |
| 5,220,928 A | 6/1993 | Oddsen |
| 5,224,946 A | 7/1993 | Hayhurst et al. |
| 5,234,444 A | 8/1993 | Christoudias |
| 5,236,445 A | 8/1993 | Hayhurst et al. |
| 5,242,431 A | 9/1993 | Kristiansen |
| 5,242,457 A | 9/1993 | Akopov et al. |
| 5,250,053 A | 10/1993 | Snyder |
| 5,254,126 A | 10/1993 | Filipi et al. |
| 5,257,637 A | 11/1993 | El Gazayerli |
| 5,258,015 A | 11/1993 | Li et al. |
| 5,258,016 A | 11/1993 | Dipoto et al. |
| 5,259,366 A | 11/1993 | Reydel et al. |
| 5,261,917 A | 11/1993 | Hasson et al. |
| 5,268,001 A | 12/1993 | Nicholson et al. |
| 5,269,789 A | 12/1993 | Chin et al. |
| 5,269,809 A | 12/1993 | Hayhurst et al. |
| 5,273,053 A | 12/1993 | Pohndorf |
| 5,279,311 A | 1/1994 | Snyder |
| 5,281,236 A | 1/1994 | Bagnato et al. |
| 5,281,237 A | 1/1994 | Gimpelson |
| 5,282,832 A | 2/1994 | Toso et al. |
| 5,284,485 A | 2/1994 | Kammerer et al. |
| 5,290,296 A | 3/1994 | Phillips |
| 5,290,297 A | 3/1994 | Phillips |
| 5,292,327 A | 3/1994 | Dodd et al. |
| 5,297,536 A | 3/1994 | Wilk |
| 5,304,184 A | 4/1994 | Hathaway et al. |
| 5,306,280 A | 4/1994 | Bregen et al. |
| 5,306,309 A | 4/1994 | Wagner et al. |
| 5,312,422 A | 5/1994 | Trott |
| 5,312,423 A | 5/1994 | Rosenbluth et al. |
| 5,312,438 A | 5/1994 | Johnson |
| 5,318,579 A | 6/1994 | Chow |
| 5,320,629 A | 6/1994 | Noda et al. |
| 5,320,630 A | 6/1994 | Ahmed |
| 5,324,308 A | 6/1994 | Pierce |
| 5,330,442 A | 7/1994 | Green et al. |
| 5,330,486 A | 7/1994 | Wilk |
| 5,333,624 A | 8/1994 | Tovey |
| 5,334,200 A | 8/1994 | Johnson |
| 5,336,229 A * | 8/1994 | Noda .................. 606/144 |
| 5,342,389 A | 8/1994 | Haber et al. |
| 5,344,060 A | 9/1994 | Gravener et al. |
| 5,350,385 A | 9/1994 | Christy |
| 5,354,298 A | 10/1994 | Lee et al. |
| 5,356,413 A | 10/1994 | Martins et al. |
| 5,356,416 A | 10/1994 | Chu et al. |
| 5,364,407 A | 11/1994 | Poll |

| Patent | Kind | Date | Inventor |
|---|---|---|---|
| 5,364,408 | A | 11/1994 | Gordon |
| 5,368,599 | A | 11/1994 | Hirsch et al. |
| 5,368,601 | A | 11/1994 | Sauer et al. |
| 5,370,662 | A | 12/1994 | Stone et al. |
| 5,372,599 | A | 12/1994 | Martins |
| 5,372,604 | A | 12/1994 | Trott |
| 5,376,101 | A | 12/1994 | Green et al. |
| 5,380,334 | A | 1/1995 | Torrie et al. |
| 5,383,905 | A | 1/1995 | Golds et al. |
| 5,389,103 | A | 2/1995 | Melzer et al. |
| 5,391,173 | A | 2/1995 | Wilk |
| 5,391,176 | A | 2/1995 | Torre |
| 5,391,182 | A | 2/1995 | Chin |
| 5,398,844 | A | 3/1995 | Zaslavsky et al. |
| 5,403,329 | A | 4/1995 | Hinchcliffe |
| 5,403,346 | A | 4/1995 | Loeser |
| 5,403,348 | A | 4/1995 | Bonutti |
| 5,405,351 | A | 4/1995 | Kinet et al. |
| 5,405,354 | A | 4/1995 | Sarrett |
| 5,405,359 | A | 4/1995 | Pierce |
| 5,409,499 | A | 4/1995 | Yi |
| 5,411,506 | A | 5/1995 | Goble et al. |
| 5,411,522 | A | 5/1995 | Trott |
| 5,411,523 | A | 5/1995 | Goble |
| 5,413,585 | A | 5/1995 | Pagedasa |
| 5,417,691 | A | 5/1995 | Hayhurst |
| 5,417,697 | A | 5/1995 | Wilk et al. |
| 5,417,699 | A | 5/1995 | Klein et al. |
| 5,423,834 | A | 6/1995 | Ahmed |
| 5,423,860 | A | 6/1995 | Lizardi et al. |
| 5,431,639 | A | 7/1995 | Shaw |
| 5,431,666 | A | 7/1995 | Sauer et al. |
| 5,433,722 | A | 7/1995 | Sharpe et al. |
| 5,437,680 | A | 8/1995 | Yoon |
| 5,439,467 | A | 8/1995 | Benderev et al. |
| 5,443,482 | A | 8/1995 | Stone et al. |
| 5,445,167 | A | 8/1995 | Yoon et al. |
| 5,447,512 | A | 9/1995 | Wilson et al. |
| 5,454,820 | A | 10/1995 | Kammerer et al. |
| 5,458,608 | A | 10/1995 | Wortrich |
| 5,458,609 | A | 10/1995 | Gordon et al. |
| 5,462,558 | A | 10/1995 | Kolesa et al. |
| 5,462,559 | A | 10/1995 | Ahmed |
| 5,462,561 | A | 10/1995 | Voda |
| 5,464,426 | A | 11/1995 | Bonutti |
| 5,466,241 | A | 11/1995 | Leroy et al. |
| 5,470,337 | A | 11/1995 | Moss |
| 5,474,565 | A | 12/1995 | Trott |
| 5,474,568 | A | 12/1995 | Scott |
| 5,474,572 | A | 12/1995 | Hayhurst |
| 5,474,573 | A | 12/1995 | Hatcher |
| 5,476,469 | A | 12/1995 | Hathaway et al. |
| 5,478,353 | A | 12/1995 | Yoon |
| 5,487,746 | A | 1/1996 | Yu et al. |
| 5,496,334 | A | 3/1996 | Klundt et al. |
| 5,501,691 | A | 3/1996 | Goldrath |
| 5,501,692 | A | 3/1996 | Riza |
| 5,507,754 | A | 4/1996 | Green et al. |
| 5,507,758 | A | 4/1996 | Thomason et al. |
| 5,507,797 | A | 4/1996 | Suzuki et al. |
| 5,514,159 | A | 5/1996 | Matula et al. |
| 5,520,700 | A | 5/1996 | Beyar et al. |
| 5,520,702 | A | 5/1996 | Saur et al. |
| 5,520,703 | A | 5/1996 | Essig et al. |
| 5,522,846 | A | 6/1996 | Bonutti |
| 5,527,318 | A | 6/1996 | McGarry |
| 5,527,321 | A | 6/1996 | Hinchliffe |
| 5,531,763 | A | 7/1996 | Mastri et al. |
| 5,542,432 | A | 8/1996 | Slater |
| 5,545,170 | A | 8/1996 | Hart |
| 5,545,180 | A | 8/1996 | Le et al. |
| 5,549,617 | A | 8/1996 | Green et al. |
| 5,562,686 | A | 10/1996 | Sauer et al. |
| 5,562,688 | A | 10/1996 | Riza |
| 5,562,689 | A | 10/1996 | Green et al. |
| 5,569,274 | A | 10/1996 | Rapacki et al. |
| 5,569,305 | A | 10/1996 | Bonutti |
| 5,571,116 | A | 11/1996 | Bolanos et al. |
| 5,571,117 | A | 11/1996 | Ahn |
| 5,575,800 | A | 11/1996 | Gordon |
| 5,578,044 | A | 11/1996 | Gordon et al. |
| 5,584,861 | A | 12/1996 | Swain et al. |
| 5,584,862 | A | 12/1996 | Bonutti |
| 5,586,986 | A | 12/1996 | Hinchliffe |
| 5,591,177 | A | 1/1997 | Lehrer |
| 5,591,180 | A | 1/1997 | Hinchliffe |
| 5,601,530 | A | 2/1997 | Nielsen et al. |
| 5,601,571 | A | 2/1997 | Moss |
| 5,601,575 | A | 2/1997 | Measamer et al. |
| 5,609,597 | A | 3/1997 | Lehrer |
| 5,618,290 | A | 4/1997 | Toy et al. |
| 5,618,314 | A | 4/1997 | Harwin et al. |
| 5,624,453 | A | 4/1997 | Ahmed |
| 5,626,590 | A | 5/1997 | Wilk |
| 5,626,614 | A * | 5/1997 | Hart ........................... 606/232 |
| 5,630,824 | A | 5/1997 | Hart |
| 5,645,553 | A | 7/1997 | Kolesa et al. |
| 5,658,313 | A | 8/1997 | Thal et al. |
| 5,662,664 | A | 9/1997 | Gordon et al. |
| 5,665,096 | A | 9/1997 | Yoon |
| 5,665,100 | A | 9/1997 | Yoon |
| 5,665,109 | A | 9/1997 | Yoon |
| 5,665,112 | A | 9/1997 | Thal |
| 5,681,328 | A | 10/1997 | Lamport et al. |
| 5,681,351 | A | 10/1997 | Jamiolkowski et al. |
| 5,683,417 | A | 11/1997 | Cooper |
| 5,683,419 | A | 11/1997 | Thal |
| 5,683,464 | A | 11/1997 | Wagner et al. |
| 5,693,060 | A | 12/1997 | Martin |
| 5,695,505 | A | 12/1997 | Yoon |
| 5,697,940 | A | 12/1997 | Chu et al. |
| 5,700,272 | A | 12/1997 | Gordon et al. |
| 5,702,397 | A | 12/1997 | Goble et al. |
| 5,709,693 | A | 1/1998 | Taylor |
| 5,720,765 | A | 2/1998 | Thal |
| 5,728,136 | A | 3/1998 | Thal |
| 5,730,747 | A | 3/1998 | Ek et al. |
| 5,735,793 | A | 4/1998 | Takahashi et al. |
| 5,735,877 | A | 4/1998 | Pagedas |
| 5,741,277 | A | 4/1998 | Gordon et al. |
| 5,741,281 | A | 4/1998 | Martin |
| 5,741,301 | A | 4/1998 | Pagedas |
| 5,752,963 | A | 5/1998 | Allard et al. |
| 5,755,730 | A | 5/1998 | Swain et al. |
| 5,759,188 | A | 6/1998 | Yoon |
| 5,766,186 | A | 6/1998 | Faraz et al. |
| 5,766,217 | A | 6/1998 | Christy |
| 5,772,672 | A | 6/1998 | Toy et al. |
| 5,782,776 | A | 7/1998 | Hani |
| 5,788,715 | A | 8/1998 | Watson, Jr. et al. |
| 5,792,151 | A | 8/1998 | Heck et al. |
| 5,792,153 | A * | 8/1998 | Swain et al. .................. 606/144 |
| 5,797,927 | A | 8/1998 | Yoon |
| 5,810,853 | A | 9/1998 | Yoon |
| 5,810,854 | A | 9/1998 | Beach |
| 5,814,056 | A | 9/1998 | Prosst et al. |
| 5,817,109 | A | 10/1998 | McGarry et al. |
| 5,817,111 | A | 10/1998 | Riza |
| 5,827,298 | A | 10/1998 | Hart et al. |
| 5,827,306 | A | 10/1998 | Yoon |
| 5,830,231 | A | 11/1998 | Geiges, Jr. |
| 5,853,416 | A | 12/1998 | Tolkoff |
| 5,860,946 | A | 1/1999 | Hofstatter |
| 5,860,992 | A | 1/1999 | Daniel et al. |
| 5,861,002 | A | 1/1999 | Desai |
| 5,868,760 | A | 2/1999 | McGuckin, Jr. |
| 5,897,487 | A | 4/1999 | Ouchi |
| 5,899,921 | A | 5/1999 | Caspari et al. |
| 5,902,321 | A | 5/1999 | Caspari et al. |
| 5,910,105 | A * | 6/1999 | Swain et al. .................. 600/131 |
| 5,919,199 | A | 7/1999 | Mers Kelly et al. |
| 5,919,208 | A | 7/1999 | Valenti |
| RE36,289 | E | 8/1999 | Le et al. |
| 5,931,844 | A | 8/1999 | Thompson et al. |
| 5,935,149 | A | 8/1999 | Ek |
| 5,938,586 | A | 8/1999 | Wilk et al. |
| 5,938,668 | A | 8/1999 | Scirica et al. |
| 5,947,983 | A | 9/1999 | Solar et al. |

| | | | | | | |
|---|---|---|---|---|---|---|
| 5,954,733 | A | 9/1999 | Yoon | 6,790,214 B2 | 9/2004 | Kraemer et al. |
| 5,957,937 | A | 9/1999 | Yoon | 6,824,544 B2 | 11/2004 | Boebel et al. |
| 5,972,001 | A | 10/1999 | Yoon | 6,835,199 B2 | 12/2004 | McGuckin, Jr. et al. |
| 5,984,917 | A | 11/1999 | Fleischman et al. | 6,893,448 B2 | 5/2005 | O'Quinn et al. |
| 5,984,932 | A | 11/1999 | Yoon | 6,908,427 B2 | 6/2005 | Fleener et al. |
| 5,993,466 | A | 11/1999 | Yoon | 6,916,332 B2 | 7/2005 | Adams |
| 5,993,467 | A | 11/1999 | Yoon | 6,936,054 B2 | 8/2005 | Chu |
| 5,997,556 | A | 12/1999 | Tanner | 6,944,570 B2 | 9/2005 | Neeser et al. |
| 6,001,110 | A | 12/1999 | Adams | 6,951,565 B2 | 10/2005 | Keane et al. |
| 6,007,551 | A | 12/1999 | Peifer et al. | 6,955,643 B2 | 10/2005 | Gellman et al. |
| 6,010,515 | A | 1/2000 | Swain et al. | 6,964,668 B2 | 11/2005 | Modesitt et al. |
| 6,010,525 | A | 1/2000 | Bonutti et al. | 6,972,027 B2 | 12/2005 | Fallin et al. |
| 6,015,428 | A | 1/2000 | Pagedas | 6,974,466 B2 | 12/2005 | Ahmed et al. |
| 6,024,755 | A | 2/2000 | Addis | 6,991,635 B2 | 1/2006 | Takamoto et al. |
| 6,042,601 | A | 3/2000 | Smith | 6,997,931 B2 | 2/2006 | Sauer et al. |
| 6,059,719 | A | 5/2000 | Yamamoto et al. | 6,997,932 B2 | 2/2006 | Dreyfuss et al. |
| 6,059,798 | A | 5/2000 | Tolkoff | 7,001,400 B1 | 2/2006 | Modesitt et al. |
| 6,066,160 | A | 5/2000 | Colvin et al. | 7,025,755 B2 | 4/2006 | Epstein |
| 6,071,233 | A | 6/2000 | Ishikawa et al. | 7,029,480 B2 | 4/2006 | Klein et al. |
| 6,071,292 | A | 6/2000 | Makower et al. | 7,029,481 B1 | 4/2006 | Burdulis, Jr. et al. |
| 6,074,401 | A | 6/2000 | Gardiner et al. | 7,033,370 B2 | 4/2006 | Gordon et al. |
| 6,086,600 | A | 7/2000 | Kortenbach | 7,048,748 B1 | 5/2006 | Üstüner |
| 6,086,608 | A | 7/2000 | Ek et al. | 7,048,749 B2 | 5/2006 | Kortenbach et al. |
| 6,096,051 | A | 8/2000 | Kortenbach et al. | 7,060,077 B2 | 6/2006 | Gordon et al. |
| 6,099,535 | A | 8/2000 | Lamport et al. | 7,060,078 B2 | 6/2006 | Hathaway et al. |
| 6,126,677 | A | 10/2000 | Ganaja et al. | 7,060,079 B2 | 6/2006 | Wulc et al. |
| 6,129,661 | A | 10/2000 | Iafrati et al. | 7,063,710 B2 * | 6/2006 | Takamoto et al. ............ 606/144 |
| 6,136,009 | A | 10/2000 | Mears | 7,063,715 B2 | 6/2006 | Onuki et al. |
| 6,139,555 | A | 10/2000 | Hart et al. | 7,131,979 B2 | 11/2006 | DiCarlo et al. |
| 6,149,658 | A | 11/2000 | Gardiner et al. | 7,141,055 B2 | 11/2006 | Abrams et al. |
| 6,159,224 | A | 12/2000 | Yoon | 7,150,750 B2 | 12/2006 | Damarati |
| 6,159,234 | A | 12/2000 | Bonutti et al. | 7,153,312 B1 | 12/2006 | Torrie et al. |
| 6,200,329 | B1 | 3/2001 | Fung et al. | 7,156,857 B2 | 1/2007 | Pasricha et al. |
| 6,228,098 | B1 | 5/2001 | Kayan et al. | 7,166,116 B2 | 1/2007 | Lizardi et al. |
| 6,241,140 | B1 | 6/2001 | Adams et al. | 7,169,157 B2 | 1/2007 | Kayan |
| 6,264,086 | B1 | 7/2001 | McGuckin, Jr. | 7,175,636 B2 | 2/2007 | Yamamoto et al. |
| 6,280,452 | B1 | 8/2001 | Mears | 7,179,266 B2 | 2/2007 | Kontos |
| 6,283,979 | B1 | 9/2001 | Mers Kelly et al. | 7,179,267 B2 | 2/2007 | Nolan et al. |
| 6,330,964 | B1 | 12/2001 | Kayan et al. | 7,211,093 B2 | 5/2007 | Sauer et al. |
| 6,346,111 | B1 | 2/2002 | Gordon et al. | 7,220,266 B2 * | 5/2007 | Gambale ....................... 606/144 |
| 6,355,050 | B1 | 3/2002 | Andreas et al. | 7,220,267 B2 | 5/2007 | Jones |
| 6,358,259 | B1 | 3/2002 | Swain et al. | 7,232,446 B1 | 6/2007 | Farris |
| 6,368,334 | B1 * | 4/2002 | Sauer ............................ 606/139 | 7,232,447 B2 | 6/2007 | Gellman et al. |
| 6,387,105 | B1 | 5/2002 | Gifford, III et al. | 7,235,087 B2 | 6/2007 | Modesitt et al. |
| 6,398,795 | B1 | 6/2002 | McAlister et al. | 7,704,264 B2 | 4/2010 | Ewers et al. |
| 6,428,548 | B1 | 8/2002 | Durgin et al. | 2001/0056282 A1 | 12/2001 | Sonnenschein et al. |
| 6,436,108 | B1 | 8/2002 | Mears | 2002/0022851 A1 | 2/2002 | Kalloo et al. |
| 6,443,963 | B1 | 9/2002 | Baldwin et al. | 2002/0026159 A1 | 2/2002 | Zhu et al. |
| 6,450,391 | B1 | 9/2002 | Kayan et al. | 2002/0055750 A1 | 5/2002 | Durgin et al. |
| 6,451,031 | B1 | 9/2002 | Kontos | 2002/0055752 A1 | 5/2002 | Schraft et al. |
| 6,454,778 | B2 | 9/2002 | Kortenbach | 2002/0055757 A1 | 5/2002 | De la Torre et al. |
| 6,464,707 | B1 | 10/2002 | Bjerken | 2002/0065523 A1 | 5/2002 | McAlister et al. |
| 6,514,265 | B2 | 2/2003 | Ho et al. | 2002/0082616 A1 | 6/2002 | McAlister et al. |
| 6,533,796 | B1 | 3/2003 | Sauer et al. | 2002/0107530 A1 | 8/2002 | Sauer et al. |
| 6,544,281 | B2 * | 4/2003 | ElAttrache et al. ............ 606/232 | 2002/0143346 A1 | 10/2002 | McGuckin, Jr. et al. |
| 6,547,725 | B1 | 4/2003 | Paolitto et al. | 2002/0173800 A1 | 11/2002 | Dreyfuss et al. |
| 6,551,329 | B1 | 4/2003 | Kortenbach et al. | 2002/0177847 A1 | 11/2002 | Long et al. |
| 6,551,330 | B1 | 4/2003 | Bain et al. | 2002/0183768 A1 | 12/2002 | Deem et al. |
| 6,551,332 | B1 | 4/2003 | Nguyen et al. | 2002/0193808 A1 | 12/2002 | Belef et al. |
| 6,554,845 | B1 | 4/2003 | Fleenor et al. | 2002/0198542 A1 | 12/2002 | Yamamoto et al. |
| 6,558,400 | B2 | 5/2003 | Deem et al. | 2003/0004544 A1 | 1/2003 | Kawashima et al. |
| 6,572,629 | B2 | 6/2003 | Kalloo et al. | 2003/0045891 A1 | 3/2003 | Yamamoto et al. |
| 6,592,596 | B1 | 7/2003 | Geitz | 2003/0078600 A1 | 4/2003 | O'Quinn et al. |
| 6,607,541 | B1 | 8/2003 | Gardiner et al. | 2003/0109892 A1 | 6/2003 | Deem et al. |
| 6,613,058 | B1 | 9/2003 | Goldin | 2003/0120289 A1 | 6/2003 | McGuckin, Jr. et al. |
| 6,629,630 | B2 | 10/2003 | Adams | 2003/0139752 A1 | 7/2003 | Pasricha et al. |
| 6,652,538 | B2 | 11/2003 | Kayan et al. | 2003/0167062 A1 | 9/2003 | Gambale et al. |
| 6,675,809 | B2 | 1/2004 | Stack et al. | 2003/0171651 A1 | 9/2003 | Page et al. |
| 6,689,130 | B2 | 2/2004 | Arai et al. | 2003/0171760 A1 | 9/2003 | Gambale et al. |
| 6,695,764 | B2 | 2/2004 | Silverman et al. | 2003/0176880 A1 | 9/2003 | Long et al. |
| 6,716,222 | B2 | 4/2004 | McAlister et al. | 2003/0181925 A1 | 9/2003 | Bain et al. |
| 6,719,763 | B2 | 4/2004 | Chung et al. | 2003/0208208 A1 | 11/2003 | Chu |
| 6,736,828 | B1 | 5/2004 | Adams et al. | 2003/0208209 A1 | 11/2003 | Gambale et al. |
| 6,743,241 | B2 | 6/2004 | Kerr | 2003/0208213 A1 | 11/2003 | Manzo |
| 6,746,460 | B2 | 6/2004 | Gannoe et al. | 2003/0233104 A1 | 12/2003 | Gellman et al. |
| 6,755,843 | B2 | 6/2004 | Chung et al. | 2003/0233107 A1 | 12/2003 | Gellman et al. |
| 6,770,084 | B1 | 8/2004 | Bain et al. | 2003/0233108 A1 | 12/2003 | Gellman et al. |
| 6,773,440 | B2 | 8/2004 | Gannoe et al. | 2003/0236535 A1 | 12/2003 | Onuki et al. |
| 6,786,913 | B1 | 9/2004 | Sancoff et al. | 2003/0236536 A1 | 12/2003 | Grigoryants et al. |

| | | |
|---|---|---|
| 2004/0006351 A1 | 1/2004 | Gannoe et al. |
| 2004/0009224 A1 | 1/2004 | Miller |
| 2004/0010271 A1 | 1/2004 | Kortenbach |
| 2004/0030347 A1 | 2/2004 | Gannoe et al. |
| 2004/0034369 A1 | 2/2004 | Sauer et al. |
| 2004/0034371 A1 | 2/2004 | Lehman et al. |
| 2004/0044353 A1 | 3/2004 | Gannoe |
| 2004/0068272 A1 | 4/2004 | Sauer et al. |
| 2004/0087969 A1 | 5/2004 | Kayan et al. |
| 2004/0087978 A1 | 5/2004 | Velez et al. |
| 2004/0092892 A1 | 5/2004 | Kagan et al. |
| 2004/0092963 A1 | 5/2004 | Moll et al. |
| 2004/0133147 A1 | 7/2004 | Woo |
| 2004/0138704 A1 | 7/2004 | Gambale et al. |
| 2004/0158125 A1 | 8/2004 | Aznoian et al. |
| 2004/0158263 A1 | 8/2004 | McAlister et al. |
| 2004/0158264 A1 | 8/2004 | Adams et al. |
| 2004/0162567 A9 | 8/2004 | Adams |
| 2004/0162568 A1 | 8/2004 | Saadat et al. |
| 2004/0167546 A1 | 8/2004 | Saadat et al. |
| 2004/0172047 A1 | 9/2004 | Gellman et al. |
| 2004/0181242 A1 | 9/2004 | Stack et al. |
| 2004/0186502 A1 | 9/2004 | Sampson et al. |
| 2004/0193190 A1 | 9/2004 | Liddicoat et al. |
| 2004/0210241 A1 | 10/2004 | James et al. |
| 2004/0225183 A1 | 11/2004 | Michlitsch et al. |
| 2004/0225305 A1 | 11/2004 | Ewers et al. |
| 2004/0236353 A1 | 11/2004 | Bain et al. |
| 2004/0236356 A1 | 11/2004 | Rioux et al. |
| 2005/0021055 A1 | 1/2005 | Toubia et al. |
| 2005/0033319 A1 | 2/2005 | Gambale et al. |
| 2005/0033320 A1 | 2/2005 | McGuckin, Jr. et al. |
| 2005/0055038 A1 | 3/2005 | Kelleher et al. |
| 2005/0065536 A1 | 3/2005 | Ewers et al. |
| 2005/0070931 A1 | 3/2005 | Rhodemann et al. |
| 2005/0075652 A1 | 4/2005 | Byrum et al. |
| 2005/0075653 A1 | 4/2005 | Saadat et al. |
| 2005/0075654 A1 | 4/2005 | Kelleher |
| 2005/0090837 A1 | 4/2005 | Sixto et al. |
| 2005/0090841 A1 | 4/2005 | Morrison |
| 2005/0096673 A1 | 5/2005 | Stack et al. |
| 2005/0107807 A1 | 5/2005 | Nakao |
| 2005/0119671 A1 | 6/2005 | Reydel et al. |
| 2005/0149067 A1 | 7/2005 | Takemoto et al. |
| 2005/0149072 A1 | 7/2005 | DeVries et al. |
| 2005/0154402 A1 | 7/2005 | Sauer et al. |
| 2005/0154403 A1 | 7/2005 | Sauer et al. |
| 2005/0165419 A1 | 7/2005 | Sauer et al. |
| 2005/0177176 A1 | 8/2005 | Gerbi et al. |
| 2005/0192599 A1 | 9/2005 | Demarais |
| 2005/0222589 A1 | 10/2005 | Chu |
| 2005/0245945 A1 | 11/2005 | Ewers et al. |
| 2005/0250984 A1 | 11/2005 | Lam et al. |
| 2005/0251153 A1 | 11/2005 | Sakamoto et al. |
| 2005/0256587 A1 | 11/2005 | Egan |
| 2005/0261712 A1 | 11/2005 | Balbierz et al. |
| 2005/0288688 A1 | 12/2005 | Sakamoto et al. |
| 2006/0004385 A1 | 1/2006 | Gellman et al. |
| 2006/0011698 A1 | 1/2006 | Okada et al. |
| 2006/0030866 A1 | 2/2006 | Schreck |
| 2006/0047289 A1 | 3/2006 | Fogel |
| 2006/0069397 A1 | 3/2006 | Nobles et al. |
| 2006/0079914 A1 | 4/2006 | Modesitt et al. |
| 2006/0111732 A1 | 5/2006 | Gibbens et al. |
| 2006/0142784 A1 | 6/2006 | Kontos |
| 2006/0142785 A1 | 6/2006 | Modesitt et al. |
| 2006/0149298 A1 | 7/2006 | Wulc et al. |
| 2006/0155307 A1 | 7/2006 | Rosch |
| 2006/0178681 A1 | 8/2006 | Kortenbach et al. |
| 2006/0190016 A1 | 8/2006 | Onuki et al. |
| 2006/0206124 A1 | 9/2006 | Milliman et al. |
| 2006/0253126 A1 | 11/2006 | Bjerken et al. |
| 2006/0253127 A1 | 11/2006 | Bjerken |
| 2006/0253144 A1 | 11/2006 | Mikkaichi |
| 2006/0259046 A1 | 11/2006 | De la Torre et al. |
| 2006/0259047 A1 | 11/2006 | Hathaway et al. |
| 2006/0271075 A1 | 11/2006 | Bilotti et al. |
| 2006/0282088 A1 | 12/2006 | Ryan |
| 2006/0282089 A1 | 12/2006 | Stokes et al. |
| 2006/0282090 A1 | 12/2006 | Stokes et al. |
| 2006/0282091 A1 | 12/2006 | Shelton, IV et al. |
| 2006/0282092 A1 | 12/2006 | Stokes et al. |
| 2006/0282093 A1 | 12/2006 | Shelton, IV et al. |
| 2006/0282094 A1 | 12/2006 | Stokes et al. |
| 2006/0282095 A1 | 12/2006 | Stokes et al. |
| 2006/0282096 A1 | 12/2006 | Papa et al. |
| 2006/0282097 A1 | 12/2006 | Ortiz et al. |
| 2006/0282098 A1 | 12/2006 | Shelton, IV et al. |
| 2006/0287657 A1 | 12/2006 | Bachman |
| 2006/0293699 A1 | 12/2006 | Robertson |
| 2007/0005079 A1 | 1/2007 | Zarbatany et al. |
| 2007/0010836 A1 | 1/2007 | Grigoryants et al. |
| 2007/0032798 A1 | 2/2007 | Pantages et al. |
| 2007/0032799 A1 | 2/2007 | Pantages et al. |
| 2007/0043385 A1 | 2/2007 | Nobles et al. |
| 2007/0049954 A1 | 3/2007 | Caty et al. |
| 2007/0055292 A1 | 3/2007 | Ortiz et al. |
| 2007/0060929 A1 | 3/2007 | Onishi et al. |
| 2007/0060932 A1 | 3/2007 | Stack et al. |
| 2007/0073318 A1 | 3/2007 | Carter et al. |
| 2007/0073319 A1 | 3/2007 | Mikkaichi et al. |
| 2007/0073323 A1 | 3/2007 | Carter et al. |
| 2007/0088372 A1 | 4/2007 | Gellman et al. |
| 2007/0093854 A1 | 4/2007 | Kayan |
| 2007/0112362 A1 | 5/2007 | Mikkaichi et al. |
| 2007/0112363 A1 | 5/2007 | Adams |
| 2007/0118150 A1 | 5/2007 | Weber |
| 2007/0123914 A1 | 5/2007 | Lizardi et al. |
| 2007/0129735 A1 | 6/2007 | Filipi et al. |
| 2007/0135825 A1 | 6/2007 | Binmoeller |
| 2007/0149986 A1 | 6/2007 | Morris et al. |
| 2007/0162056 A1 | 7/2007 | Gerbi et al. |
| 2007/0162057 A1 | 7/2007 | Kraemer et al. |
| 2007/0162058 A1 | 7/2007 | Kraemer et al. |

FOREIGN PATENT DOCUMENTS

| | | |
|---|---|---|
| EP | 0477020 | 3/1992 |
| EP | 0558031 | 9/1993 |
| EP | 0 591991 A2 | 4/1994 |
| EP | 0 598219 A2 | 5/1994 |
| EP | 1749480 | 7/2007 |
| EP | 1749482 | 7/2007 |
| EP | 1759639 | 7/2007 |
| GB | 2165559 | 4/1986 |
| JP | 7-136177 | 5/1995 |
| JP | 10-500318 | 1/1998 |
| WO | 91/08708 | 6/1991 |
| WO | WO 96/09796 | 4/1996 |
| WO | WO 96/20647 | 7/1996 |
| WO | WO 99/22650 | 5/1999 |
| WO | WO 01/66001 | 9/2001 |
| WO | WO 01/66018 | 9/2001 |
| WO | WO 01/87144 | 11/2001 |
| WO | WO 01/89370 | 11/2001 |
| WO | WO 01/89393 | 11/2001 |
| WO | 2004/021894 | 3/2004 |
| WO | 2004/069056 | 8/2004 |
| WO | 2005/020802 | 3/2005 |
| WO | 2006/027014 | 3/2006 |
| WO | 2007/019268 | 2/2007 |

OTHER PUBLICATIONS

Lehman et al., "Endoscopic Gastroesophageal Suturing: Does Addition of Cautery Aid Plication Persistence?" *Digestive Disease Week* Poster Board Presentation—May 2000, On-line Abstract Feb. 2000.

Martinez-Serna et al., Endoscopic Valvuloplasty for GERD, *Gastrointest Endosc* Nov. 2000; 52 (5): 663-70.

Sherman et al., "Efficacy of Endoscopic Sphincterotomy and Surgical Sphincteroplasty for Patients with Sphincter of Oddi Dysfunction: Randomized, Prospective Study", *Gastrointest Endosc*, vol. 37, No. 2, 1991, p. 249 (Abstract).

Sherman et al., "Endoscopic Sphincterotomy Induced Hemorrhage: Treatment with Multipolar Electrocoagulation", *Gastrointest Endosc*, vol. 37, No. 2, 1991, p. 249 (Abstract).

\* cited by examiner

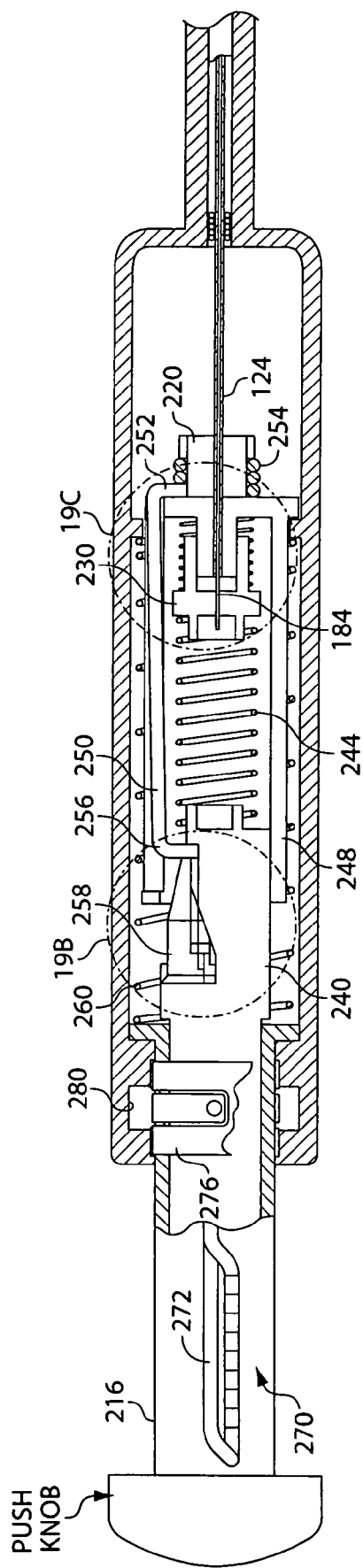
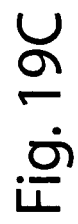
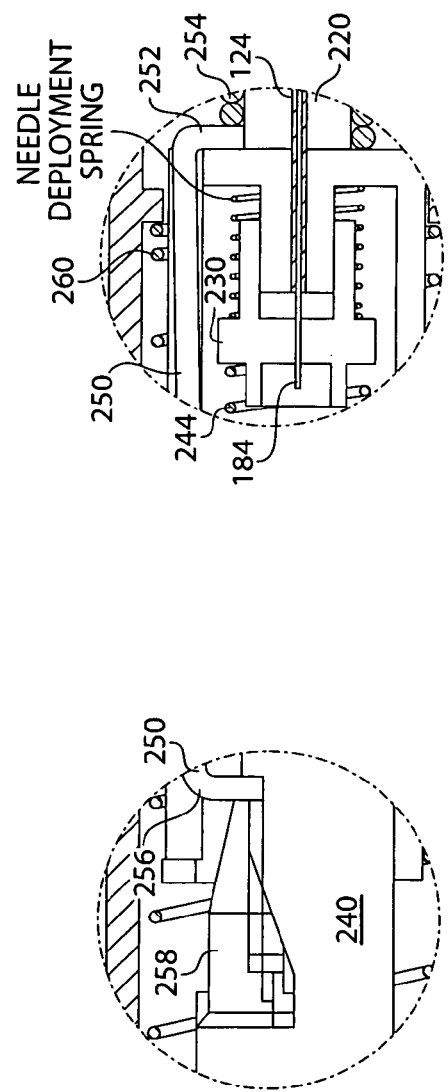
Fig. 19A
Fig. 19B
Fig. 19C

SINGLE INTUBATION, MULTI-STITCH ENDOSCOPIC SUTURING SYSTEM

RELATED APPLICATIONS

This application claims the benefit of U.S. Provisional Application No. 60/471,248, filed on May 16, 2003, the entire teachings of which are incorporated herein by reference.

FIELD OF THE INVENTION

The present invention relates to devices and methods for securing together tissues of the human body. In particular, the invention pertains to an endoscopic suturing system.

BACKGROUND OF THE INVENTION

Endoscopic apposition devices are devices that can be used in the body of a patient without the need to make an external incision in the patient, the device being controlled externally of the patient by endoscopic means. The device may comprise a sewing or stapling device for use in flexible endoscopy, though it is also applicable to devices for use in rigid endoscopy. Such devices have been found to be useful in the treatments of the digestive system, with the endoscope being inserted through a patient's esophagus. In particular, such devices have been found useful in treating gastro-esophageal reflux disease (GERD). In a procedure for treating GERD, stitches are placed to form tissue plications at the junction of the esophagus and stomach. The minor anatomical change resulting from the plication formation appears to relieve the symptoms of GERD in some patients.

Sewing devices of this general type are described in, for example, U.S. Pat. Nos. 5,080,663 and 5,792,153, which are incorporated by reference herein. Those patents disclose a sewing device for passing a thread through a tissue portion, which comprises a hollow needle movable between a first position in which it is out of the tissue portion and a second position in which it passes through the tissue portion, and a thread carrier adapted to be attached to the thread and being receivable within the hollow needle. The sewing device comprises a body, which defines a cavity within which the tissue portion can be held by means of suction, and the hollow needle is mounted for movement in the body between the first and second positions.

Two particular embodiments are described a single stitch sewing device, and a multiple stitch sewing device. In the single stitch device the thread carrier is transported by the needle through the tissue as the latter passes from its first position to its second position. When the needle returns to its first position, the thread carrier is left behind in the distal end of the sewing capsule. In the multiple stitch device, the same procedure occurs, but it is followed by a further step in which the hollow needle travels from its first position to its second position, picks up the thread carrier, and returns it. A second stitch may be formed during the next step. The whole sequence of steps is repeated as many times as may be required to form the desired number of stitches.

After placement of the sutures through the tissue, the suture must be secured tightly by knots or by a mechanical locking device. U.S. application Ser. Nos. 10/220,413 ("Suture Clips, Delivery Devices and Methods", filed Mar. 13, 2003) and 10/275,534 ("Tissue Capturing and Suturing Device and Method", filed Nov. 6, 2002), which are incorporated by reference herein in their entirety, disclose mechanical locking devices for securing a suture in an internal body location that are deliverable by an endoscope. These applications correspond to PCT Publication Nos. WO 01/66001 and WO 01/89393, respectively. However, due to their large size, these systems require that the endoscope be removed from the patient in order for the delivery device to be navigated to the suture location.

Minimizing the number of intubations and reducing the procedure time during which the patient must be kept under conscious sedation are important considerations in any endoscopic procedure. Prior art suturing devices must be withdrawn from the patient for each successive stitch made with the single-stitch embodiment. The use of the devices is, thus, time consuming, cumbersome and of some risk to the patient due to the multiple intubations and danger of perforation of the esophagus. It would be desirable to provide an endoscopic tissue apposition device that minimizes procedure time and the number of intubations while still making and securing multiple stitches during the procedure.

SUMMARY OF THE INVENTION

The present invention provides an endoscopic tissue apposition device capable of securing multiple tissue sites together with only one intubation of an endoscope carrying a suturing capsule at its distal end into the patient. To place the sutures, the system provides a suturing capsule that may be releasably secured to the distal end of a variety of commonly used endoscopes. The suturing capsule comprises a tissue suction chamber for capturing a section of tissue, a needle slidable along a needle track that passes through the suction chamber and a suture tag joined to a suture that is releasably securable to the needle.

To make multiple stitches without requiring removal of the device for reloading of suture thread, the capsule also includes a suture catch at its distal end, distal to the suction chamber, to receive the suture tag from the needle as it is passed through captured tissue. After carrying the suture tag and suture from a proximal side of captured tissue through to the distal side of the tissue, the tag can be left behind in the suture tag catch and needle withdrawn proximally leaving the suture passed through the captured tissue portion. A suture tag lock is provided on the needle to selectively capture the suture tag on the needle when it is delivered and picked up from the suture tag catch at the distal end of the capsule. Tissue then can be released from the capsule and either the tag recaptured by the needle in readiness for another stitch through a different captured tissue portion (approaching from the proximal side of the tissue) or the tag can be left in place and another tissue portion captured so that when the needle is advanced distally to capture the tag, the proximally withdrawing needle will carry suture through the tissue in a proximal direction. By shuttling the tag and its associated suture through a series of captured tissue portions in this fashion, a plurality of stitches can be formed without requiring removal of the capsule for reloading.

The needle and suture tag lock are selectively operated from the proximal end of the endoscope by a control handle. The control handle is releasably securable to the proximal end of the endoscope such that it is in communication with the working channel port of the endoscope handle. Control shafts joined to the handle extend through the working channel of the endoscope and control operation of the needle and the suture tag lock by their longitudinal movement initiated at the handle. The handle may have one longitudinal operating member to control both the movement of the needle and the release and securement of the suture tag lock.

Because there are four stages of needle operation during the tag shuttling through a tissue portion, when only a single longitudinal member is provided on the handle, a segmented operation of the longitudinal control member is preferred to indicate to the user which stage of needle operation is occurring. For example, the control member should indicate to the user a first stage when the longitudinal member is not depressed and the needle with tag loaded is proximal to the suction chamber. When the needle is advanced through tissue and is releasing the tag, bottoming out of the longitudinal member against the handle indicates the second stage of operation. The longitudinal member should return automatically to withdraw the needle proximally while leaving the tag behind in the suture tag catch (the third stage). The handle should provide an idle position at the third stage in which the needle is withdrawn proximally from the tissue without the tag and is in readiness to drive distally again to pick up the tag. During automatic return of the needle proximally, such as by a return spring, vacuum also can be discontinued automatically at the end of the return stroke so the tissue portion is released with suture thread now passing through it. Stage four occurs when the needle is advanced distally again to recapture the suture tag (either with tissue suctioned into the chamber or to reposition the tag prior to tissue capture). Depression of the longitudinal operation member again initiates stage four when the needle has reached the distal end of its stroke and recaptured the suture tag. Release of the longitudinal operation member from stage four returns the handle and the needle back to their initial state: stage one.

The suturing capsule control handle may also include vacuum controls to selectively suction tissue into the suction chamber during the course of suturing. A vacuum supply routed through the handle may then be conveniently turned on by the user by a switch on the handle. Optionally, a vacuum interlock feature may be provided that prevents operation of the device if a sufficient negative line pressure is not achieved to insure that tissue is fully suctioned into the chamber so that the needle and suture achieve a sufficient penetration depth. The vacuum control may also include a feature that automatically discontinues vacuum to the suction chamber once the needle has completed its proximal withdrawal stroke from the tissue. Additionally, the control handle may employ other useful features such as a suture tensioning mechanism to keep the suture taut during the procedure so that it moves proximally and distally with the movement of the needle rather than just distally, which may lead to bunching up the suture material in the suction chamber area.

After stitches have been formed through the several selected tissue locations, the suture leads must be secured to hold the suture tightly in position through the tissue. The present suturing system also provides a suture lock that may be applied to the suture leads to secure them with a delivery device that may be passed through the working channel of the endoscope so that removal of the endoscope is not required in order to complete the procedure. The suture lock comprises a ring and a plug sized to frictionally engage the inside surface of the ring so that suture leads passing through the ring become captured between the two components. To secure a suture, the suture leads are guided through the ring, and it is advanced to the suture location at which point the plug may be inserted into the ring while holding the suture taut so that it becomes captured in a tightened condition through the tissue.

The suture lock may be delivered to the tissue location and secured by a delivery device comprising a shaft and distal operating end that are passable through the working channel of the endoscope and a control handle at the proximal end of the shaft for controlling the operating end to assemble the ring and plug. The distal operating end of the delivery device should comprise a receptacle to hold at least one ring and one plug in the disassembled configuration so that it can be guided to the suture location with suture leads passing through the open ring. The receptacle may be configured as a cage defined by four arms attached in a hinged fashion only at their proximal ends to a central bushing member to permit their distal ends to be selectively closed or opened to release an assembled plug and ring. The fingers of the cage must remain closed during assembly of the plug into the ring to provide resistance to the assembly force of inserting the ring into the plug, but then may be selectively opened to release the secured suture lock.

To selectively open and close the arms of the cage and to sever the suture lead after assembly of the suture lock is completed, an outer sleeve slidable over the fingers of the cage may be provided. When the cage member is proximally within the sleeve such that the sleeve is over the distal ends of the fingers, the free distal ends of the fingers remain held radially inward in a closed configuration to retain the ring and plug. When the cage is moved distally relative to the sleeve so that the sleeve is positioned proximally over the hinged area of the fingers, the distal free ends of the fingers are permitted to spread apart radially to permit release of the ring and plug. To assemble the ring and plug while the fingers of the plug are restrained closed, the plug is pushed distally into the ring by a pusher shaft that slides longitudinally relative to the cage that holds the ring from longitudinal movement during assemble. After the plug has been inserted into the ring and the cage has been moved distally relative to the sleeve, the hinged fingers resiliently spring open (distal ends move radially outward) to release the plug and ring assembly.

The cage, outer sleeve and pusher should be joined to a control handle at the proximal end of the endoscope by control shafts, longitudinally slidable through the working channel of the endoscope to cause movement of the distal components to operate the distal end effectively, the handle may include two control members available to the user to achieve the needed relative motion to assemble and release the ring and plug. The handle should include at least one longitudinal slidable member joined to the pusher in order to advance the plug into the ring and an outer sheath joined to the cage and outer sheath to resist the distal longitudinal movement of the pusher and to achieve sliding movement of the outer sleeve to open the cage fingers.

It is an object of the present invention to provide an endoscopic suturing system that is capable of creating stitches in multiple distinct internal tissue areas while requiring only one intubation of the endoscope or insertion of a laproscope.

It is another object of the present invention to provide an endoscopic suturing capsule that provides a tissue suction chamber and a needle slidable through tissue captured therein to deliver a suture carrying tag through successively captured tissue portions to form a stitches in each separate portion.

It is another object of the present invention to provide a control handle for a multiple stitch endoscopic suturing capsule that permits the user to input only a single longitudinal movement of a control mechanism in order to complete a stitch of suture through a tissue portion and return the system to a state of readiness for a second stitch.

It is another object of the present invention to provide an endoscopic suturing system comprising a suturing capsule having a needle and suture tag capturable on the needle by a suture lock and a suture catch in the capsule, a control handle for operating the components of the suture capsule, a suture lock for securing the leads of suture delivered to tissue and a suture lock delivery device for assembling and releasing the suture lock at the internal tissue location.

It is another object of the present invention to provide a suture lock comprising a ring and a plug frictionally engageable within the ring to capture suture leads therebetween and a suture lock delivery device having a shaft and distal operational member and receptacle passable through the working channel of an endoscope and a control handle positionable at the proximal end of an endoscope to operate the distal member to deliver, assemble and release the ring and plug components of the suture lock to secure a suture.

BRIEF DESCRIPTION OF THE DRAWINGS

The foregoing and other objects and advantages of the invention will be appreciated more fully from the following further description thereof, with reference to the accompanying diagrammatic drawings wherein:

FIG. 19A is a sectional view of the suture control handle; FIGS. 19B and 19C are detailed views of components shown in the sectional view of FIG. 19A;

DESCRIPTION OF THE ILLUSTRATIVE EMBODIMENTS

Figure 1:
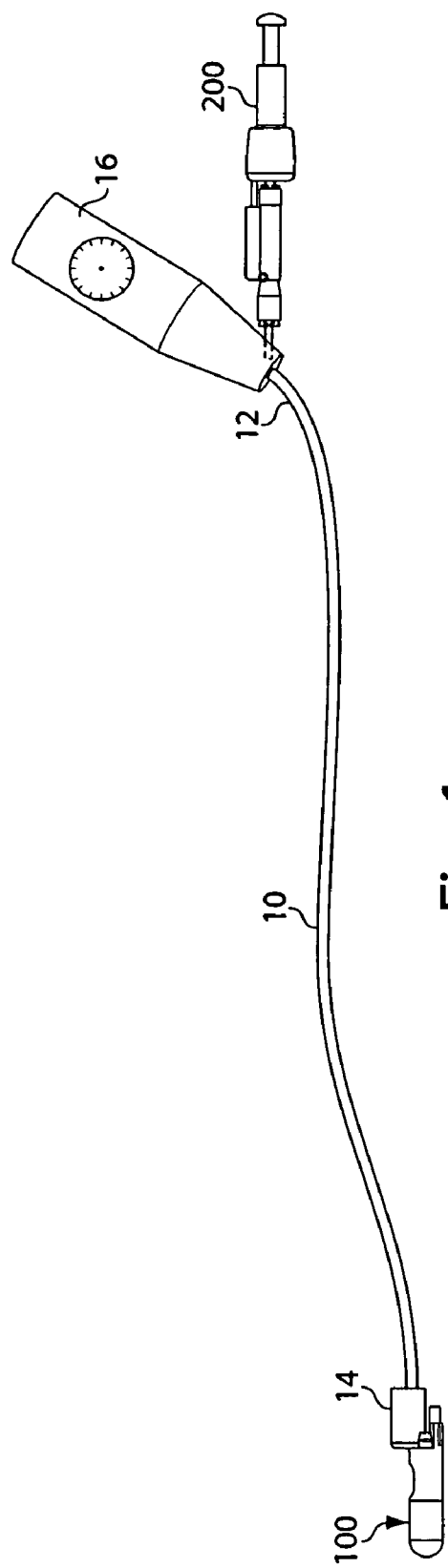
FIG. 1 is a diagrammatical representation of an endoscope carrying the suturing system of the present invention.

FIGS. 1-3B show the components of the single intubation, multi-stitch endoscopic suturing system. In FIG. 1 is shown the endoscopic suturing device comprising a suturing capsule 100 that is releasably secured to the distal end 14 of an endoscope 10. The capsule 100 is operated by a control handle 200 releasably mounted to the proximal end 12 of the endoscope 10 adjacent to the endoscope control handle 16. The suturing system operates to place sutures through tissue at internal locations within a patient accessible by an endoscope.

Figure 2:
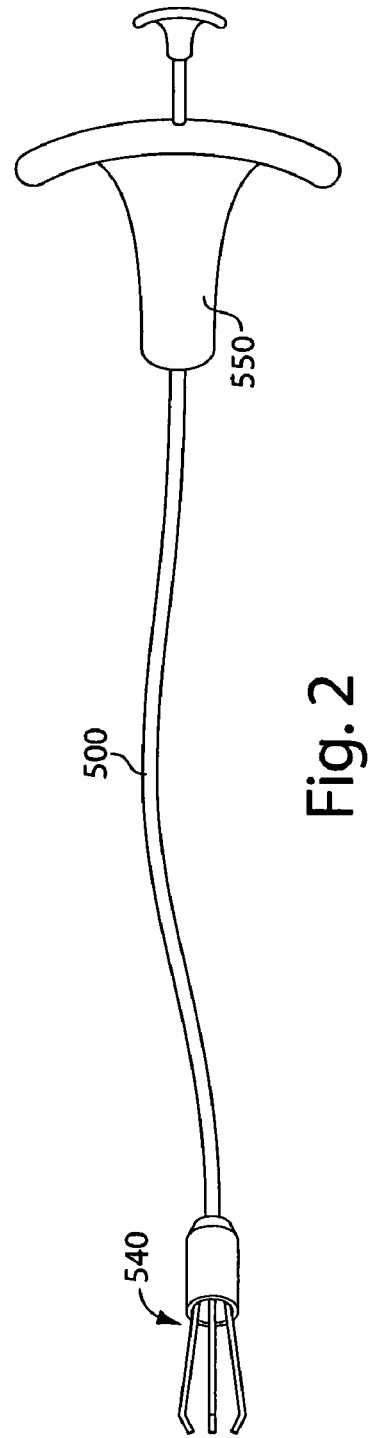
FIG. 2 is a diagrammatical representation of the suture lock delivery device of the present invention.
Figure 3A:
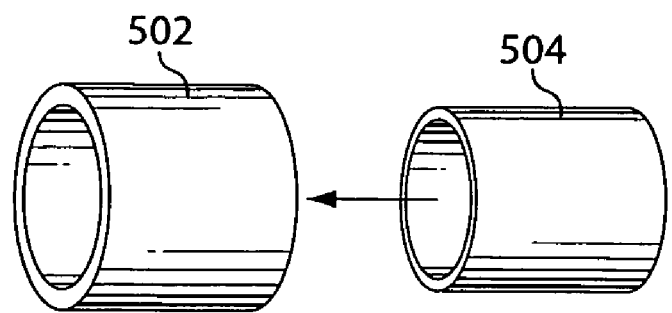
FIGS. 3A and 3B are diagrammatic representations of a ring and plug suture lock.
Figure 3B:
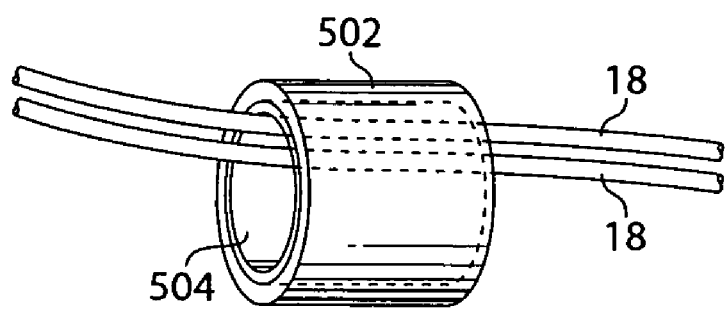

FIG. 2 shows another component of the single intubation system: a suture lock delivery device 500, which is sized to extend through the working channel of an endoscope. Extended through an endoscope, the distal operating end 540 of the delivery device extends outside of the distal end 14 of an endoscope while the control handle 16 extends from the proximal end 12 of an endoscope so that it may be operated by a user. The delivery device 500 is configured to apply suture lock devices such as shown in FIGS. 3A and 3B. The suture locks of FIGS. 3A and 3B comprise a ring 502 to which is inserted a plug 504 sized to become frictionally engaged in the opening of the ring. As shown in FIG. 3B when sutures 18 are passed through ring 502, insertion of the plug 504 causes the suture to become trapped and locked between the outer surface of the plug and the inner surface of the ring, effectively securing the suture leads 18 in the tissue. A comprehensive discussion of suitable suture lock devices including presentation of alternate suitable examples of such suture locks is presented in pending U.S. application Ser. Nos. 10/220,413 and 10/275,534, incorporated by reference herein. Although each of the components shown in FIGS. 1-3B may be used separately in endoscopic suturing procedures and provide utility for their intended purpose, use of the components together enables endoscopic suturing providing multiple stitches to a plurality of internal locations and securing them with a single intubation of an endoscope into a patient.

Suturing Capsule

Figure 4:
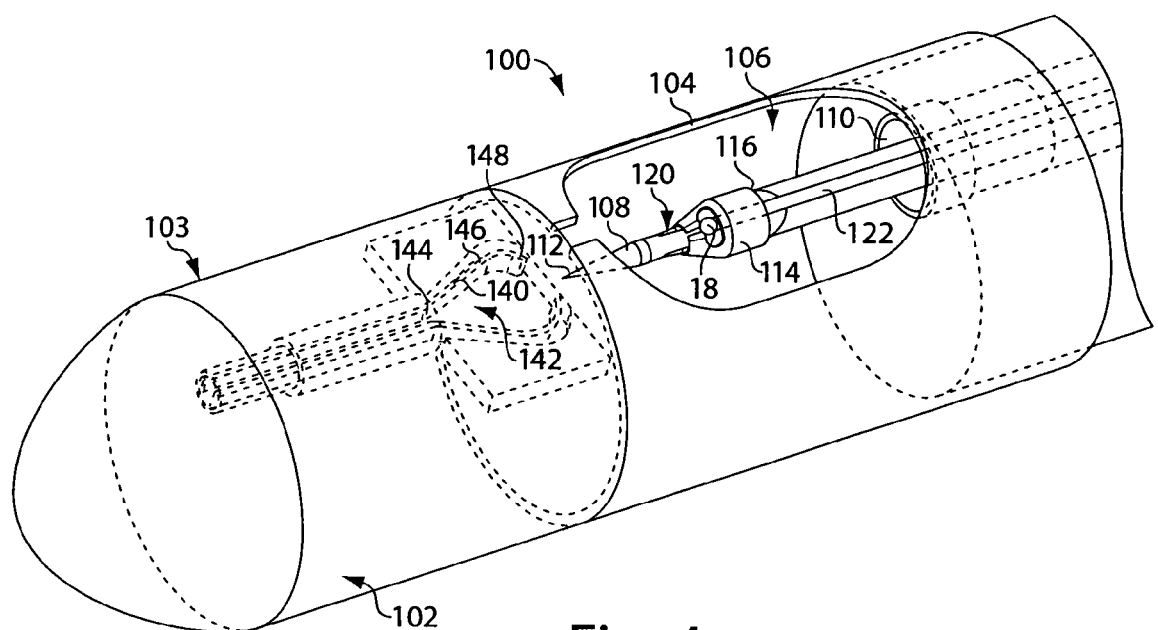
FIG. 4 is an isometric transparent view of a suturing capsule.

FIG. 4 is an isometric transparent view of the suturing capsule 100. The capsule 100 comprises a cylindrical body 102 having an atraumatic shape to reduce the chance of trauma to internal tissues during operation. The capsule is similar in configuration and operation to that disclosed in U.S. Pat. No. 5,792,153 discussed above. The capsule includes a suction port 104 open to a tissue suction chamber 106 into which tissue portions to be sutured may be collected under vacuum introduced into the chamber. The capsule is configured to receive a needle 108 slidable through a needle track 110 formed through the capsule. The needle may be a solid stainless steel shaft with a sharpened distal tip 112 and be joined at its proximal end to a pusher shaft 184 that extends proximally from the suture capsule, through the working channel of the endoscope. The pusher shaft exits the proximal end of the endoscope where it may be joined to and manipulated by a control handle as will be discussed below. When the needle is moved longitudinally through the needle track, it traverses the suction chamber 106 so that tissue suctioned into the chamber will be penetrated by the distally advancing needle.

The needle 108 carries an annular suture tag 114 that fits closely about the outside surface of the needle. The tag has proximal and distal ends, and can have a decreasing taper from its proximal end to its distal end to create a low profile as the needle and suture tag are advanced distally through tissue. Joined to the suture tag is one end of a suture 18 that will be carried through a suctioned tissue portion when the needle carrying the suture tag 114 is advanced distally. The suture may be attached by passing through an opening in the tag and forming a enlarged tip or knot on the suture so that it is too large to fit back through the tag. The suture tag is releasably and selectively secured to the outside surface of the needle by a suture tag lock 120. The suture tag lock is also remotely operable from the proximal end of the endoscope by a suture tag lock shaft 122 that is slidable over the needle control shaft and needle 108.

Full distal advancement of the needle places the suture tag 114 within the confines of a suture tag catch 140. After penetrating a captured tissue portion and entering the suture catch, the suture tag lock 120 may be released and the needle withdrawn proximally leaving behind the suture tag 114 in a nest area 142 of the suture tag catch. The suture tag catch comprises a Y-shaped structure 144 having two resilient arms 146. The resilient arms are joined together at the base of the Y-shaped member 144 and extend longitudinally in a proximal direction terminating in a free-end having an inwardly curved prong 148 to catch the proximal facing surface 116 after the tag 114 has entered the nest 142. After capture and release of the suture tag into the suture tag catch 140, the needle may be withdrawn proximally and the tissue released from the suction chamber 106 with a suture 18 left passing through the tissue and having one end joined to the captured suture tag at the distal end 103 of the capsule and the other end of the suture extending into the needle track 110, through the working channel of the endoscope and exiting the proximal end of the endoscope.

Figure 5:
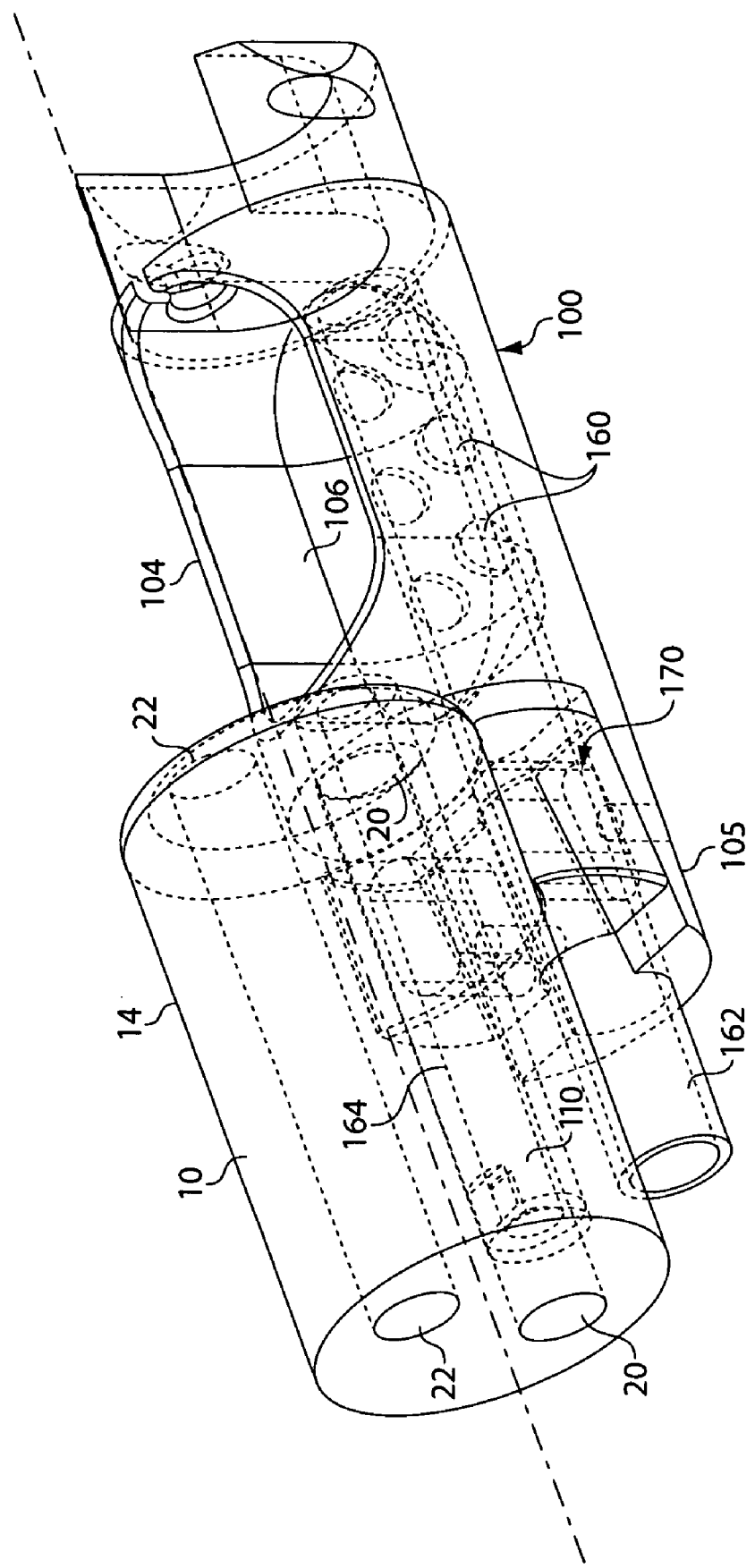
FIG. 5 is an isometric transparent view of a suturing capsule shell attached to the distal end of an endoscope.

FIG. 5 shows another isometric view of a suturing distal end of an endoscope 10 having attached to it a shell of a suturing capsule 100 with internal components removed. Suction port 104 opens to the suction chamber 106. At the bottom of the suction chamber are several aspiration ports 160, shown in phantom, through which negative pressure is introduced to the suction chamber to selectively capture a tissue portion to be sutured. The vacuum is introduced to the aspiration ports 160 through vacuum tube 162 extending proximally from the capsule 100 and joined to a separate vacuum line (not shown) that extends along the exterior of the endoscope 10.

The cutaway view of the distal end 14 of the endoscope 10 shown in FIG. 5 shows a working channel 20 and viewing channel 22. Other channels that may pass through the endoscope such as for light source or for a liquid cleaning source have been omitted for clarity. The capsule 100 is joined to the distal end of the endoscope by a proximally extending guide tube 164 (shown in phantom) inserted into the working channel 20 of the endoscope. The guide tube 164 is rigid and extends proximally from the proximal end of the capsule 105 of the capsule to protrude a short distance into the working channel 20 of the endoscope. The guide tube 164 is open to receive the needle track 110 assembly through which the needle slides during operation.

Figure 6:
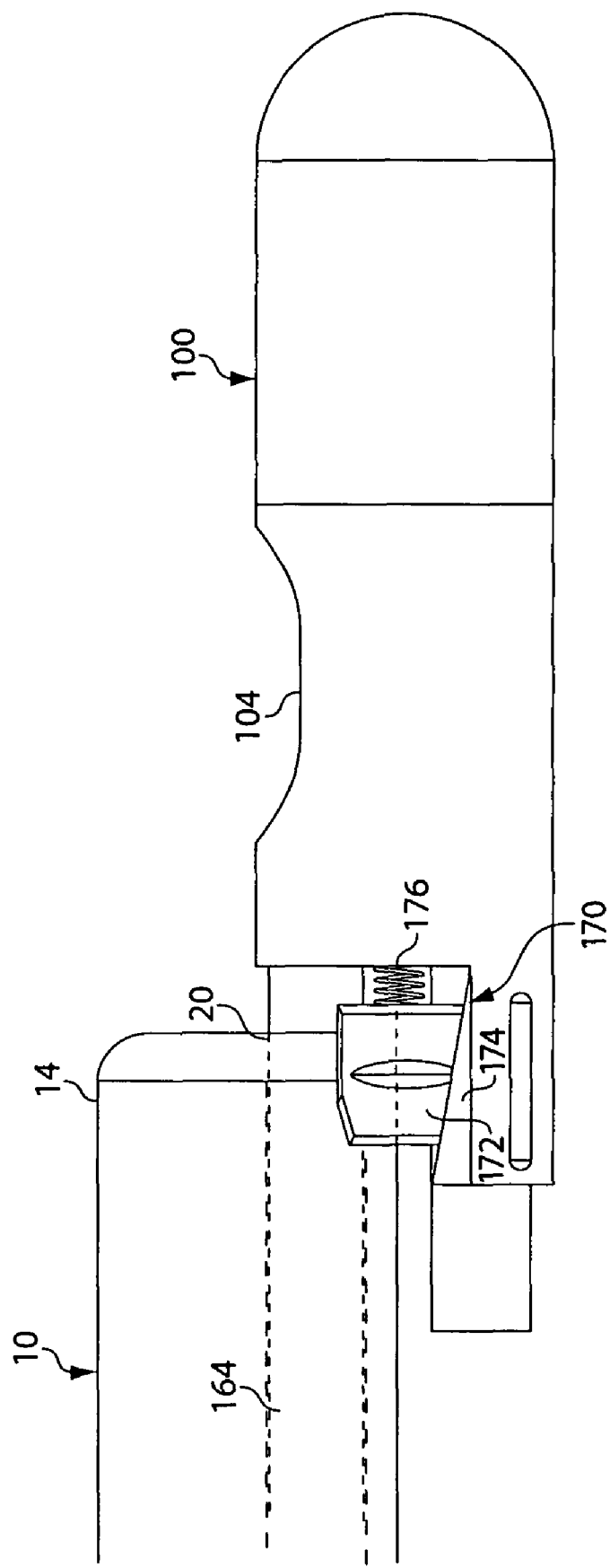
FIG. 6 is a side view of a suturing capsule attached to the distal end of an endoscope by a reverse wedge attachment mechanism.

As shown in FIGS. 5 and 6, the capsule may be secured to the distal end 14 of the endoscope by a reverse wedge securement mechanism 170. A reverse wedge and an endoscopic accessory securement mechanism is fully described in pending U.S. application Ser. No. 10/275,226, filed Feb. 11, 2003, and titled "Endoscopic Accessory Attachment Mechanism", which is incorporated herein by reference in its entirety. It is also disclosed in published PCT application WO 01/87144. The basic elements of the reverse wedge securement mechanism include a wedge component 172 slidable on a ramp surface 174 to become wedged between the distal end of the endoscope 14 and the ramp surface 174 as it slides up the ramp. Leverage against the distal end of the endoscope is maintained by the presence of the guide tube 164 through the working channel 20. Return spring 176 maintains force against the wedge member 172 so that it is biased upward along the ramp surface 174 to maintain wedge contact with the endoscope.

Figure 7A:
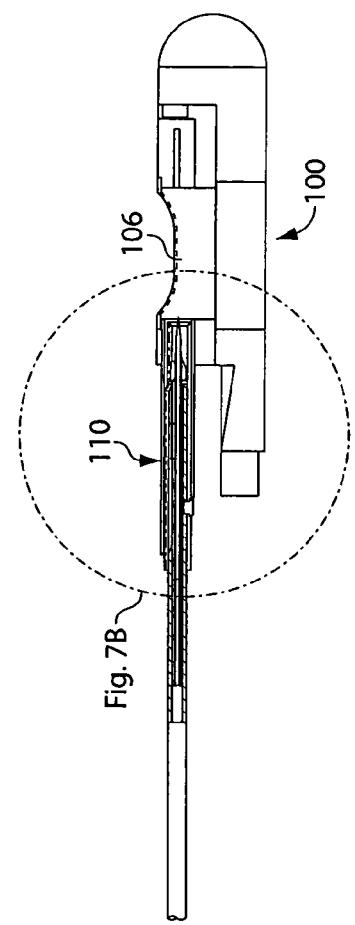
FIG. 7A is a side view of a suturing capsule of the present invention indicating an area A of detail that is shown on FIG. 7B.
Figure 7B:
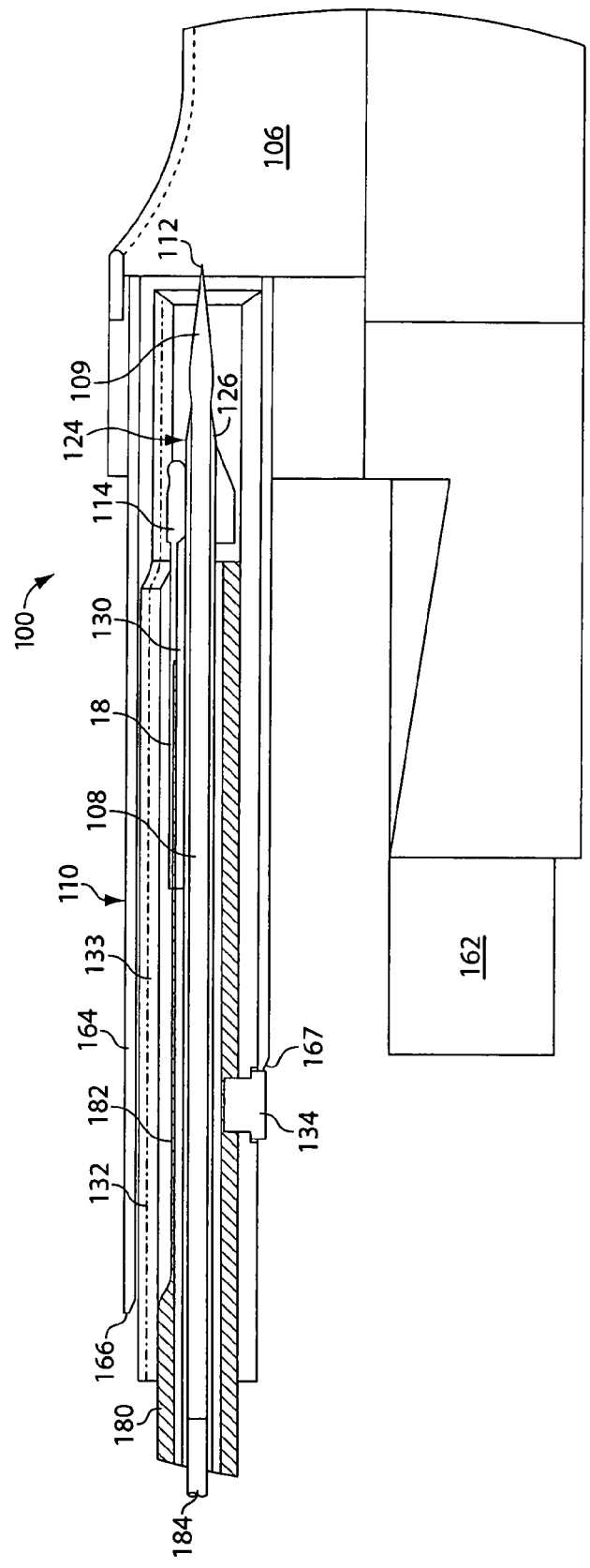
FIG. 7B is a detail view of area A shown in FIG. 7A.

FIG. 7A is a side view of the suture capsule 100 not mounted on an endoscope and indicating an area of detail of the needle track 110 presented in FIG. 7B. The needle track 110 resides in the guide tube 164 extending proximally from the capsule 100 as shown in FIG. 7B. Guide tube 164 is the outermost tubular structure of the needle track and as mentioned above provides a mounting structure for engaging the internal surface of the working channel of an endoscope to securely mount the capsule. The guide tube may be formed as part of the capsule and therefore formed of the same rigid material such as stainless steel. The proximal end of the guide tube 166 has a beveled cut across its opening that tapers downward to enable circumferential alignment of the control components, including other needle track components as they are advanced from the proximal end of the endoscope through the working channel into the capsule 100 as will be explained below.

Most of the components of the needle track are contained within an outer sheath 180 that extends the full length of the working channel of the endoscope, from the control handle at the proximal end to the guide tube 164 of the capsule 100. The outer sheath 180 and the needle track components associated with it are advanced through the proximal end of the endoscope into the guide tube 164 after the capsule has already been mounted to the distal end of the endoscope. The guide tube may be made of any strong but flexible material such as the polymer polyetheretherketone (PEEK). The outer sheath has a flattened portion 182 along its distal portion that resides within the guide tube 164 after assembly to permit passage of the suture 18 so that it may continue proximally through the working channel of the endoscope and out the proximal end without being required to extend through the outer sheath 180.

The innermost component of the needle track is the needle 108. The needle may have an enlarged spear-shaped distal end 109 to interact with the suture tag lock as will be discussed later. The distal tip 112 of the needle is sharpened pierce tissue and the proximal end of the needle is joined to a pusher shaft 184 that extends to the control handle mounted at the proximal end of the endoscope.

Slidable over the shaft of the needle 108 over its entire length is a locking sleeve 124 of the suture tag lock system 120. The locking sleeve 124 is a stainless steel hypotube of approximately 0.016 inch I.D. sized to fit closely over the outside surface of the needle shaft, which measures approximately 0.0155 inch. The locking sleeve is also adjoined to the control handle at the proximal end of the endoscope. The distal end of the locking sleeve has two longitudinal notches extending proximally from the distal tip of the sleeve to a depth of approximately 0.080 inch to define two locking splines 126. As described more fully below, when the locking sleeve is advanced distally relative to the needle, the locking splines ride over the enlarged spear shape 109 of the needle 108, become splayed radially outward to create locking surfaces 128 that prevents distal sliding of the suture tag 114.

Outside of the locking sleeve is positioned a stiffener sleeve 130. The stiffener sleeve, formed from a rigid material such as stainless steel hypotubing extends over the needle and locking sleeve only along their distal portions, contained within the guide tube 164. The locking sleeve helps to insure that the needle remains parallel to the longitudinal axis of the endoscope during longitudinal sliding movement within the capsule 100.

External to the outer sheath 180 is bonded an outer shroud 132, formed from a semi-rigid polymer material such as PEEK that serves to additionally maintain the alignment of the needle and needle track assembly 110 within the guide tube 164 of the capsule 100. The outer shroud 132 serves as a bushing to absorb the space between the outer sheath 180 and the inside surface of the guide tube 164. The top of the shroud has a longitudinal slot 133 extending the full length of the shroud to permit passage of the suture 18 without interference as it slides with the suture tag 114 and needle 108. The bottom of the shroud 132 receives a transversely inserted alignment pin 134 that protrudes slightly from the exterior surface of the shroud. The protrusion of the alignment pin 134 interferes with the slash cut of the proximal end 166 of the guide tube. When the outer sheath and needle track assembly 110 are advanced distally through the working channel of an endoscope during assembly of the system, the guide pin catches on the distal end 166 of the guide tube 164 and further distal advancement of the outer sleeve and shroud cause the alignment pin to follow the slash cut and rotate the assembly as needed so that the alignment pin becomes bottomed out at the distal most portion of the slash cut 167. This positioning of the alignment pin insures that the needle track assembly 110 is aligned circumferentially with the guide tube 164 and suturing capsule 100 so that the suture does not become twisted or tangled during operation of the needle and tag during suturing.

Figure 8:
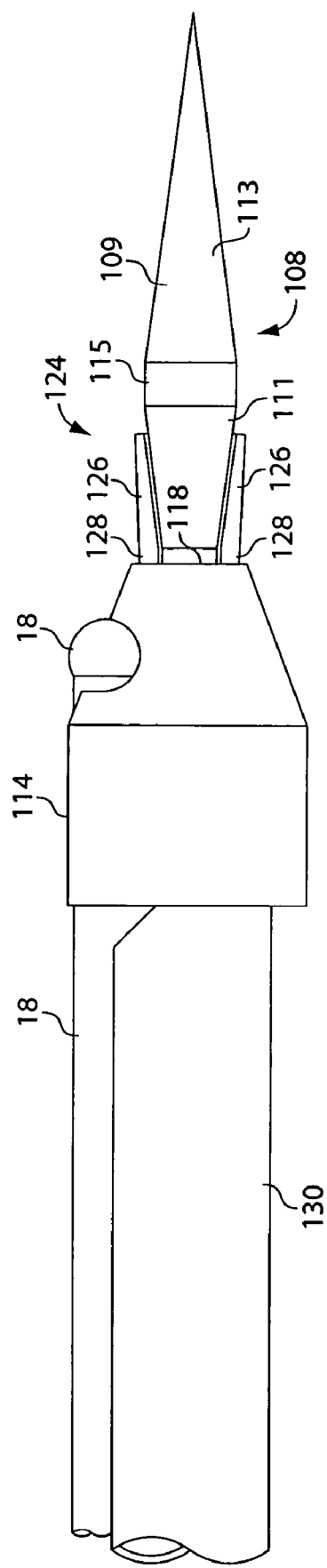
FIG. 8 is a side view of a needle and suture tag locked on the needle by a suture tag lock device.

FIG. 8 shows a side view of the needle 108 carrying a suture tag 114 locked from distal sliding movement by a suture tag lock 120. The suture tag 114 is annular, defining a through bore that is sized to closely fit over the locking sleeve 124. The stiffening sleeve 130, adhered to the locking sleeve 124 terminates just prior to the distal end of the locking sleeve leaving a carrying space over which the suture tag 114 may reside during delivery on the needle 108. The diameter of the stiffener sleeve 130 is slightly greater than that of the through bore of the suture tag 114 to provide a backstop to prevent the suture tag from sliding proximally relative to the needle and locking sleeve 124.

As described above, the distal end of the needle is formed to have spear shape 109 formed by a proximal increasing barrel taper 111 converging with a distal increasing barrel taper 113 to create an increased diameter portion 115 of the spear shaped tip 109.

When the needle is withdrawn proximally into the locking sleeve 124 of the suture tag lock 120, the locking splines 126 ride up over the proximal barrel taper of the needle causing them to become splayed radially outward. The splayed splines 126 effectively increases their profiles to an extent such that the through bore 118 of the suture tag cannot fit over it, which locks the suture tag 114 in place on the needle.

To release the suture tag so that it may slide distally relative to the needle as would be desired when leaving the tag in the suture tag catch 140 during suturing procedure, the needle 108 is moved distally relative to the locking sleeve 124. Movement of the needle distally relative to the locking sleeve moves the proximal barrel taper to the reduced diameter of the needle shaft 107 and the splines 126 resiliently conform to the reduced diameter, returning radially inward to define a smaller profile over which the through bore 118 of the suture tag 114 may pass. The enlarged diameter portion 115 of the needle, without the added thickness of the two splines 126 from the locking sleeve 124, also defines a profile over which the through bore 118 of the suture tag 114 may pass freely.

Figure 10:
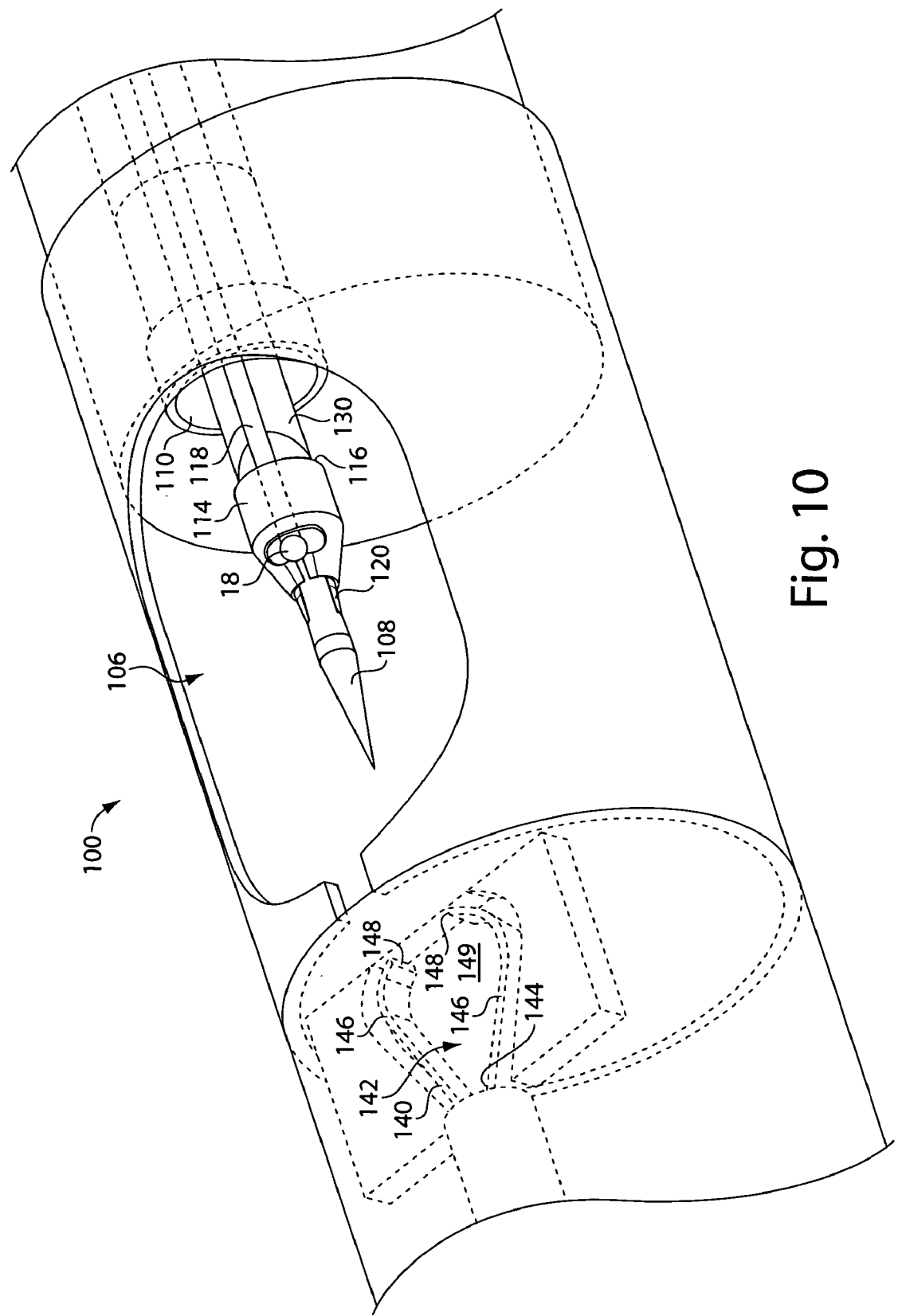
FIG. 10 is an isometric transparent view of the suturing capsule with the needle and suture tag advancing distally to the suture catch.

An isometric transparent view of the capsule 100 showing the suture tag catch 140 is shown in FIG. 10. In the figure, the needle is approaching the suture tag catch 140 while the suture tag 114 is locked in position on the needle by suture tag lock 120. The needle traverses the suction chamber 106 on its way to deliver the tag to the suture tag catch 140, which is positioned on the distal side of the suction chamber 106. Tissue is not shown in the figure for clarity. The suture tag catch 140 comprises a Y-shaped member 144 having two resilient arms 146 joined together at the base of the Y and having free ends that terminate in inwardly facing prongs 148 to catch the proximal face 116 of the suture tag 114. The area around the resilient fingers 146 is configured to closely fit the cylindrical tapered tip of the suture tag 114 to hold it securely and defines a nest 142 where it will be securely maintained during its retention in the catch.

Figure 11:
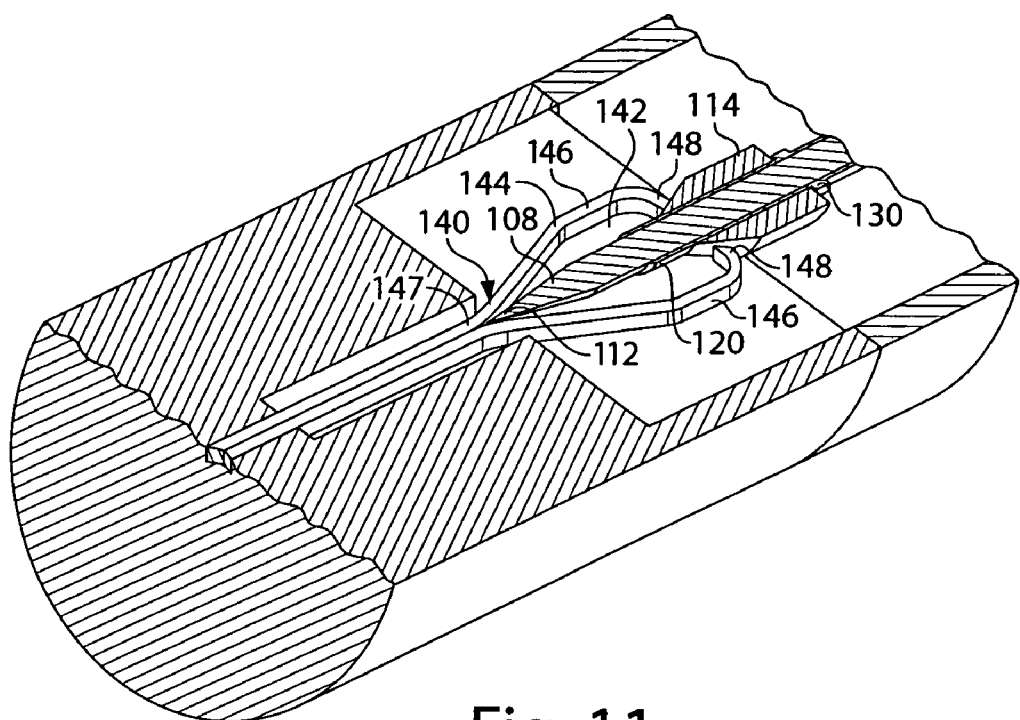
FIGS. 11-14 illustrate various stages of the suture tag and needle entering the suture tag catch in the capsule.

In operation, the suture tag catch 140 operates to retain the tag by the steps described below with references to the sectional views presented in FIGS. 11-14. In FIG. 11, the needle is shown advancing into the Y-shaped member 144 such that its distal tip 112 is within the nest area 142 but the suture tag 114 has yet to pass the inwardly projecting prongs 148 of the arms 146. As shown in the sectional views of FIGS. 11 and 12, as the needle proceeds distally, the sharpened distal tip 112 of the needle enters the base 147 of the Y-shaped member 144 causing the resilient arms 146 to be spread apart to assist with entry of the suture tag 114 into the nest 142 past inwardly projecting prongs 148. During this stage, the needle is advanced distally relative to the locking sleeve 124 of the suture tags 124 of the suture tag lock 120 to release the suture tag lock and permit the needle to be slipped out from the suture tag during its proximal withdrawal stroke.

Figure 12:
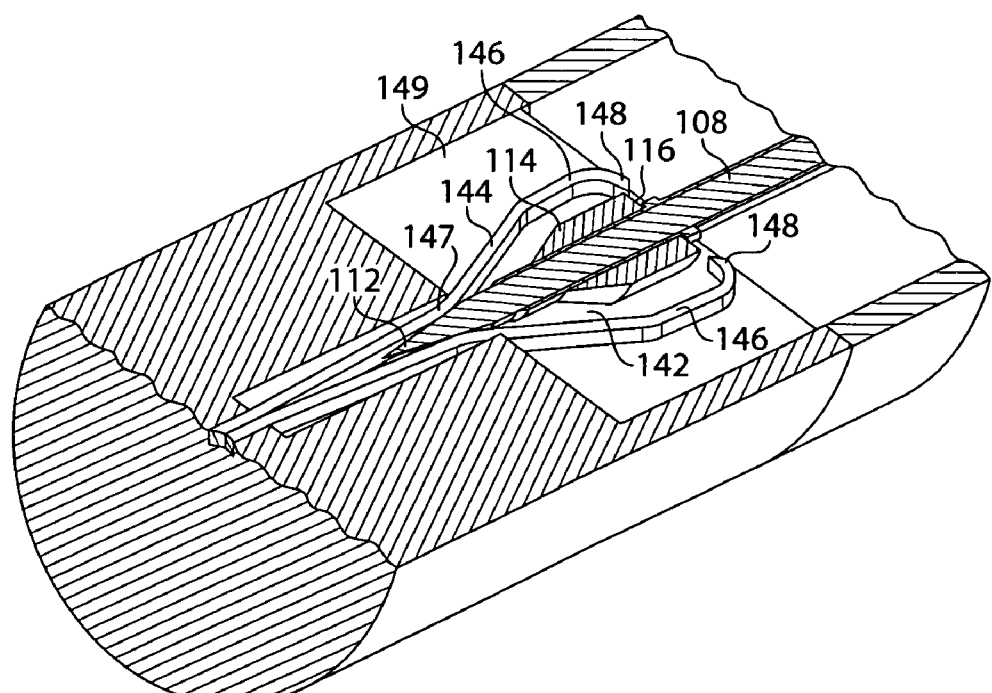
Figure 13:
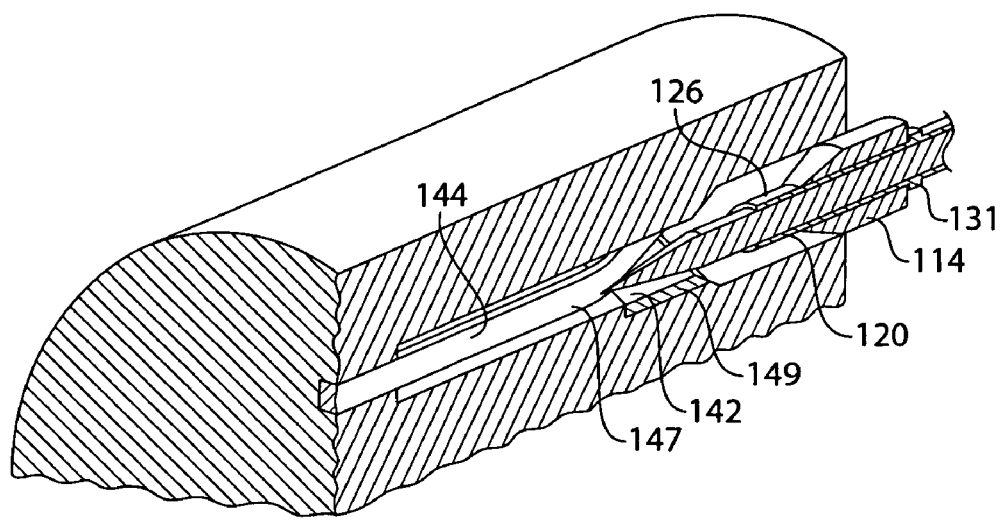

After seating of the suture tag 114 in the nest 142, as shown in FIG. 12, the beginning of the proximal withdrawal stroke may find the resilient arms 146 at the suture tag catch still slightly open due to the presence of the sharpened tip of the needle 112 in the base 147 of the Y-shaped member 144. Proximal withdrawal of the needle in this condition may cause the suture tag to stick to the needle due to residual frictional forces and thus not be captured by the prongs 148 against the proximal 116 of the suture tag. Accordingly, a frictional rub strip 149 may additionally be provided through the nest area 142 to provide a frictional surface on the capsule in the nest area that serves to hold the tag in the nest even if the resilient arms 146 have not yet sprung back to close around the proximal face 116 of the tag (FIG. 12). The frictional rub strip may be a polymer insert.

Figure 14:
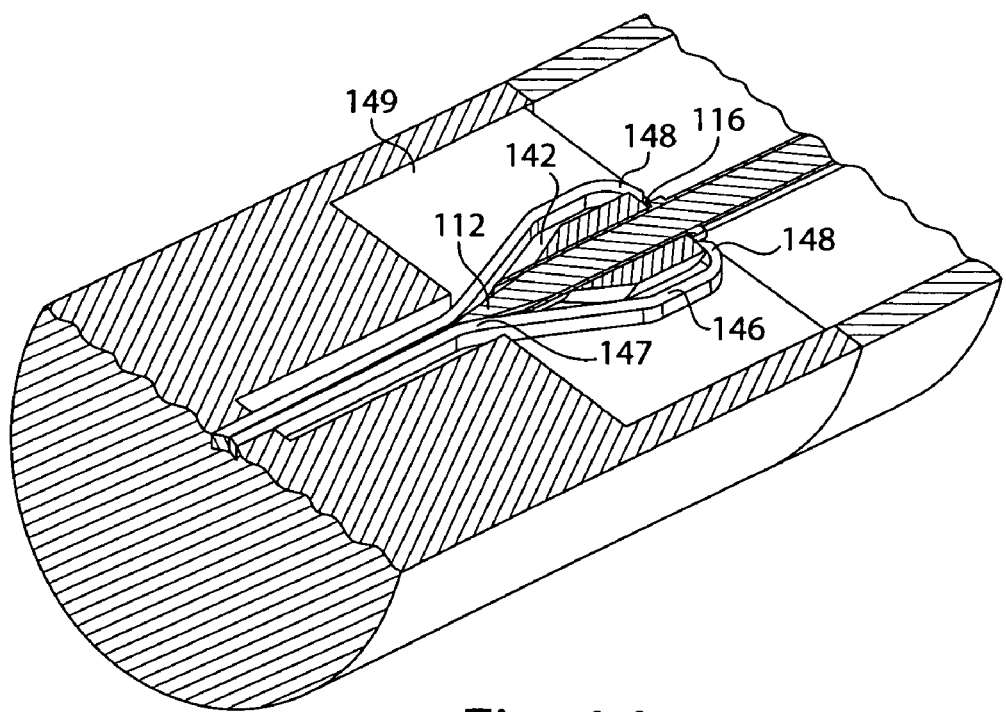

After slight proximal withdrawal of the needle such that the sharpened tip 112 is removed from the base of the Y 147, the arms 146 will close around the suture tag 114 so that prongs 148 engage the proximal face 116 of the tag (FIG. 14). As shown in the overhead view of FIG. 14, after the needle 108 is withdrawn proximally, the tag remains captured by the suture tag catch 140 within the nest 142. In the captured position, resilient arms 146 return to a closed position such that inwardly projecting prongs 148 engage the proximal face 116 of the suture tag 114 holding it from proximal movement out of the nest. The nest 142 also serves to retain the tag 114 in alignment, so that it does not move distally or laterally during the suturing procedure so that when the needle returns to pick up the tag, it will be in alignment with the through bore 118 of the suture tag 114.

Figure 15:
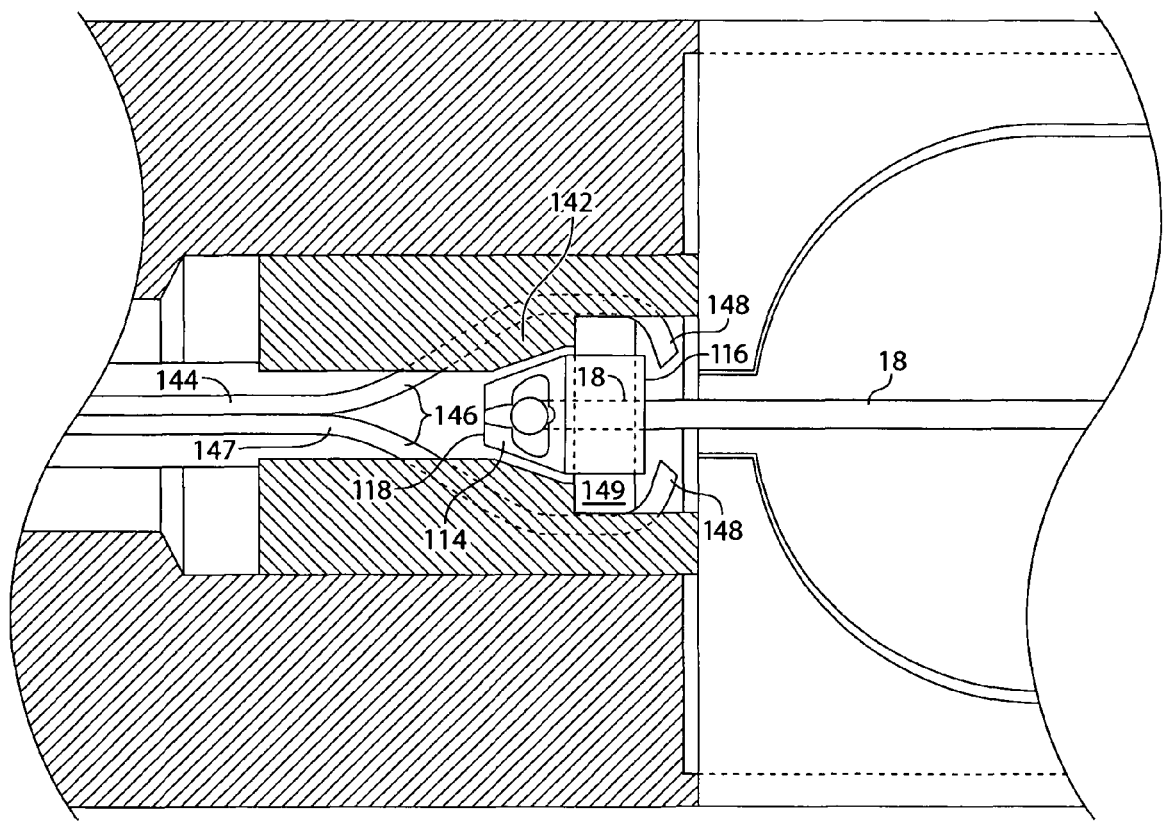
FIG. 15 is an overhead view of the suture tag catch with a suture tag captured.

The steps for retrieval of the tag are substantially the reverse of the steps illustrated for delivering the tag to the suture catch. In returning to retrieve the tag, the needle is advanced distally again into the area of the suture tag catch while in the unlocked position (shown in FIG. 10). After the needle has bottomed out at the base of the Y 147, the needle may be slid proximally relative to the suture tag lock 120 so that the locking splines 126 ride up on the proximal barrel taper 111 of the needle creating the locked condition shown in FIG. 15. In the locked position, a proximal withdrawal for supply to the needle will overcome the restraining force presented by the prongs 148 against the proximal face 116 of the tag, causing the resilient arms 146 to deform slightly and permit passage of the tag 114 along with the needle in its proximal withdrawal stroke.

Suture Capsule Control Handle

Figure 16:
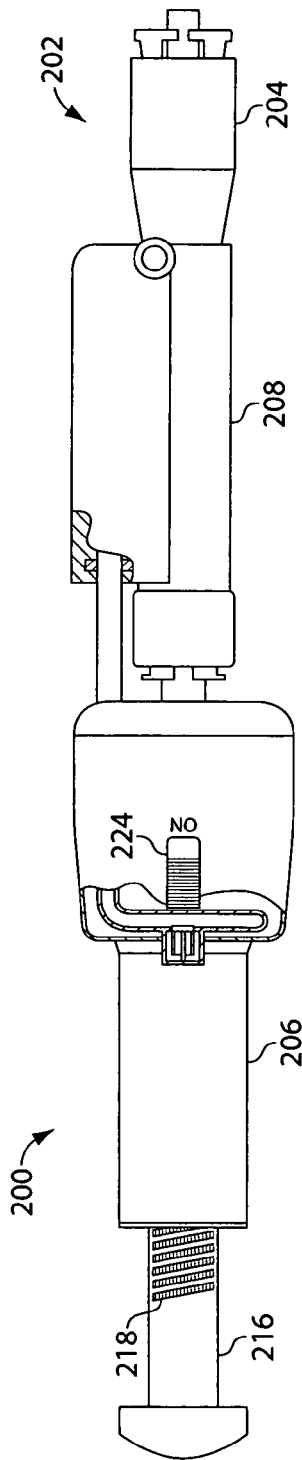
FIG. 16 is a side view of a suturing capsule control handle.

A side view of a suitable suture control handle 200 is shown in FIG. 16. Although one example of an endoscope is described herein as the illustrative embodiment, it should be understood that other configurations for the control handle may be suitable to operate the suture capsule as required. The control handle must provide means that permit the operator to drive the needle pusher shaft and the suture tag locking sleeve 124 longitudinally and relative to each other to operate the capsule through the steps outlined above. Additionally, the handle should be releasably securable to the proximal handle assembly of an endoscope 210 at the opening port to the working channel of the endoscope through which the needle pusher shaft and suture tag locking sleeve will be inserted. Additionally, it may be preferable to route the vacuum source line through the control handle so that the operator can selectively introduce and discontinue vacuum as appropriate to capture and release tissue during the suturing procedure. Alternatively, the control handle can involve a vacuum control switch which includes an interlock feature to prevent longitudinal movement of the handle control members until a pre-established vacuum pressure is achieved in the suction chamber.

The control handle shown in FIG. 16 includes a collet 204 at its distal end 202 for connection to an endoscope control handle 210 at the proximal end 12 of an endoscope 10. The collet screws onto the port normally provided for the working channel of most endoscopes while permitting a through hole through which the needle pusher shaft 184 and suture tag lock sheath 124 may pass in slidable fashion.

The control handle also comprises a vacuum switch housing 208 as joined to the collet 204 and directs the vacuum line assembly through the body of the handle 200. The handle further comprises a main body portion 206 housing the components that translate longitudinal movement of plunger 216 into the segmented longitudinal movements of the needle pusher shaft 184 and suture tag locking sleeve 124. Visual markings 218 may be placed on the plunger to indicate to the user (by showing remaining bars of the marker not inserted into the main body 206) at which stage of deployment the control handle is in a given moment.

Figure 17:
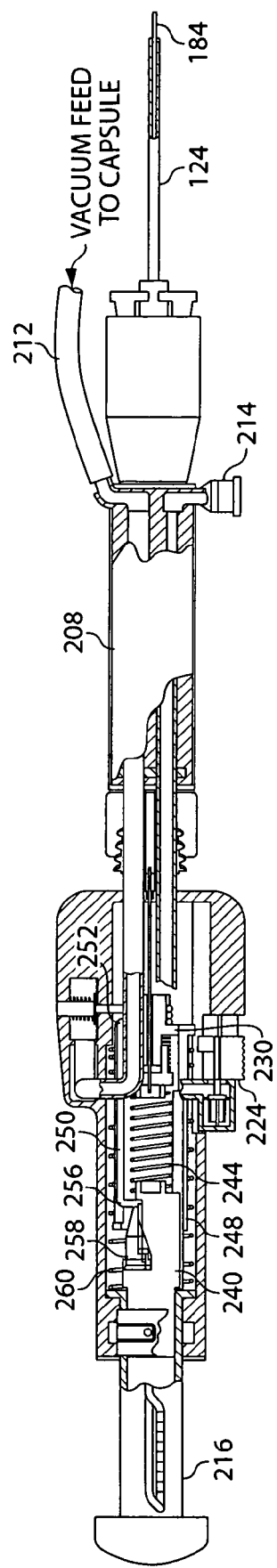
FIG. 17 is a sectional view of a suture control handle.
Figure 18:
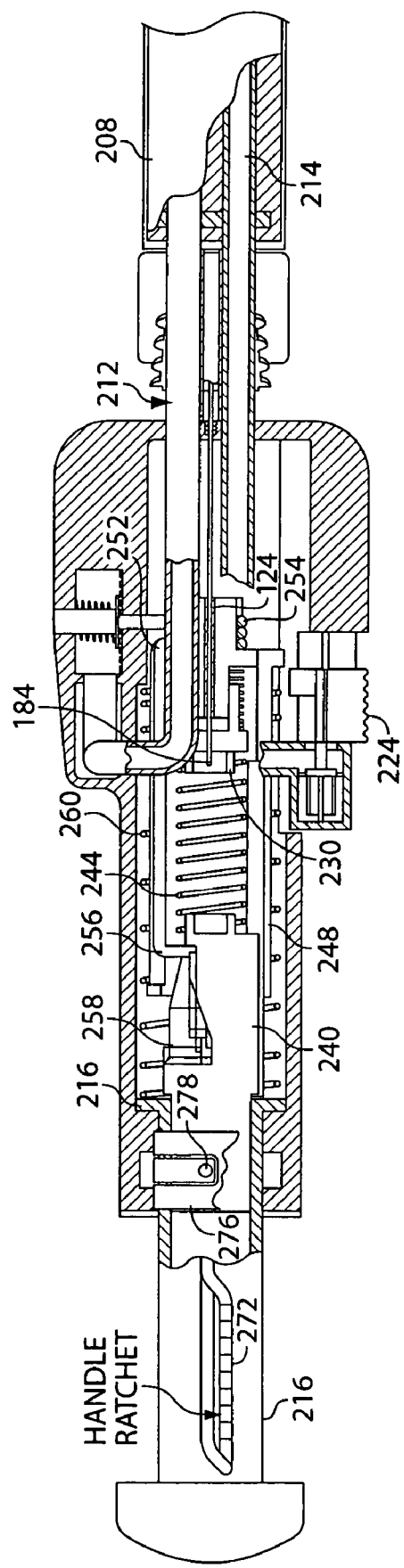
FIG. 18 is a detailed sectional view of the control handle of FIG. 17.

FIG. 17 presents a sectional view of the main body 206 of the control handle showing the mechanism that translate longitudinal movement of the plunger 216 to movement of the needle and suture tag lock assembly. FIG. 18 is a detailed sectional view of the main body 206 shown in FIG. 17. It is noted that the handle position shown in FIGS. 16-18 represents the initial state of the system in which the needle and tag remain in the needle track 110 on the proximal side of the suction chamber 106 prior to the first suture stroke.

FIGS. 17, 18 and 19A show a sectional view of the control handle in its initial position. The plunger 216 is engaged with both a locking sheath carrier 220 which is joined to the suture tag locking sleeve 124 and engaged with a needle carrier 230 that is engaged with the needle pusher shaft 184. The plunger engages the needle carrier 230 by pushing against plunger carrier 240 pushing against needle deployment spring 244, which is in engagement with the needle carrier 230 when the plunger is pushed distally relative to the main body 206 of the handle. When the plunger carrier 240 is slid distally, it slides through main carrier 248 to keep it in longitudinal alignment within the handle.

Figures 20, 21:
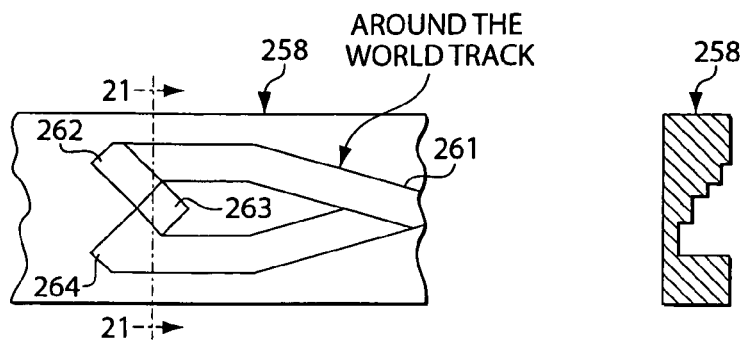
FIG. 20 is an overhead view of an around-the-world pawl track.
FIG. 21 is a sectional view taken along the line A-A shown in FIG. 20.
Figure 22:
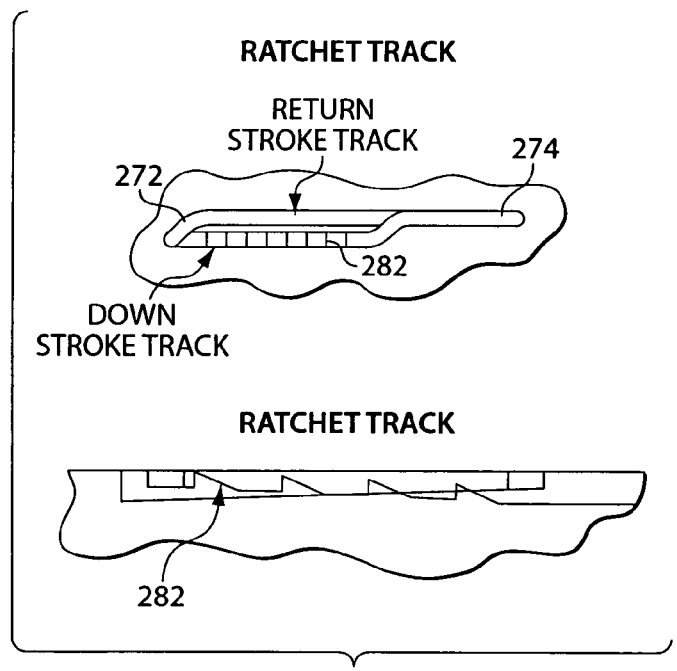
FIG. 22 is an illustration of a ratchet pawl track.
Figure 23:
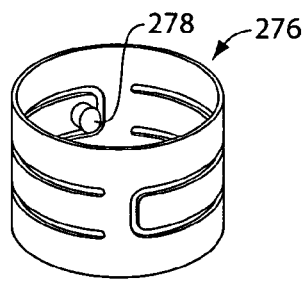
FIG. 23 is an isometric view of a cylindrical ratchet pawl.

The plunger 216 is also in engagement with the locking sheath carrier 220 by engagement of a pawl arm 250. The distal end 252 of the pawl arm engages the locking sheath carrier 220 directly by contact with a small spring 254. The pawl arm extends proximally over the needle deployment spring such that its proximal end 256 engages an around-the-world pawl track 258 retained in the plunger carrier 240 as shown in detail in FIG. 19B. An overhead view of the pawl track 258 is shown in FIG. 20 with a sectional view presented taken along the line A-A presented in FIG. 21. The around-the-world track is three-dimensional such that as the proximal pawl arm travels in the track, its elevation changes to guide the pawl fully along the track in one direction despite only input of longitudinal movement from the plunger.

A handle return spring 260 surrounds the entire assembly of the plunger carrier 240 needle deployment carrier and pawl arm so that a proximal resilient force is always present against the plunger 216 throughout deployment. An additional feature may be added to the handle to insure that a partially deployed needle is not withdrawn proximally prematurely.

A plunger ratchet assembly 270 insures that the plunger travels only in a distal direction until it has reached its maximum distal stroke length before permitting proximal return of the plunger. This feature insures that the operator must complete the distal delivery stroke of the needle to insure that it is fully released in the proximal direction so that no attempt is made to withdraw the suture capsule assembly while the needle is partially or fully inserted through a suctioned tissue portion. The ratchet assembly 270 comprises a ratchet track 272 shaped as a parallelogram with a distally extending straight track portion 274. A cylindrical ratchet pawl assembly 276 with projecting pawl arm 278 configured to ride within the tract during longitudinal movement of the plunger 216 is secured in a ratchet pawl recess 280 formed in the main body 206 of the housing. Ratchet teeth 282 are formed on one side of the parallelogram ratchet track 272 so that ratchet action occurs only during distal movement of the plunger 216 during the period in which the needle will be traversing the suction chamber of the capsule. The linear portion of the ratchet track 274 represents distal travel of the needle prior to traversing the suction chamber. The side of the parallelogram without ratchet teeth represents travel by the ratchet pawl arm 278 during the proximal return stroke of the plunger 216, which need not be controlled by ratchet action for safety reasons.

Operation of the control handle and the corresponding movement of the components of the suturing capsule will be described in connection with FIGS. 17, 18, 19A, 24 and 25. From the initial position shown in FIGS. 17, 18 and 19A, the user begins operation of the control handle by first turning on the vacuum supply switch 224 (FIG. 16) to open the vacuum input line 214 (connected to a supply of vacuum) to the vacuum output line 212 that extends along the endoscope to the suturing capsule 100. The introduction of vacuum causes tissue to be sucked into the suction chamber 106 and the suturing process may be initiated.

Figure 24:
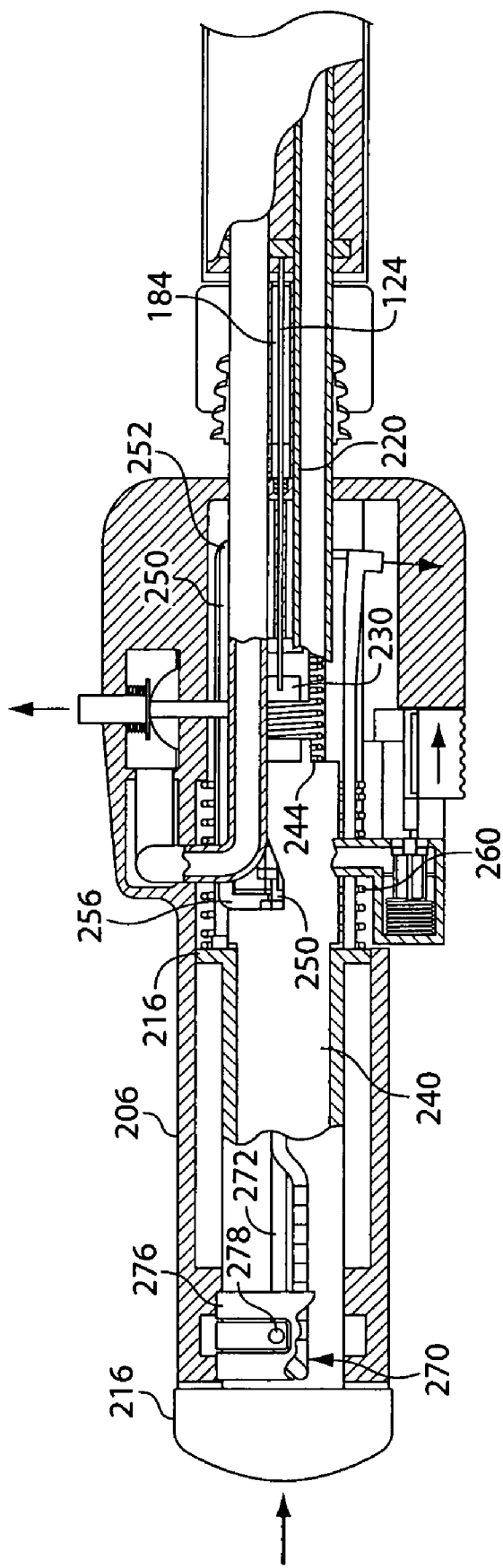
FIG. 24 is a sectional view of the control handle fully advanced in the distal direction.

From the initial position shown in FIGS. 17, 18, and 19A of the handle, the user depresses the plunger 216 fully as shown in FIG. 24 to drive the needle distally, traversing the suction chamber 106 and driving the suture tag 114 into the suture catch assembly 140 as shown in FIG. 14. Depression of the plunger 216 serves to push the plunger carrier 240 distally through the handle, compressing needle deployment spring 244 and following compression of that spring, moving the needle carrier 230 distally by a stroke length equivalent to that traveled by the plunger 216. The locking sheath carrier 220 is also moved distally during the full distal stroke of the plunger 216 although by a magnitude slightly less than that achieved by the needle carrier 230 due to the travel of pawl 256 and pawl track 258 during the distal movement of the plunger carrier 240.

Figure 9:
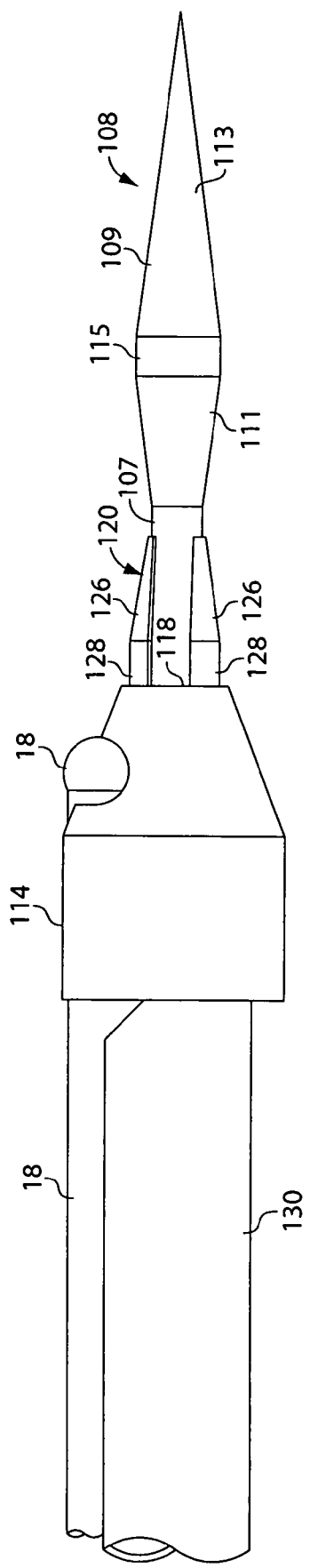
FIG. 9 is a sideview of a needle carrying a suture tag with the suture tag lock in the unlocked position.

As best shown in FIG. 20, the initial position of the proximal end of the pawl arm 256 and the pawl track 258 is represented by reference numeral 261. When the plunger carrier 240 first moves distally, the pawl arm slides in the pawl arm slides in the pawl track to the second position indicated at 262 before any movement of the pawl arm 250 occurs. After reaching the second position at 262, the pawl arm then begins to travel with the plunger carrier 240 during the remainder of the initial distal stroke of the plunger 216. That movement following the bottoming out of the pawl arm at position 262 serves to move the locking sleeve distally but not as far as the distal movement of the needle. The further distal advancement of the needle created by the pawl mechanism causes disengagement of the suture tag lock 120 as shown in FIG. 9 so that the suture tag 114 can be left behind the suture tag catch 140.

Figure 25:
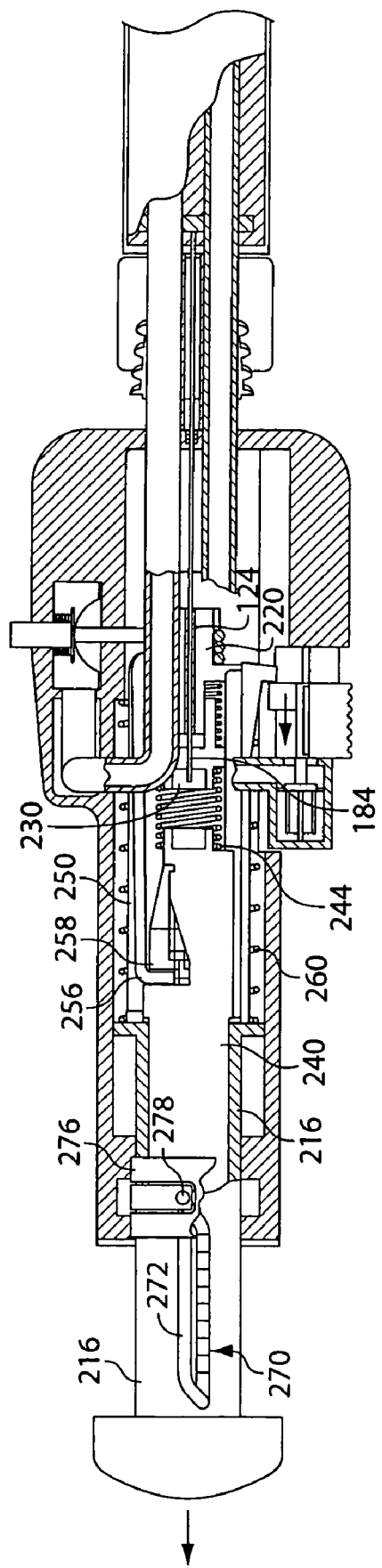
FIG. 25 is a sectional view of the control handle in an intermediate stage in which the needle has deposited the suture tag in the suture catch at the distal end of the capsule.

When the user releases the plunger from its fully depressed configuration shown in FIG. 24, the plunger returns to an intermediate position shown in FIG. 25. In this position, the needle is withdrawn proximally from the suture tag catch to a position that is proximal to the suction chamber 106. The tag 114 is left behind in the suture tag catch 140. The needle and suture tag lock remain in the same relative unlocked position at this stage. The needle and suture tag locking sleeve 124 remain in the same relative position due to the locking effect of the pawl track 258. As shown in FIG. 25 and FIG. 20, the pawl arm 256 is now maintained in the third position shown at reference numeral 263 of the pawl track which serves to maintain the needle carrier 230 advanced relative to the locking sheath carrier 220. The entire assembly has been moved proximally by the return force of the handle return spring 260 which generated an automatic proximal return stroke for all components including the plunger 216, plunger carrier 240, and by virtue of pawl arm 250, both the needle carrier 230 and locking sheath carrier 220.

To advance the needle a second time to retrieve the suture tag, either after a second tissue portion has been suctioned into the suction chamber 106 or prior to suctioning another tissue area, the user again advances the plunger 216 distally to its fully distal stroke. This final stroke in the sequence serves to move all components to the maximum distal travel as previously shown in FIG. 24. However, because the pawl arm 256 is guided to the location identified by reference numeral 264 in the pawl track 258 shown in FIG. 20, the proximal return stroke experienced by the handle under the resilient force of handle spring 260 will cause the pawl arm 256 to follow the track back to its initial position 261.

The pawl arm 256 is guided through this specific pattern in the around-the-world track 258 due to the elevation change of each segment of the tract shown in the cross-sectional drawing of FIG. 21. Because the pawl arm is formed to have a resilient downward bias, as it travels through each segmented elevation change, it resiliently springs down to the next level once it is reached. As a result, during the final proximal return stroke, the pawl returns to the original position at 261 which creates a relative movement between the suture tag lock sheathing 124 and needle 108 such that the locking splines 126 are again splayed outward by the spear-shaped distal end 109 of the needle to lock the suture tag 114 in place. The plunger ratchet mechanism permits full return to its original position shown in FIG. 17. As the pawl arms 278 follows a descending path in the three-dimensional track 272 to proceed away from the ratchet teeth 282 to the bottom of the stroke at 274. The needle deployment spring 244 also resiliently expands to provide proximal motion for the entire needle and suture tag lock sheath assembly. The resulting configuration of the handle is that shown in FIG. 17 and the capsule is returned to its initial state with the needle, suture tag withdrawn to the proximal side of the suction chamber 106.

Suture Lock and Delivery Device

The suture lock and suture lock delivery device of the present invention contribute to the utility of the system by providing a mechanism for securing the suture that avoids the cumbersome task of knot tying it provides a mechanical suture retainer that can be delivered through the working channel of the endoscope obviating the need to re-intubate with another instrument to complete the procedure. The suture lock and delivery device described herein is similar to that disclosed in pending U.S. patent application Ser. No. 10/275,534 corresponding to PCT Publication No. WO 01/89393. The entirety of the U.S. Patent Application is incorporated by reference herein in its entirety.

Figure 26A:
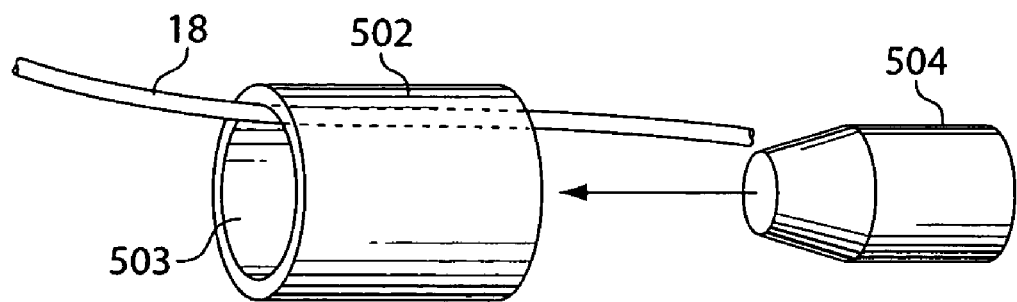
FIGS. 26A and 26B are side views of the suture lock of the present invention.
Figure 26B:
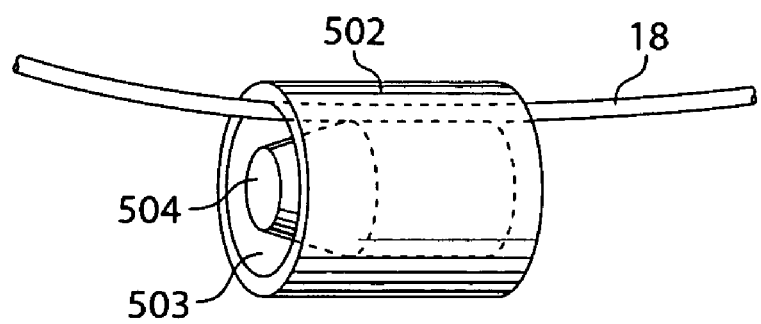

The suture lock of the present invention is shown in FIGS. 26A and B. FIG. 26A, a disassembled suture lock as shown comprising a ring 502 having a through bore 503 sized to receive with frictional engagement a plug 504 to capture a suture 18 that has been passed through the through bore 503. FIG. 26B shows the assembled configuration of the ring and plug suture lock with the plug 504 inserted into the through bore 503 of the ring 502 to capture the suture 18 between the surfaces of the plug and ring. It is noted that in FIG. 26B that the gap between the plug and the ring has been exaggerated to illustrate that the suture 18 is present between those two components, but it should be understood that the suture is tightly engaged between them so that it cannot slide through.

Figure 27:
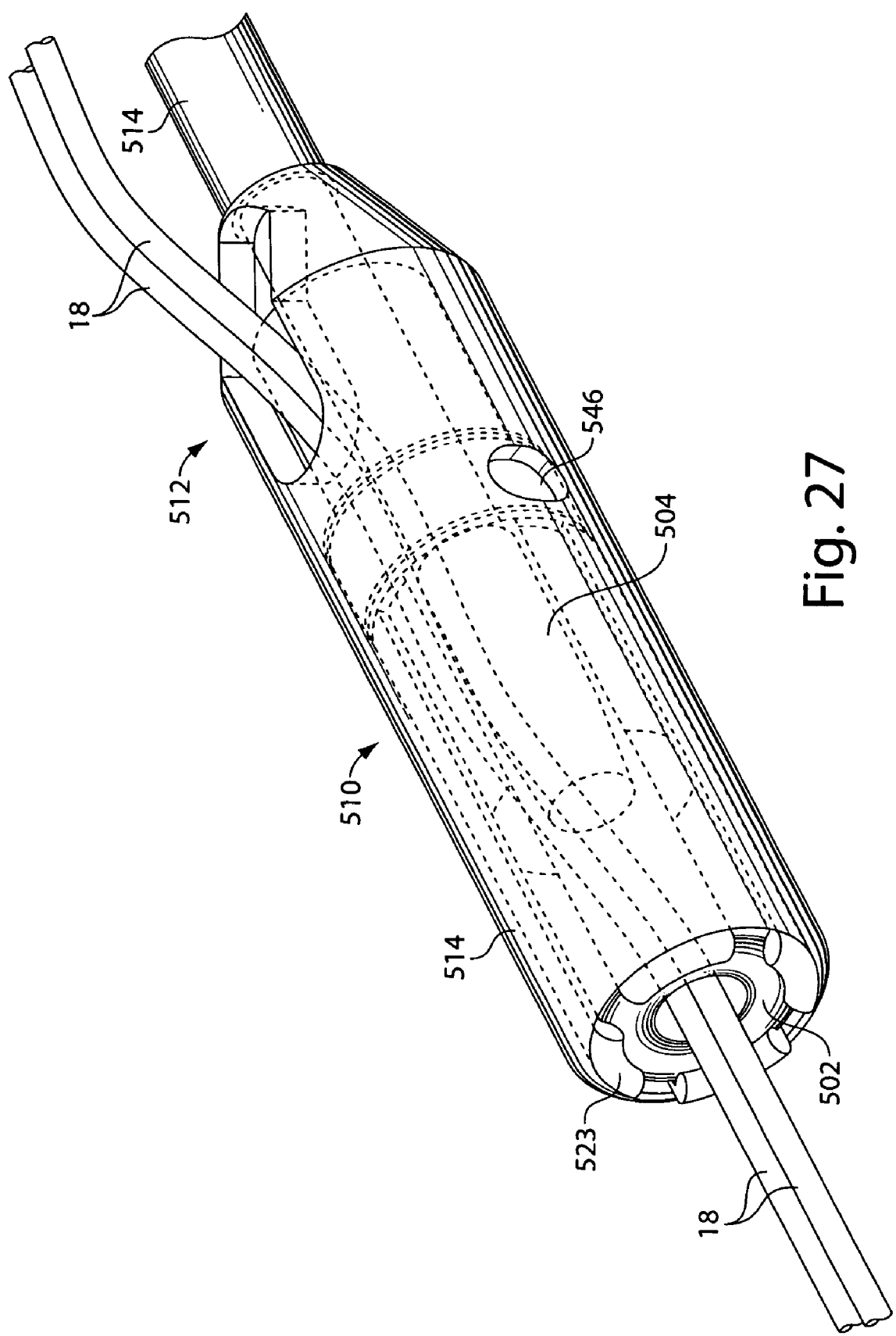
FIG. 27 is an isometric view of the suture lock delivery device.

FIG. 27 shows the operating distal end 510 of a suture lock delivery device 512. The operating distal end is attached to a shaft 514 that is of sufficient length to extend through the full length of the working channel of an endoscope and protrude at the proximal end for engagement with a control handle 550 (shown in FIGS. 27 and 28-36 that follow), the components of the distal operating end of the suture lock delivery device can be seen. The device comprises an outer sleeve 516 through which is slidable a cage 518 defined by plurality of rigid fingers 520 inchedly attached at their proximal ends 522 to a bushing member 524. Circumferentially spaced fingers are mounted to the distal end 226 of the bushing 224 such that when the fingers are extended beyond the sleeve 516 they resiliently spring open radially at their distal ends 521. In their closed configuration, the fingers define a cage that serves as a receptacle 528 for the disassembled plug and ring components that must be navigated to the suture location through the working channel of the endoscope. The receptacle defined by the cage 518 serves to maintain the plug and ring in alignment so that they may be assembled easily at the remote location.

Figure 28:
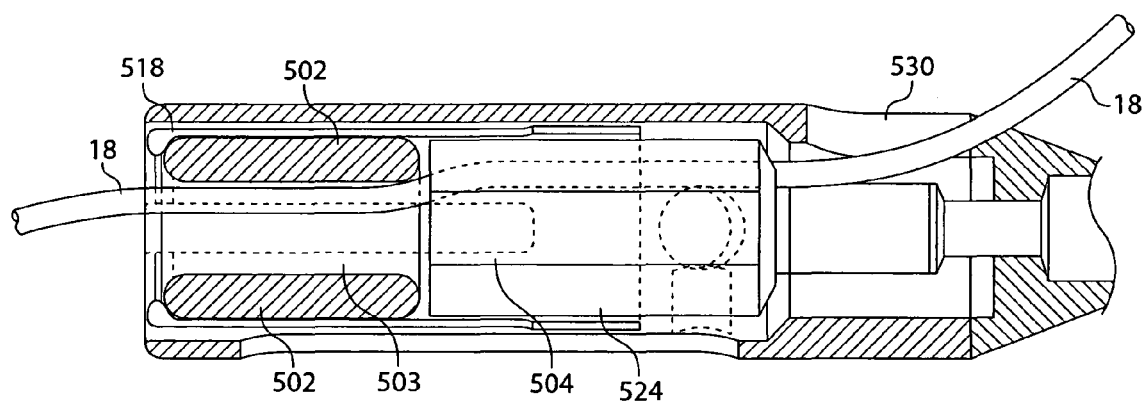
FIG. 28 is a sectional view of the suture lock delivery device.
Figure 29:
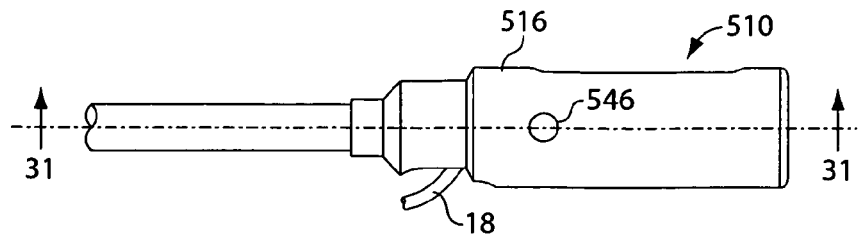
FIG. 29 is a side view of the suture lock delivery device.
Figure 30:
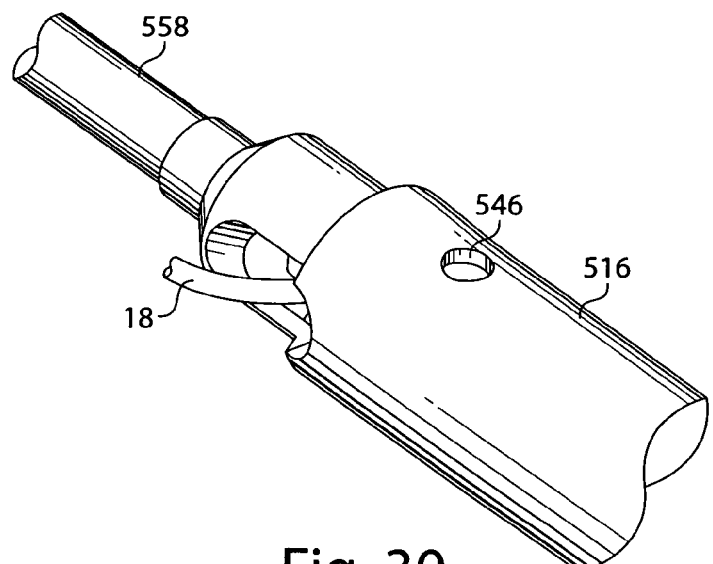
FIG. 30 is a isometric view of the suture lock delivery device.

As shown in FIG. 27, when the suture placement in the tissue has been completed, the components of the needle and suture tag lock assembly, along with the control handle are removed from the endoscope working channel in their entirety. Though the capsule remains mounted on the distal end of the endoscope, the working channel provides adequate space for introduction of the suture lock delivery system device 512. The distal operating member 510 has sufficient space to operate as it protrudes from the distal end of the working channel of the endoscope in the suction cavity 106 of the capsule. When the distal operating member of the suture lock delivery device is inserted into the proximal end of the working channel of the endoscope, the suture leads 18 that extend through the working channel and through the tissue are first inserted through the ring 502 through its distal end, exiting its proximal end and being positioned around the plug 504 such that they extend through a proximal opening 530 of the sleeve 516 so that they can be held tight as the device is advanced to the internal location (FIGS. 28-30).

With the suture threaded through the device and the device advanced to the suture location, the suture may be pulled tightly to gather the tissue portions that have been sutured and the device operated to cinch the suture leads and lock them in place to hold the tissue. The operation of the suture lock delivery device and operation of assembling the ring and plug and releasing the assembled component is preferably accomplished with a single distal stroke of a control handle actuator.

Figure 37:
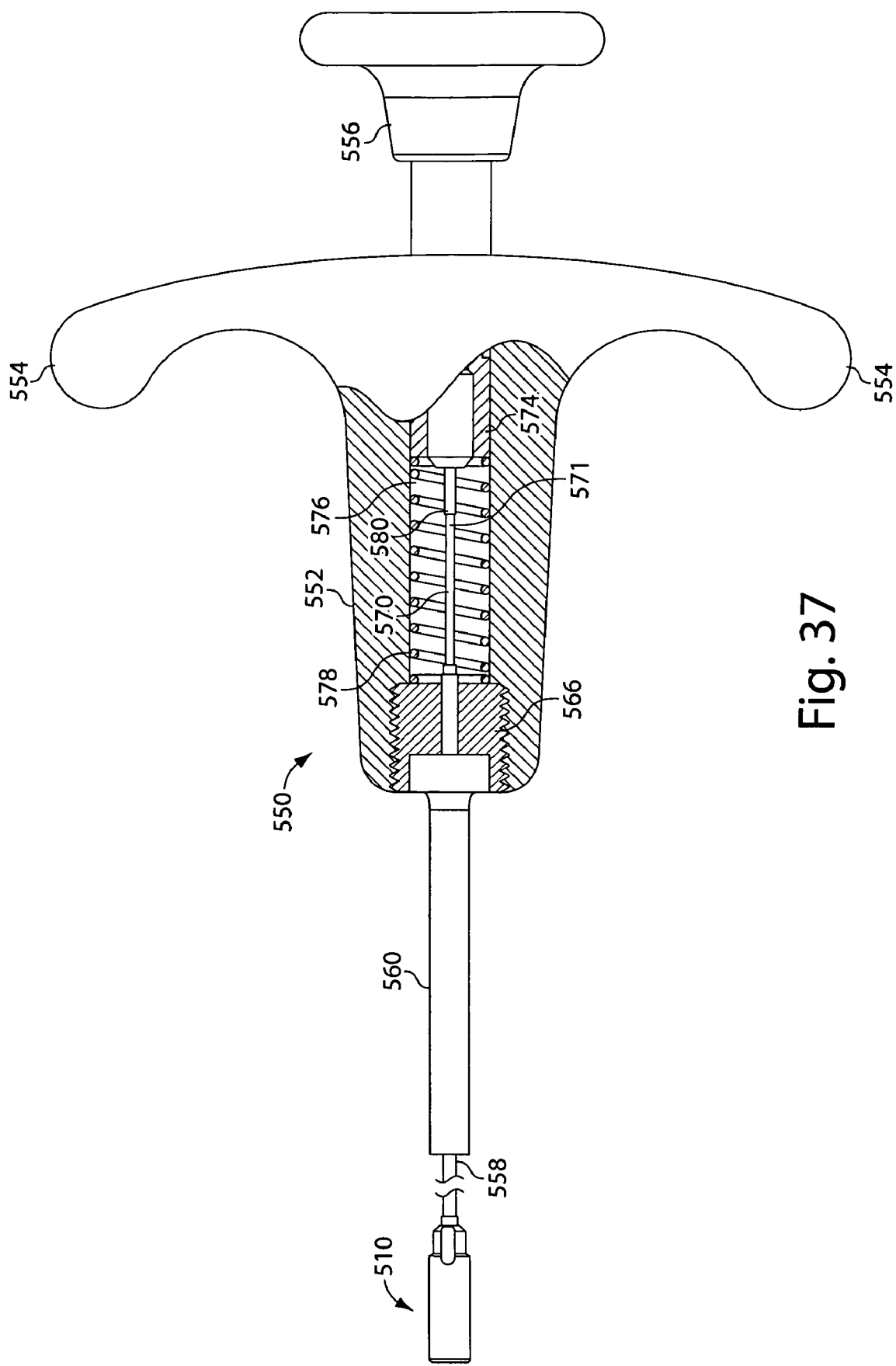
FIG. 37 is a side sectional view of the suture lock delivery device control handle.
Figure 38:
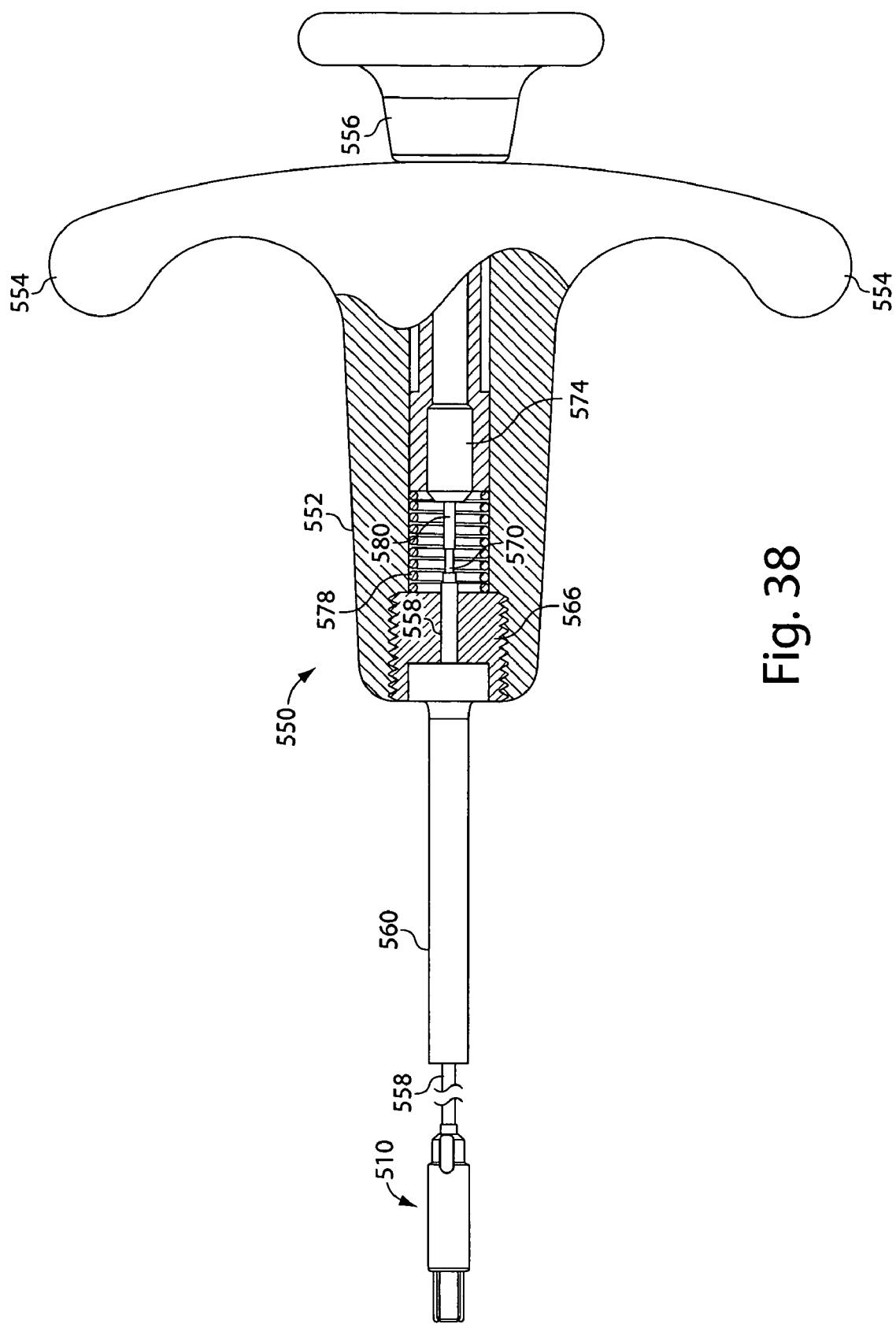
FIG. 38 is a side sectional view of the suture lock delivery device control handle in the depressed configuration.

FIGS. 37 and 38 show a control handle that is configured for operating a delivery device with a single distal stroke of a control mechanism. The control handle 550 comprises a housing 552 with formed finger rings 554 to provide leverage in the users hand when depressing the plunger 556 distally. Extending distally from the control handle 550 is an outer shaft 558 protected by a short piece of strain relief 560 to prevent kinking in the area adjacent to the handle. The proximal end 562 of the outer shaft is joined to the body 552 of the handle. The proximal end 562 of the outer shaft is securely fastened to the body of the handle by bonding to a bushing 566 that is welded into the interior of the handle body 552. The distal end of the outer shaft 564 is joined to the outer sleeve 516. An inner shaft 570 is visible through the outer shaft 558 to operate a pusher 534 that pushes the plug 504 into the ring 502 during assembly in the cage 518. The inner shaft 570 is joined at its proximal end 571 to the plunger body 556. When the plunger is depressed, the inner shaft 570 moves distally to push the plug into the ring for assembly. The plunger shaft 556 is joined to a bushing 574 that is slidable with a close fit inside of a channel 576 in the body 552 of the handle. A return spring 578 mounted in the channel 576 between plunger bushing 574 and outer tube bushing 566 serves to resiliently push the plunger back to its proximal position after being fully depressed distally. A pusher stiffener 580 may be added to the inner shaft to enhance its resistance to buckling under the compressive loading that occurs during assembly of the plug into the ring.

Figure 31:
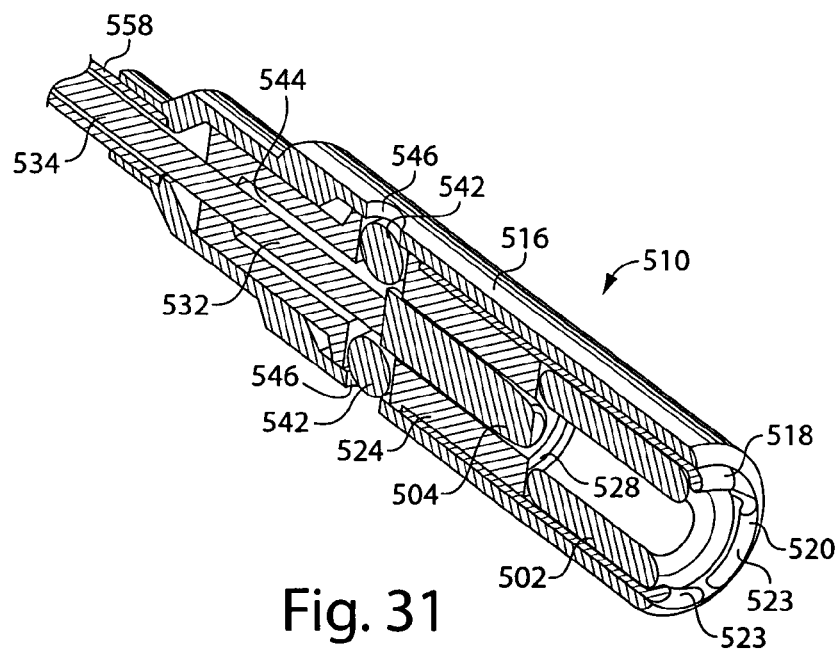
FIG. 31 is an isometric sectional view of the suture lock delivery device taken along the line A-A shown in FIG. 29.

Though the handle is provided with a single longitudinal pusher control in the form of a plunger 556, the capability for performing several functions at the distal end is provided by a locking structure that is automatically released solely by the longitudinal movement of the pusher through its ring and plug assembly stroke. As seen in FIGS. 31-36, bushing 524, the ring 502 and plug 504 are held in the receptacle 528 defined by the cage 518 prior to assembly (FIG. 31). The ring 502 is maintained distally against the radially inward curved tips 523 of the fingers 520. Because the inwardly curved tips 523 define a diameter that is smaller than that of the ring, the ring cannot slide past the tips until the fingers are opened. The plug 504 is maintained in alignment with the through bore 503 of the ring by placement in the bore of bushing 524.

Figure 32:
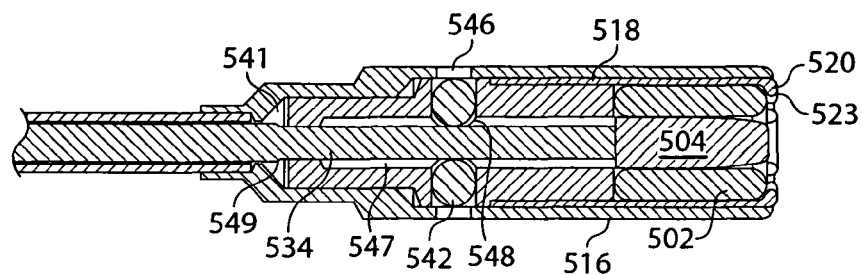
FIG. 32 is a sectional view of the suture lock delivery device with assembled ring and plug.
Figure 33:
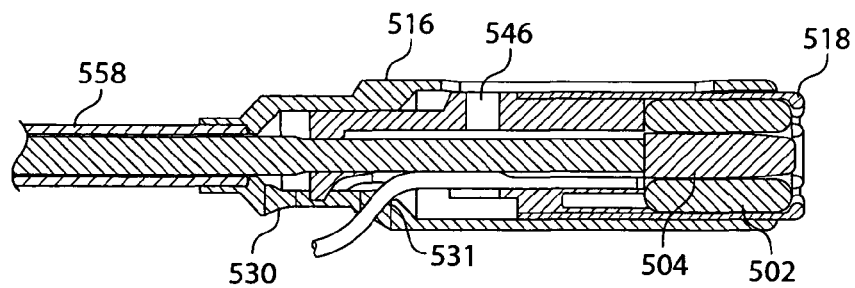
FIG. 33 is a sectional view of the suture lock delivery device taken from FIG. 29 in the orthogonal plane.

As seen in FIG. 31 immediately proximal to the aligned plug 504 is the distal end 532 of the pusher 534. When the plunger 556 of the control handle 550 is pushed distally, the inner shaft 570 pushes the pusher distally to insert the plug 504 into the ring 502 as is shown in FIG. 32. At this stage, the suture has been captured between the plug 504 and ring 502, but the assembled ring and plug must be released from the receptacle 528 defined by the cage 518. To accomplish this, the bushing 524 and cage 518 are made slidable relative to the outer sleeve 516 up to the point of where the proximal end of the fingers are hingedly attached to the bushing so that the distal ends of the fingers 521 may resiliently spring apart to release the assembled ring and plug.

To maintain the bushing and fingers stationary within the outer sleeve during assembly of the ring and plug but triggering release of the bushing and cage to slide distally relative to the sleeve after assembly of the ring and plug, locking balls 542 riding within recesses 544 formed in the bushing 524 are employed. The pusher shaft 534 forms the bottom surface of the recess that holds the locking balls. The space of the recesses 544 forces the balls into engagement with locking holes 546 formed in the outer sleeve 516. When the locking balls are forced into the locking holes 546, the bushing 524 and cage 518 cannot slide relative to the outer sleeve 516.

The locking balls can be triggered to release from the locking holes 546 at the moment the plug has been fully inserted into the ring 502 by forming a reduced diameter portion along the pusher shaft that corresponds to the stroke length required to complete insertion of the plug into the ring. When the reduced diameter portion reaches the locking balls, the recess in which they are contained enlarges, immediately releasing their engagement force against the locking holes 546 of the outer sleeve 516. The rounded surface of the balls immediately permits disengagement from the locking holes 546 and enables the bushing 524 with cage 518 and assembled ring and plug all to move distally relative to the sleeve if distal forces are maintained on the pusher shaft 534. The reduced diameter portion of the pusher is indicated at 548 in FIG. 32, which reaches the locking balls 542 at the moment the pusher has extended sufficiently to place the pusher plug 504 into the ring 502. Distal force is maintained on the bushing 524 by engagement of an enlarged diameter portion of the pusher beginning at 549 engaging the proximal end of the bushing 541 (FIG. 32).

Figure 34:
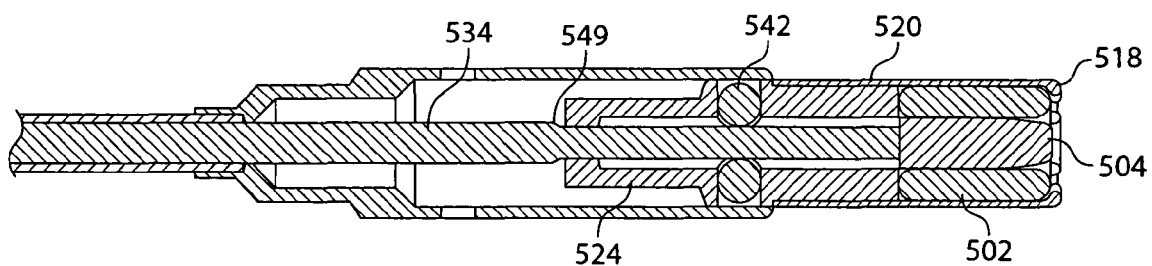
FIG. 34 is a sectional view of the suture lock delivery device with bushing and cage extended distally.
Figure 35:
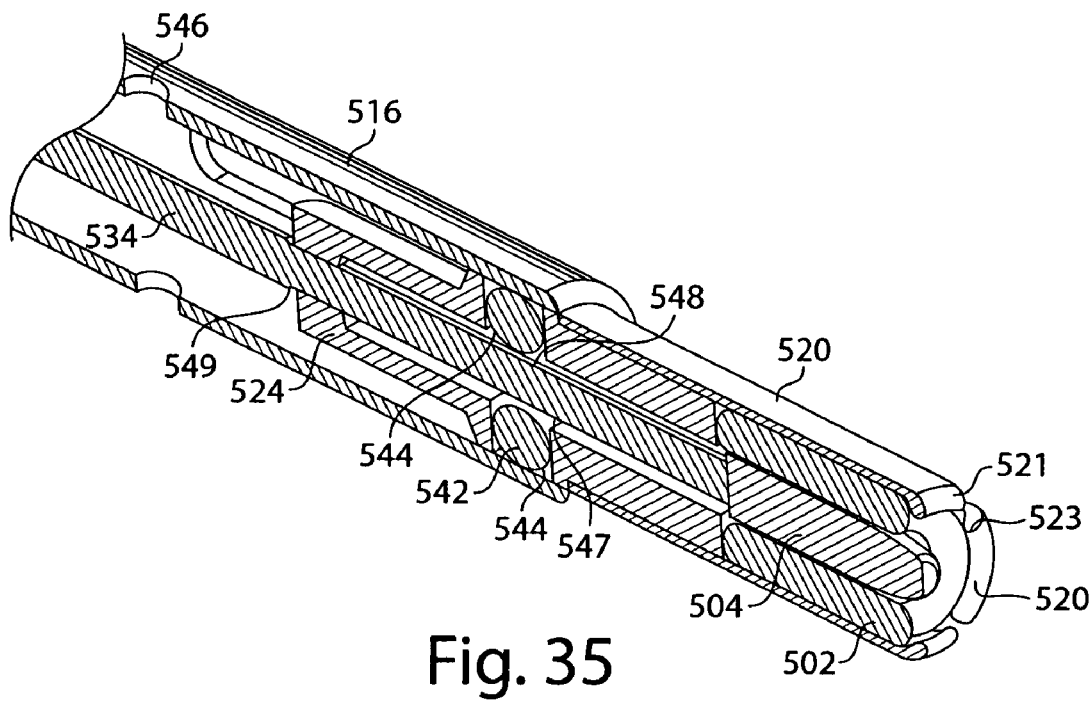
FIG. 35 is a sectional isometric view of the suture lock delivery device with bushing and cage extended distally.
Figure 36:
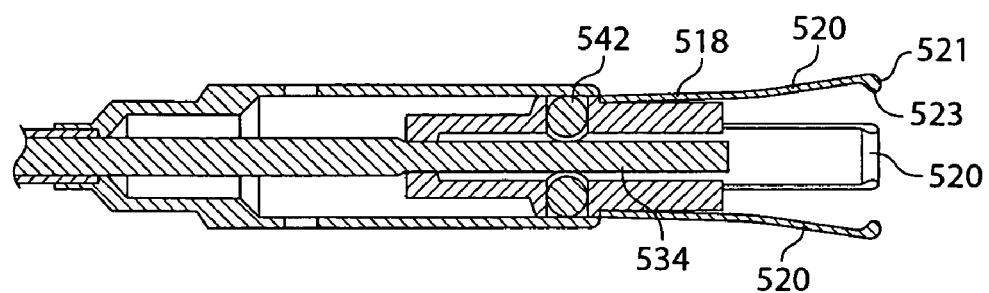
FIG. 36 is a sectional view of the suture lock delivery device with fingers extended radially outward to release a ring and plug.

With continued distal movement of the pusher 534, the bushing and cage assembly slide distally relative to the outer sleeve 516 as is shown in FIGS. 34 and 35. After the cage has been fully exposed from the outer sleeve, the fingers 520 resiliently spring open radially to permit release of the assembled ring and plug as is shown in FIG. 36. Excess suture leads are severed as the bushing crushes the sutures against sharpened edge 531 of sleeve opening 530 during the distal advancement of the bushing and cage 518. When the plunger 556 at the control handle 550 is released, return spring 578 causes the plunger to move proximally, which withdraws the pusher proximally until the first large diameter segment engages the proximal end of the bushing 524 pulling the bushing and cage back into the sleeve 516 under continued proximal movement of the pusher 534.

Operation

Figure 39:
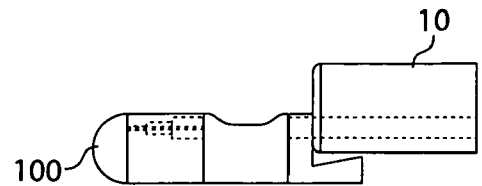
FIGS. 39-54 are diagrammatical illustrations of the various steps of the suturing process of the present invention.
Figure 40:
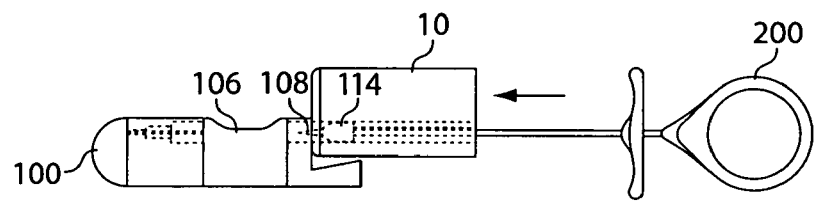
Figure 54:
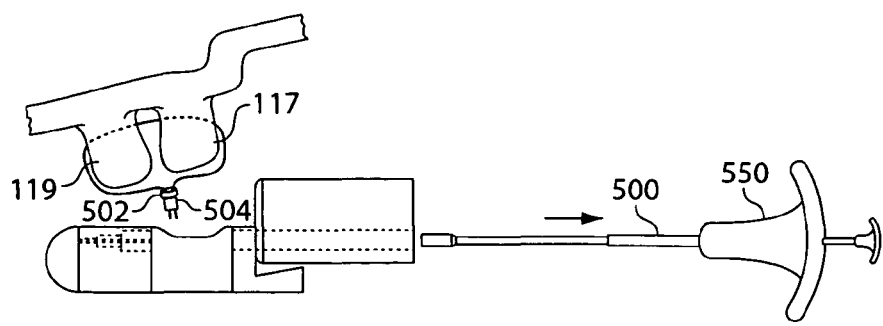
Figure 55:
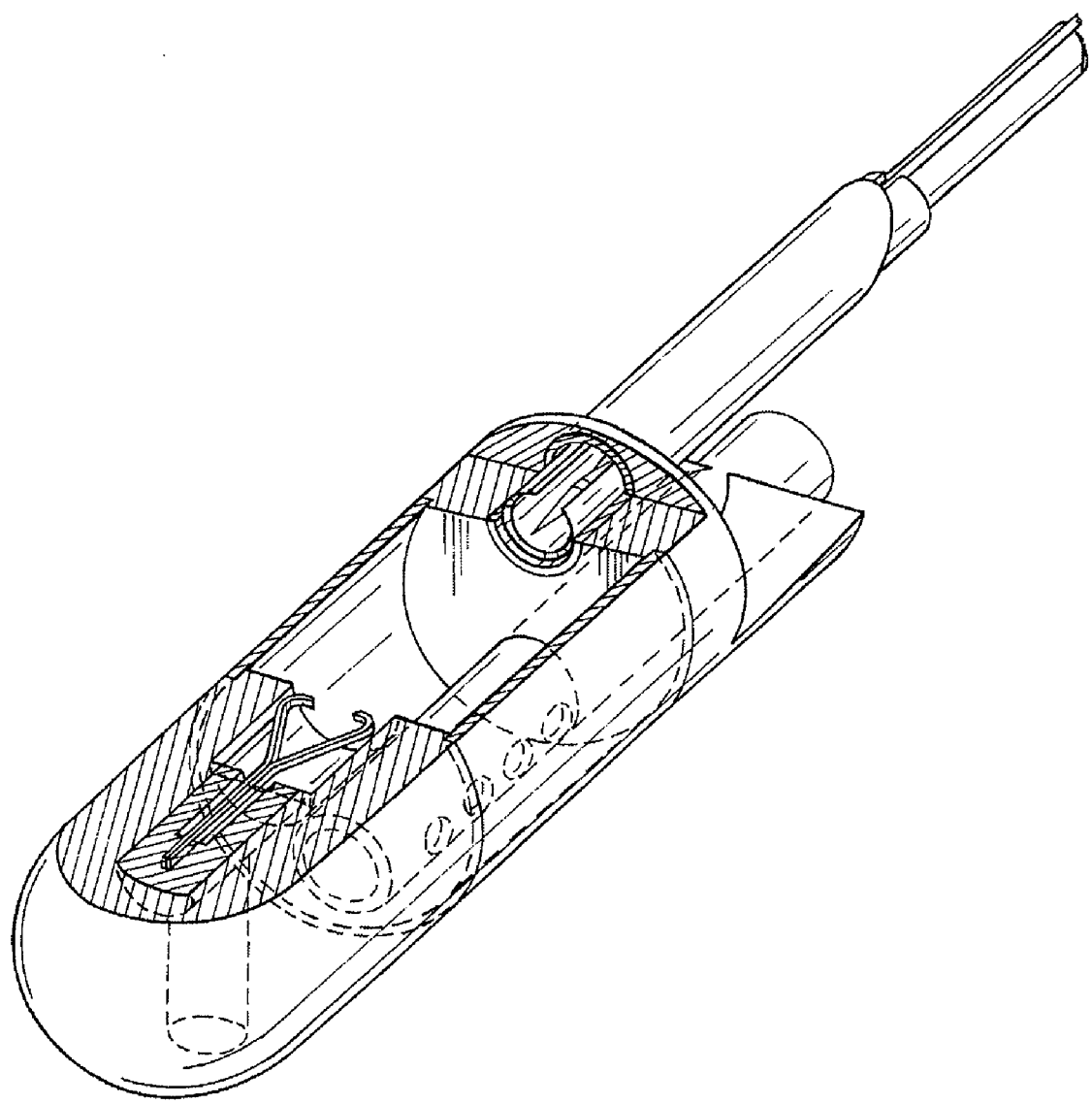
FIGS. 55-63 are diagrams representing various stages of the suturing process of the present invention.

The operation of single intubation suturing system described above will now be explained with reference to schematic illustrations shown in FIGS. 39-54 in conjunction with drawings presented in FIGS. 55-63. In operation of the device, the suturing capsule 100 is first mounted to the distal end of an endoscope 10 as shown in FIG. 39. With the needle 108 and the suture tag 114 positioned proximal to the suction chamber 106, the capsule endoscope assembly are advanced through a natural body lumen to the intended tissue location. This configuration is also shown in FIG. 55.

Figure 41:
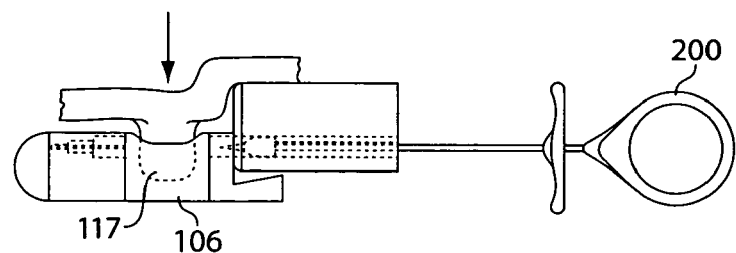
Figure 56:
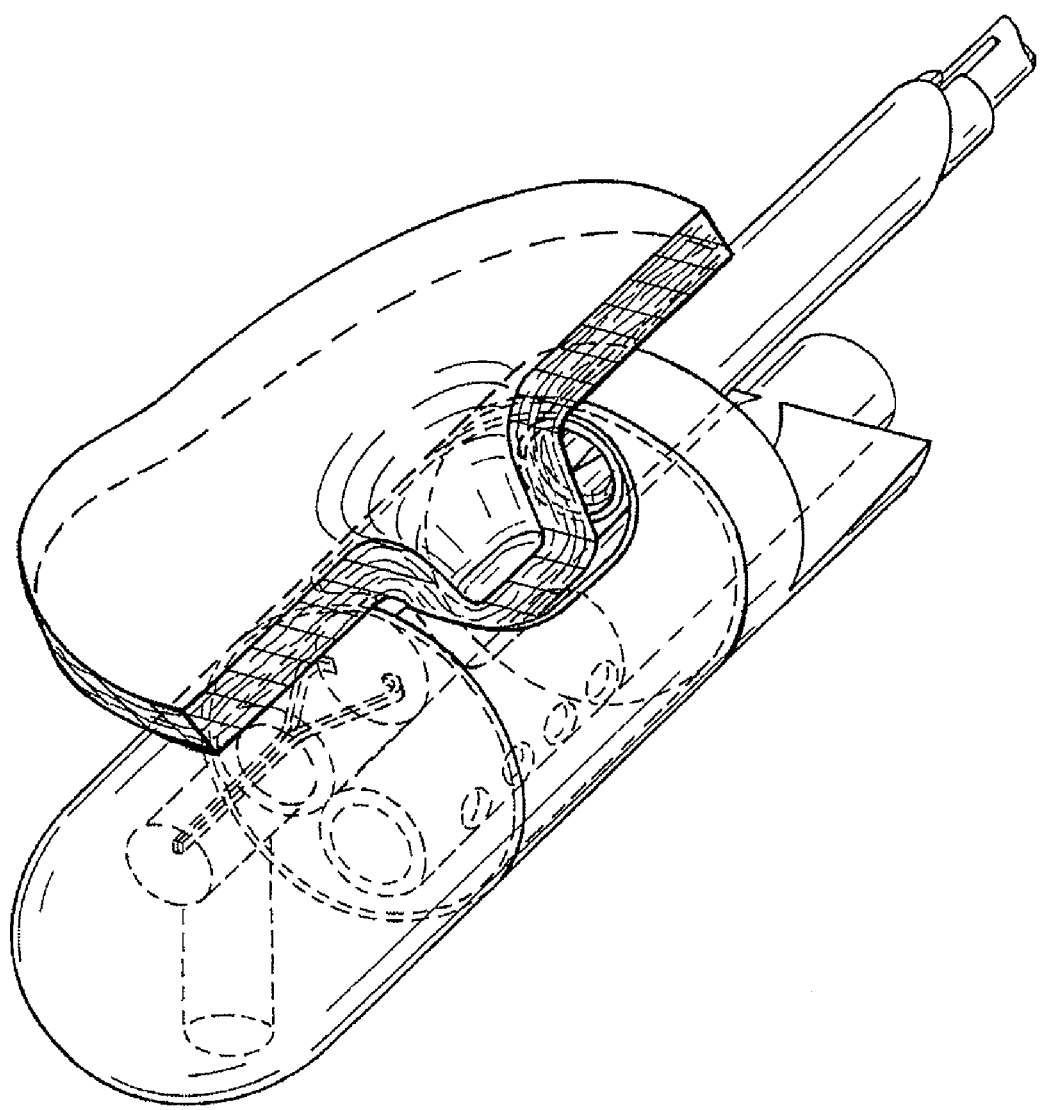

After reaching the intended tissue location, vacuum is applied to draw a tissue portion 117 into the suction chamber 106 as is shown in FIGS. 41 and 56.

Figure 42:
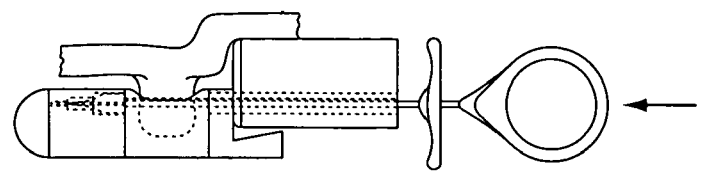
Figure 43:
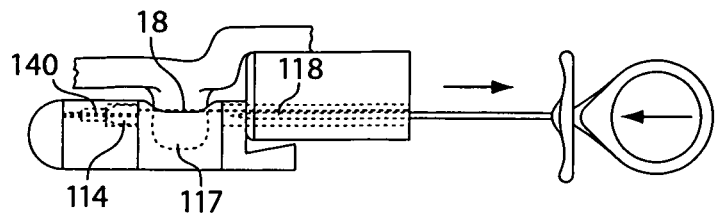
Figure 44:
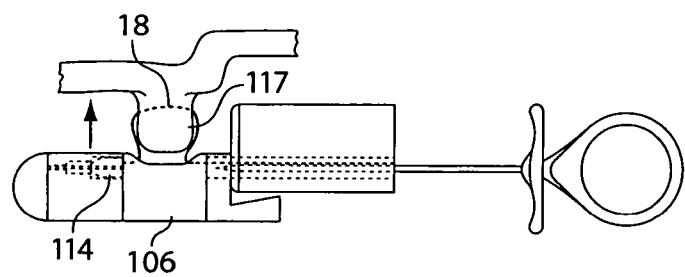
Figure 57:
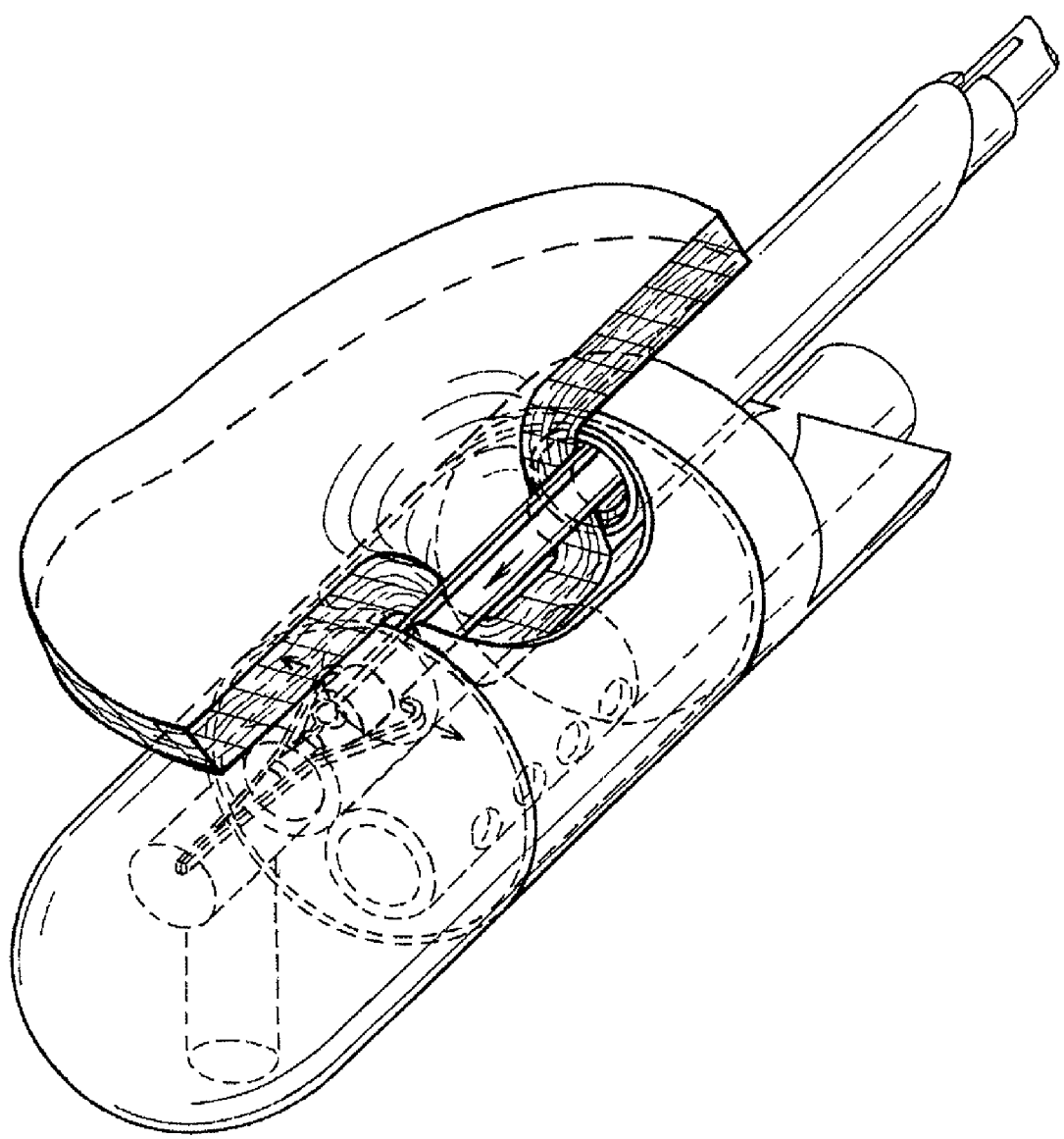
Figure 58:
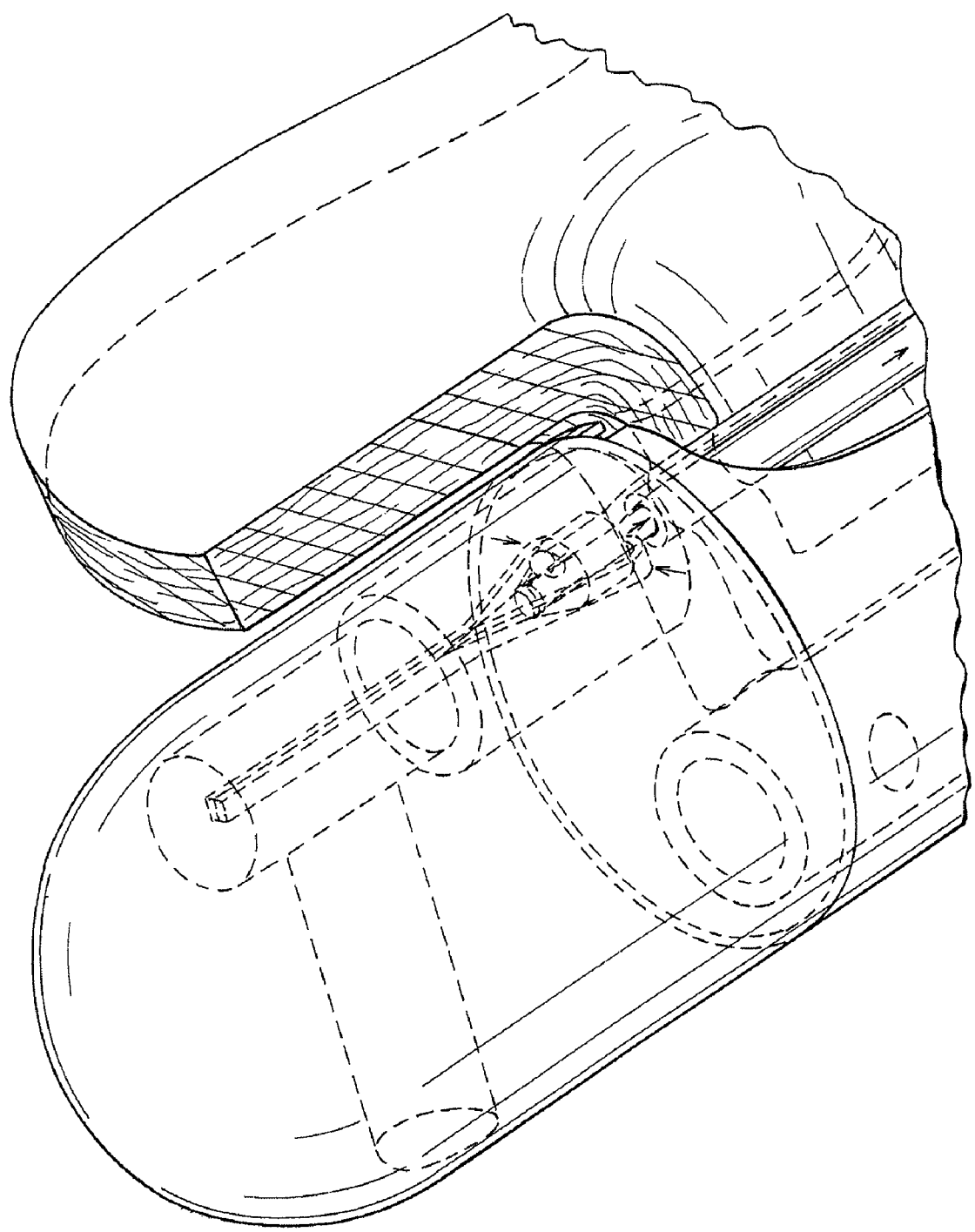
Figure 59:
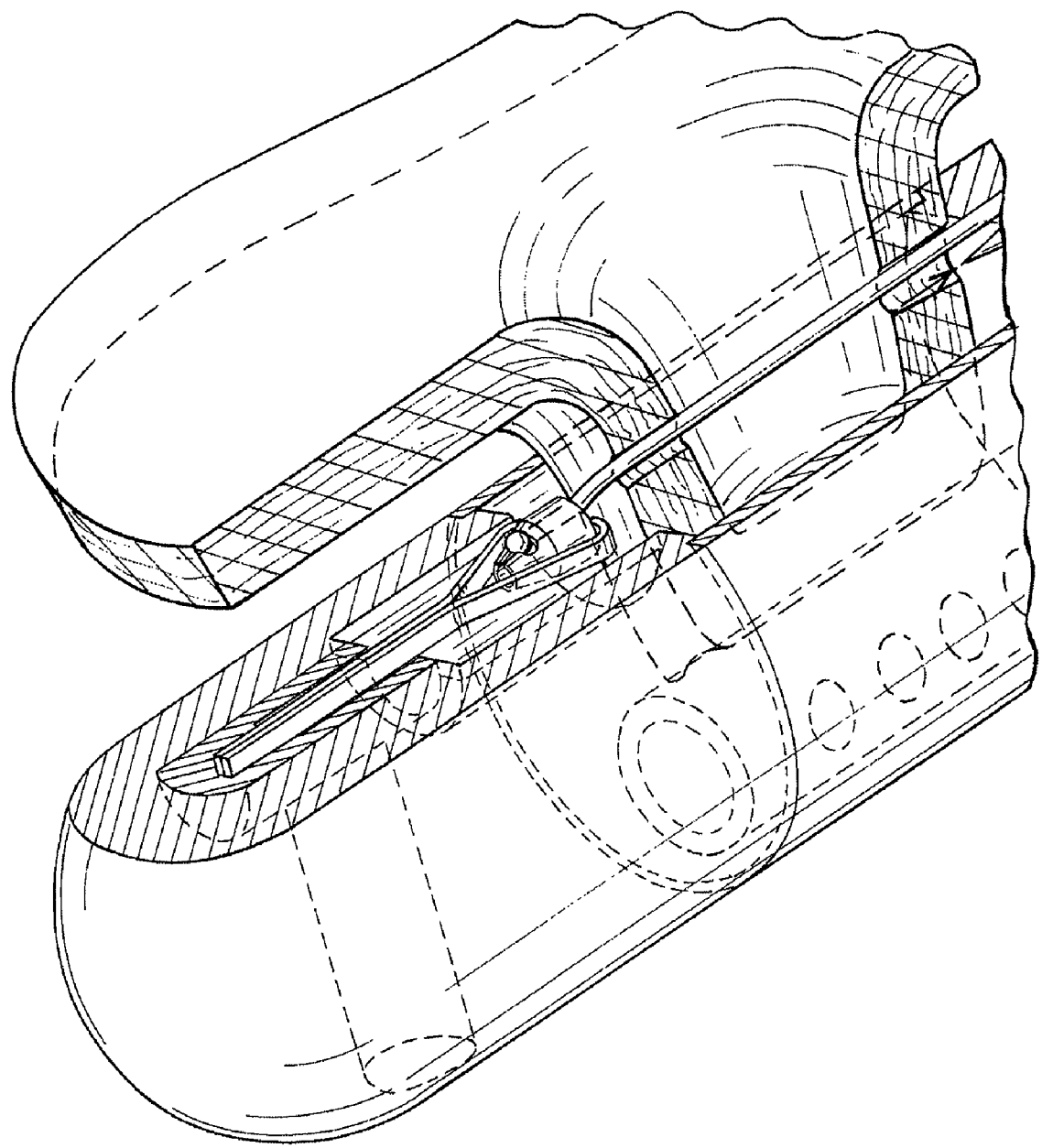

After tissue 117 has been suctioned, the needle 108 and suture tag 114 may be advanced distally through the tissue so that the needle and tag exit and enter the suture tag catch 140 as is shown in FIGS. 42, 57 and 58. Next, the suture tag 114 is released and the suture tag catch 140 and the needle is withdrawn proximally leaving the suture 18 placed through the tissue portion as is shown in FIGS. 43 and 59.

Figure 45:
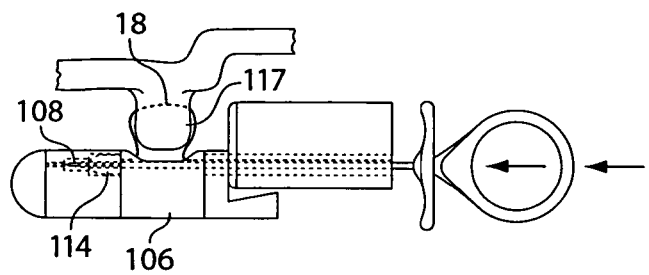
Figure 60:
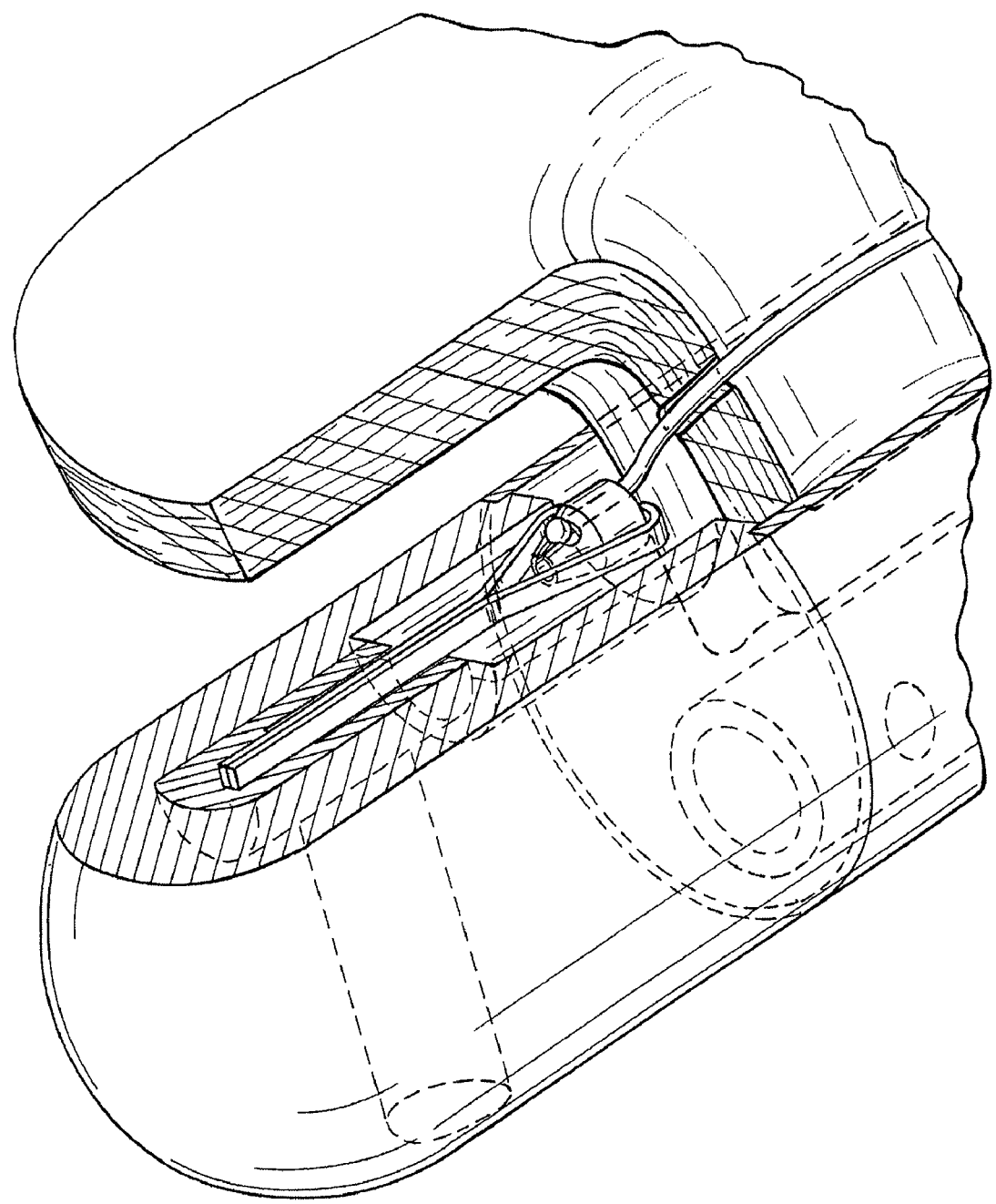
Figure 61:
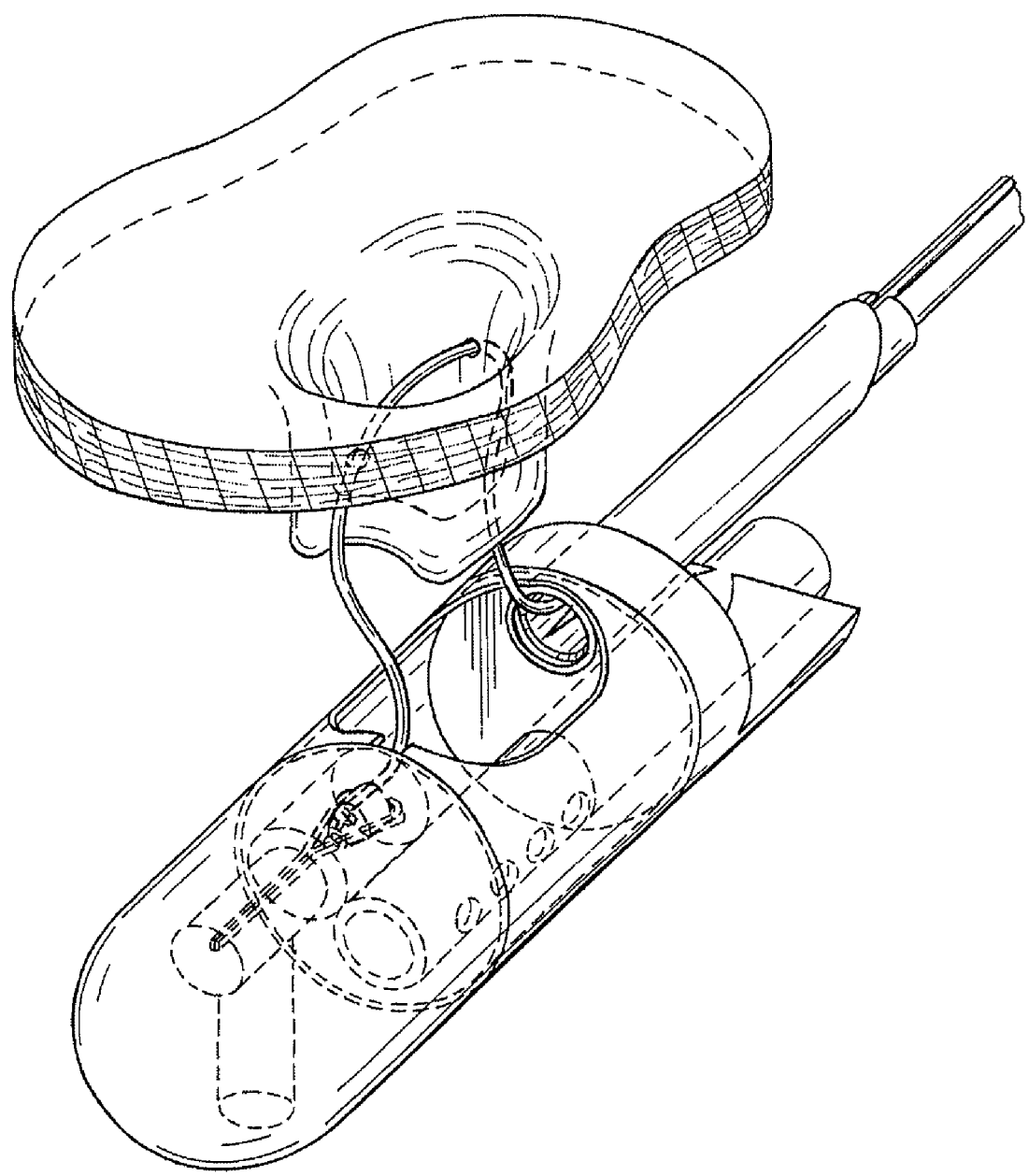

As shown in FIGS. 45, 60 and 61, the vacuum is discontinued and the tissue is released from the suction chamber 106 with the suture 18 passing through the tissue. After the tissue is released, either another tissue portion at a different location may be suctioned to be penetrated by the open needle and sutured during the proximal withdrawal stroke of the suture tag 114 through the tissue or, before applying suction to capture another tissue portion, the needle may be advanced distally to pick up the suture tag 114 and withdraw it proximally so that the suture will be advanced in the distal direction through the second tissue portion that is captured. In the figures, the latter method is illustrated wherein the suture tag is first retrieved and brought back proximally prior to the next suture.

Figure 46:
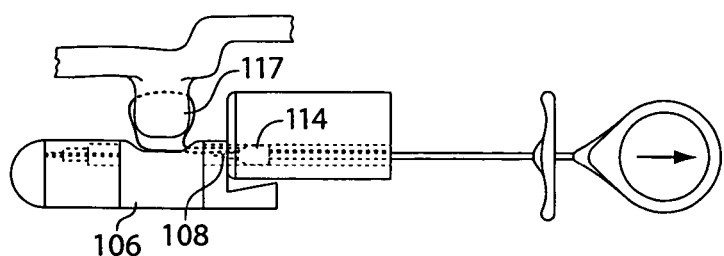
Figure 47:
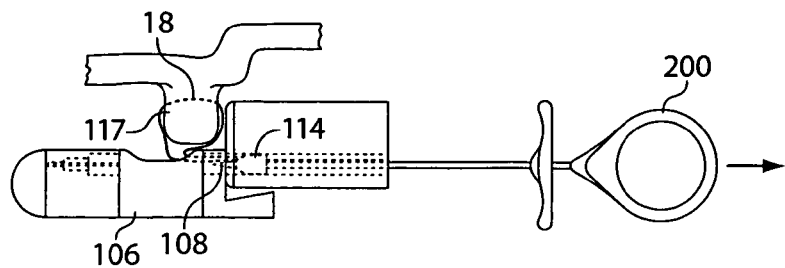
Figure 48:
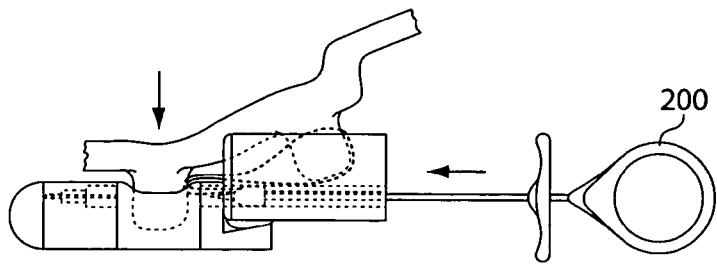
Figure 49:
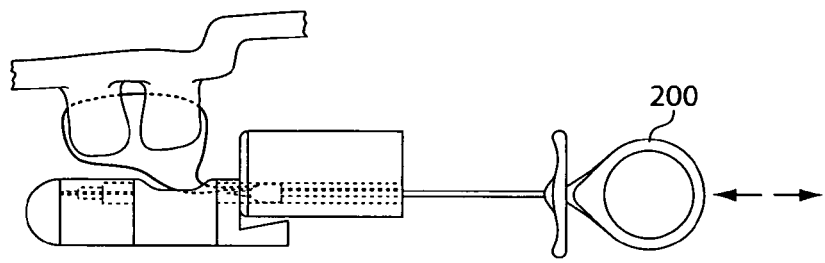
Figure 50:
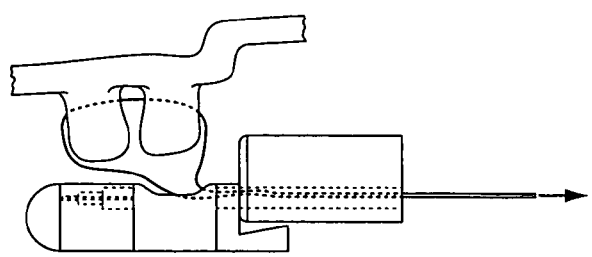
Figure 51:
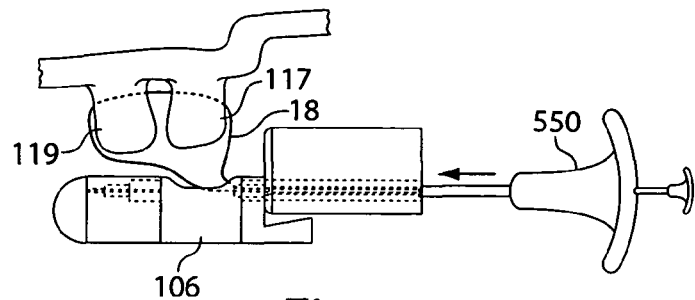
Figure 52:
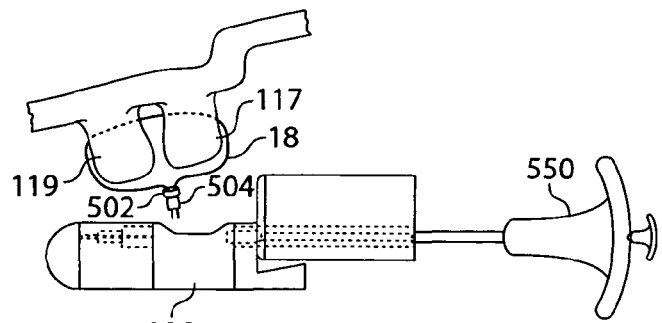
Figure 53:
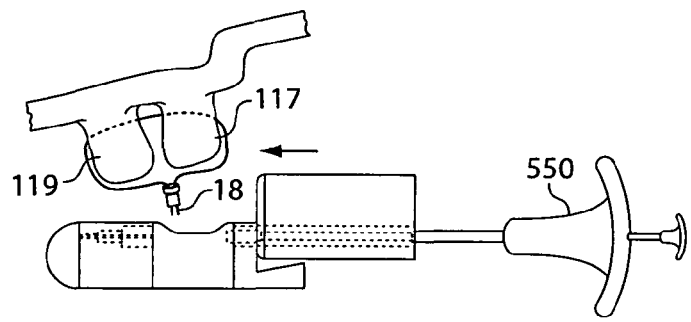
Figure 62:
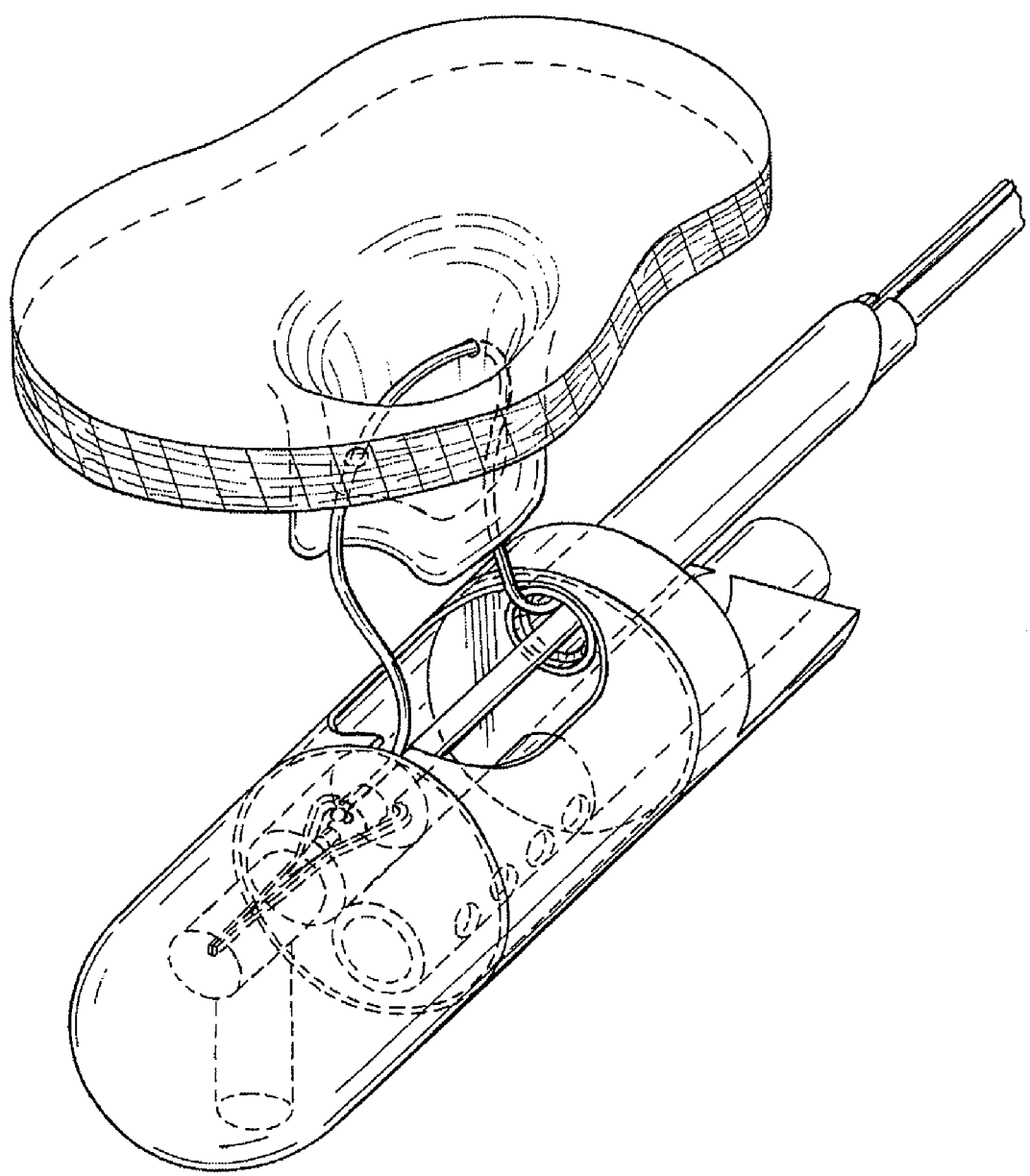
Figure 63:
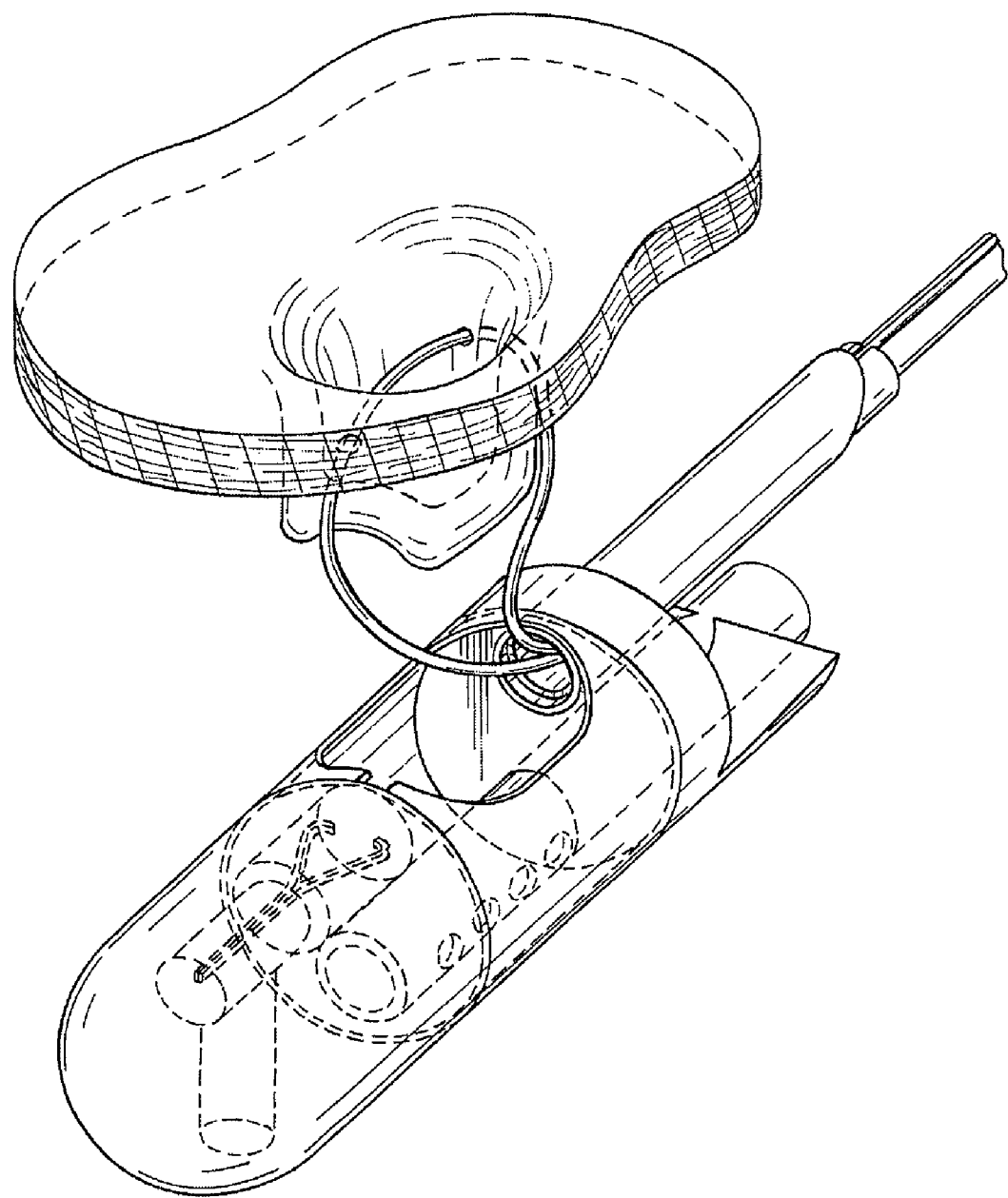

In FIGS. 45 and 62, it is shown that after release of the first sutured tissue portion 117, the needle 108 is advanced distally to recapture the suture tag in the suture tag catch 140. After the tag is secured onto the needle by the suture tag lock 120, the needle and tag assembly can be withdrawn proximally back into the needle track 110 at the proximal site of the suction chamber as is shown in FIGS. 46, 47 and 63. After the needle is retracted proximally with the suture tag, a second tissue portion 119 may be aspirated into the suction chamber and the above process repeated to place another suture at a second tissue location using the same suture 18 as is shown in FIGS. 48-50. After a desired number of tissue portions have been sutured with the suture material 18, the needle and control handle components related to the suturing device may be removed from the working channel of the endoscope and the suture lock delivery device 500 loaded with a ring 502 and plug 504 lock device may be inserted through the working channel of the endoscope so that the distal operating end 510 of the device extends into the suction chamber 106 of the capsule 100. As shown in FIGS. 52 and 53, a ring and plug 502 and plug 504 may be applied to the ends of the suture 18 to secure the suture to hold the tissue portions 117 and 119 together tightly. After the suture lock is applied, the suture lock delivery device 500 may be removed from the working channel of the endoscope as shown in FIG. 54 and the endoscope removed from the patient.

Having thus described the invention what we desire to claim and secure by Letters Patent is:

1. An endoscopic tissue suturing device comprising:
   a suturing capsule having a tissue suction chamber, needle track and a suture tag catch, wherein the suture tag catch is positioned distal to the tissue suction chamber;
   a needle slidable in the needle track and along a pathway that passes through the tissue suction chamber, the needle including a sharpened distal tip;
   a suture tag lock on an exterior surface of the needle; and
   a suture tag joined to a suture, the suture tag being capturable on the exterior surface of the needle by the suture tag lock and releasable from the needle into the suture tag catch when the suture tag lock is released and the needle is withdrawn proximally, the suture tag configured to be confined distal to the tissue suction chamber and not extend into the tissue suction chamber when the suture tag is retained by the suture tag catch and released from the needle.

2. An endoscopic tissue suturing device as defined in claim 1 wherein the suture tag lock changes its position relative to the exterior surface of the needle to create a locking surface that engages the suture tag to prevent distal sliding movement of the tag relative to the needle.

3. An endoscopic tissue suturing device as defined in claim 2 wherein the exterior surface of the needle is shaped to engage the suture tag lock when the lock is moved longitudinally relative to the needle to form the locking surface.

4. An endoscopic tissue suturing device as defined in claim 3 wherein the suture tag lock comprises at least two locking splines that are spread open as they slide over an enlarged surface of the needle to create the locking surface that holds the suture tag from longitudinal movement.

5. An endoscopic tissue suturing device as defined in claim 4 wherein the needle is solid and has a spear-shaped distal end with straight tapered barrel surfaces extending from the proximal and distal directions meeting at a central increased diameter section to define an enlarged shape.

6. An endoscopic tissue suture device as defined in claim 1 wherein the suture tag catch comprises two resilient arms bound together at one end of their ends in a Y-configuration each with a prong-shaped free end having an inwardly projecting edge configured to engage a surface of the suture tag.

7. An endoscopic tissue suturing device as defined in claim 6 wherein the suturing capsule further comprises a cavity which is configured to closely fit around the surface of the suture tag while permitting movement of the resilient arms of the suture tag catch.

8. An endoscopic tissue suturing device as defined in claim 1 wherein the suture tag is annular and slidable over the exterior surface of the needle.

9. An endoscopic tissue suturing device as defined in claim 8 wherein the tag has proximal and distal ends and is tapered at least at its distal end to present a low profile as the needle is advanced distally through tissue.

10. An endoscopic tissue suturing device as defined in claim 8 wherein the suture tag lock is located between an inner surface of the suture tag and the exterior surface of the needle when the suture tag is supported on the needle.

11. An endoscopic tissue suturing device as defined in claim 1 further comprising a control handle releasably securable to a proximal end of an endoscope and having at least one longitudinal control member joined to a shaft extending through a working channel of an endoscope to control the longitudinal movement of the needle.

12. An endoscopic tissue suturing device as defined in claim 11 wherein the handle further comprises a control mechanism for actuating the suture tag lock during a portion of a stroke of the longitudinal control member that operates the needle.

13. An endoscopic tissue suturing device as defined in claim 12 wherein the longitudinal control member of the handle includes an around-the-world pawl and track mechanism oriented to cause movement of a suture tag lock control shaft during only a portion of the longitudinal stroke of the control mechanism that operates the needle.

14. An endoscopic tissue suturing device as defined in claim 11 wherein the control handle further includes a vacuum control switch including an interlock feature that prevents longitudinal movement of the handle control members until a pre-established vacuum pressure to the suction chamber of the capsule is achieved.

15. An endoscopic tissue suturing device as defined in claim 1 wherein the suture tag lock extends longitudinally along a length of the needle.

* * * * *